US011427858B2

(12) United States Patent
Meller et al.

(10) Patent No.: US 11,427,858 B2
(45) Date of Patent: Aug. 30, 2022

(54) METHODS OF DETECTING MODIFIED AND UNMODIFIED DNA

(71) Applicants: TECHNION RESEARCH & DEVELOPMENT FOUNDATION LIMITED, Haifa (IL); RAMOT AT TEL-AVIV UNIVERSITY LTD., Tel Aviv (IL)

(72) Inventors: Amit Meller, Haifa (IL); Tal Gilboa, Haifa (IL); Chen Torfstein, Haifa (IL); Yuval Ebenstein, Tel Aviv (IL); Elmar Weinhold, Aachen (DE); Yael Michaeli-Hoch, Tel Aviv (IL); Assaf Grunwald, Tel Aviv (IL)

(73) Assignees: TECHNION RESEARCH & DEVELOPMENT FOUNDATION LIMITED, Haifa (IL); RAMOT AT TEL-AVIV UNIVERSITY LTD., Tel Aviv (IL)

( * ) Notice: Subject to any disclaimer, the term of this patent is extended or adjusted under 35 U.S.C. 154(b) by 224 days.

(21) Appl. No.: 16/635,276

(22) PCT Filed: Jul. 31, 2018

(86) PCT No.: PCT/IL2018/050854
§ 371 (c)(1),
(2) Date: Jan. 30, 2020

(87) PCT Pub. No.: WO2019/026075
PCT Pub. Date: Feb. 7, 2019

(65) Prior Publication Data
US 2020/0340032 A1 Oct. 29, 2020

Related U.S. Application Data

(60) Provisional application No. 62/538,881, filed on Jul. 31, 2017.

(51) Int. Cl.
*C12Q 1/683* (2018.01)
*C12Q 1/48* (2006.01)

(52) U.S. Cl.
CPC .............. *C12Q 1/683* (2013.01); *C12Q 1/48* (2013.01); *C12Q 2521/331* (2013.01); *C12Q 2527/125* (2013.01); *C12Q 2563/113* (2013.01); *C12Q 2565/631* (2013.01); *C12Y 201/01* (2013.01); *G01N 2333/91017* (2013.01)

(58) Field of Classification Search
CPC ........ C12Q 1/683; C12Q 1/48; C12Q 1/6806; C12Q 1/6869; C12Q 2521/331; C12Q 2527/125; C12Q 2563/113; C12Q 2521/125; C12Q 2565/631; C12Q 2525/101; C12Q 2537/164; C12Y 201/01; G01N 2333/91017
See application file for complete search history.

(56) References Cited

U.S. PATENT DOCUMENTS

| 2002/0197639 | A1* | 12/2002 | Shia .................. C12Q 2522/101 435/6.12 |
| 2011/0165564 | A1* | 7/2011 | Weinhold ............... C07H 19/16 435/6.11 |
| 2014/0221218 | A1* | 8/2014 | Cao ...................... C12Q 1/6806 506/2 |
| 2015/0105297 | A1* | 4/2015 | Stakenborg .............. C12Q 1/68 506/12 |
| 2016/0355542 | A1* | 12/2016 | Bestor ..................... C12P 19/34 |
| 2016/0369331 | A1* | 12/2016 | Saghbini ................ G16B 20/30 |

FOREIGN PATENT DOCUMENTS

| WO | 2005121361 A3 | 12/2005 |
| WO | 2015171169 A1 | 11/2015 |

OTHER PUBLICATIONS

Ahern, Biochemical, Reagents Kits Offer Scientists Good Return On Investment, 1995, The Scientist, 9, p. 20 (Year: 1995).*
Campos et al, Stochastic Detection of MPSA-Gold Nanoparticles Using a α-Hemolysin Nanopore Equipped with a Noncovalent Molecular Adaptor, 2016, Anal. Chem., 88, 6214-6222 (Year: 2016).*
Sun et al, Identifying DNA methylation in a nanochannel, 2016, Science and Technology of Advanced Materials, 17, 644-649. (Year: 2016).*
Tal Gilboa et al., "Single-molecule DNA methylation quantification using electro-optical sensing in solid-state nanopores." ACS nano, Issue 10 vol. 9 pp. 8861-8870, 2016.
Padmini Krishnakumar et al., "Slowing DNA translocation through a nanopore using a functionalized electrode", ACS Nano, Issue 7 vol. 11 pp. 10319-10326, 2013.
Jonas Korlach, Stephen W. Tymer, "Going Beyond Five Bases in DNA Sequencing", Curr. Opin. Struct. Biol. Issue 222 vol. 3 pp. 251-261, 2012.
Tyson A. Clark et al., "Enhanced 5-Methylcytosine Detection in Single-Molecule, Real-Time Sequencing Via Tet1 Oxidation", BMC Biology Issue 11 Article 4, 2013.
Meni Wanunu and Amit Meller, "Single-Molecule Analysis of Nucleic Acids and DNA-Protein Interactions Using Nanopores" Single-Molecule Techniques: A Laboratory Manual, Chapter 18 pp. 395-420, Cold Spring Harbor Laboratory Press NY, 2008.
Amit Meller, "Nanopores: Single-Molecule Sensors of Nucleic Acid-Based Complexes", Advances in Chemical Physics; Issue 149 pp. 251-268, 2013.

(Continued)

*Primary Examiner* — Narayan K Bhat
(74) *Attorney, Agent, or Firm* — The Roy Gross Law Firm, LLC; Roy Gross

(57) ABSTRACT

Methods and kits for detecting the presence of at least one target DNA sequence with or without a modification in a DNA molecule are provided.

20 Claims, 34 Drawing Sheets
(5 of 34 Drawing Sheet(s) Filed in Color)
Specification includes a Sequence Listing.

(56) References Cited

OTHER PUBLICATIONS

Andrew H. Laszlo et al., "Decoding long nanopore Sequencing Reads of Natural DNA", Nature Biotechnology, Issue 32 pp. 829-833, 2014.
Alon Singer et al., "Electronic Barcoding of a Viral Gene at the Single-Molecule Level", Nano Letters, Issue 12 pp. 1722-1728, 2012.
Allison Squires et al., "Nanopore Sensing of Individual Transcription Factors Bound to DNA", Scientific Reports, vol. 5 p. 11643, 2015.
Jiandong Feng et al., "Identification of Single Nucleotides in Mos2 Nanopores", Nature Nanotechnology Issue 10 pp. 1070-1076, 2015.
Osama K. Zahid et al., "Quantifying Mammalian Genomic DNA Hydroxymethylcytosine Content Using Solid-State Nanopores", Scientific Reports, Issue 6 p. 29565, 2016.
Jiwook Shim et al., "Detection and Quantification of Methylation in DNA Using Solid-State Nanopores", Scientific Reports Issue 3 Article 1389. 2013.
Ben McNally et al., "Optical Recognition of Converted DNA Nucleotides for Single-Molecule DNA Sequencing Using Nanopore Arrays", Nano Letters Issue 10 pp. 2237-2244, 2010.
Saulius Klimasauskas et al., "A New Tool for Biotechnology: Adomet-Dependent Methyltransferases", Trends Biotechnol. Issue 25 pp. 99-104, Mar. 2007.
Gisela Maria Hanz et al., "Sequence-Specific Labeling of Nucleic Acids and Proteins with Methyltransferases and Cofactor Analogues", Journal of Visualized Experiments, Issue 93 e52014, 2014.
Anna Gottfried and Elmar Weinhold, "Sequence-Specific Covalent Labelling of DNA", Biochemical Society Transactions Issue 39 pp. 623-628, 2011.
Yael Michaeli et al., "Optical Detection of Epigenetic Marks: Sensitive Quantification and Direct Imaging of Individual Hydroxymethylcytosine Bases", Chemical Communication (Cambridge, U. K.) Issue 49 vol. 77 pp. 8599-8601, Oct. 2013.
Wan Jun Poh et al: "DNA Methyltransferase Activity Assays: Advances and Challenges", Theranostics 2016, vol. 6, Issue 3.
Leila Syedmoradi et al: "Towards DNA methylation detection using biosensors", Analyst, The Royal Society of Chemistry, 2016, Issue 21, pp. 1-22.
Xiaoyin Sun et al: "Identifying DNA methylation in a nanochannel", Science and Technology of Advanced Materials, 17:1, 644-649, 2016.
PCT Search Report for International Application No. PCT/IL2018/050854 dated Nov. 28, 2018, 4 pp.
PCT Written Opinion for International Application No. PCT/IL2018/050854 dated Nov. 28, 2018, 6 pp.
PCT Preliminary Report on Patentability for International Application No. PCT/IL2018/050854 dated Feb. 2, 2020, 7 pp.

* cited by examiner

Labeling inhibits digestion

Methylation inhibits labeling

Step 1

| DNA | 1Kbp | Space | HOXA10 | HOXA10 | L1CAM | L1CAM | CDKN2B | CDKN2B |
|---|---|---|---|---|---|---|---|---|
| Atto532 | - | | - | + | - | + | + | - |
| CF640R | - | | - | + | - | + | + | - |
| Taq1 | - | | - | + | - | + | + | - |
| M.HhaI | - | | - | + | - | + | + | - |

SEQUENCE LISTING

<160> NUMBER OF SEQ ID NOS: 3

<210> SEQ ID NO 1
<211> LENGTH: 5240
<212> TYPE: DNA
<213> ORGANISM: Homo sapiens

<400> SEQUENCE: 1

```
gctccggaat tcttaccccc tccattttgc ttcctcgcct gtgaggtcat ggccttgagc      60
ctaggagggg gcactgggga ggagctcctt ccttctcgat cctgtgcagg gctgcggggg     120
agagtgggag agagtggagt cggcgggaaa ggtcgaatgg ggccaatccc gaggacaaag     180
aaataagaca ccagagagct ggaggaaaat ctgggagttg ggggtggcag ttcgagggat     240
accctctccc agaccctgtc tcccctgggc tcgcctccta ccctgccgcc cacctgggct     300
ctggggtgcg caggagccgg tgctccgcgg cgcctcccca acacgctgag gacgaagccc     360
ccgcacccct cccaacagga ccctgactgg gccctcagga tcgggggca ttcgggagag      420
gtcccgggag tcctgccctg tgtgtgtgtg ttgggggggc gttgcgtgca ggtgcccatc     480
gctggccggc gccgtcgagg gccaggccga ggctaaggga gcatcccctt ccttgccgga     540
ctcctctctc caccgcccgg ccccaggcct ctgggagcac tctcgccccg cgattcccgc     600
tccgagcttt cacagcgggc tcccttgcgc tggggctgag gacactctcc ggccggagac     660
tcccggtctg cggggaaggg ggtctggcgg gacccgtcgg ctggggtccc gctgagctcc     720
cggagtgggc tgcccggggg cccccagccc aagccgcgct cggctggcac caggggctag     780
ggtgcggcgg ggcggggcgg ggcggggcgg gcggccgggg aggtgatctc actcctccct     840
ccctctcctc cccggcgctc ccctccccg ccctgcgcg cacgcccgcc ccgcccgcc         900
acagccgctg ctgccgcagc atcggcatcg cagacgcgct cgggcggcgg gtccgaggcc     960
ggcgtgcgcg gaggctgggc gggcagcccg agcggtggcc gcagcgcagg taaggcgggc    1020
tggcctcccc gtgcgacccg ggccgcggcc gcgatccccc ggcgacacca caccgctctg    1080
cccggggtgc acgaccagg gagtcccggc ccggtccggc ccgcggtaac cggcgttgct     1140
gccggagccc cacccatgcc gggcgtcggg ctccgggcac cgcgggctgt aagcggggcg    1200
gggagggat gccgggtgcc cgagcccgac aggtgagggg taacctgcgg ggccccagat     1260
gctggcctgg gcgggagaac agggcggggg gcgtcaggca gggtctgtgt gggcaggcgg    1320
gggctgaagt tggcgggtcc ccgtgcgtgt gtgcgtgtct gagaaaggaa gccagatcgg    1380
gtcgagcgct cccccacagg ccgccgtggg gtgtggccct gggcgtggct gcccctcatc    1440
cccagccgag agctcagttt ggttgaaaat cccggctgac agcgtggtga ggggtagatc    1500
gggataagcc gcccctgcaa tgggggagg ggagtgaacg ggactgggcg ctgcctgccc     1560
ctccgcccca aggttggggg ggcttttgttc tcctccttct tctttccaaa tcccagcctg    1620
ggctcctccg ggctcacccg aaaacctgcc gcagagccag gggctcctcc ccggaggcgt    1680
agggcgcctc tggagcccgt ttccacaggc tctgtggcca gtcagggctg gagtgggtga    1740
ggtcggttcg ggcaccccact gctgtgcctc ccgtgcatgg gtgtccatca ggtagggtcc    1800
```

```
atcaggtagg ggtgagggaa ggtgggcctc actggctcag gcggtccctg cgcactgcag    1860
gtcttttgcc cactgccaca tcttcctatc tctgtgcggt tatgggaggg gtcagcgatt    1920
cctattccct ccattccagg tcagacttt ggggcctctt ggttggcagg gattgcaaag    1980
aacacgcact acaatccatt gcccccgaca gggtatctgg accccccacc tatcactgtc    2040
cctctcagga aggcaggcct agagccatct gccccttct ccagaaggag tgggggcctg    2100
gcacccccca ggtagatacc ctgcccctgt taacccacc ctgagggcag ggcatcggg     2160 gcagcccagt gccatctctg ctgactcatg tggccctgac gtaaatcagt gcagtccgcc    2220
cttcttcccc tggggctgc tgcccagcat catctttctg gggcggggc ctccccaggg     2280 cctctcccct cccgtcagct ccttgctgca ggtggtggga cttggcccag cctggcctct    2340
cccctggcac agctcccatg cagtgccac atgtgcacac ctgagggctc cagagccttt    2400
gaggactcgg ctgtcttggc cacatgggaa gtttggggca gggttgggcc tgggaccttc    2460
ccacctcctt ggctcctggt catttctctc tgctgcatct gagtctctct ccatatttat    2520
tgatgtttgt gtgtgtatga tcccgaaagt aatacatctt attgtaggac acttgaaata    2580
tacagaaaag aacaaaagaa attaagaatc gctagtgatc tgatcaccaa gagggaaaca    2640
cgttcagcac gccccagcct ccctggtttg ctacaccgcg ctcctaaaag gctcctcccc    2700
aagttcccag ctgccagctc cctgctgagc atcaggagga caatcagcgc ttcaaggtgg    2760
cggggtcccc tgccctgcag ccagtgaaga gcttccctac ccaggcgctc aggatcccag    2820
cgatgggcag tcgtgtactg ggcagctgct catggccagt gctcctttgg gccgggctct    2880
gggctgccca tggaagagcc agtgacaaac tggaccagca ttgtccctgt cttcgtgggg    2940
tgtcacttgt tttctttttt cttgatgatt atctgaaggg aaaagggagg caaagagtga    3000
ggaagggcct ggcctgaggg ctcctacagt gagcagggtg cccagattgt gcccccaatc    3060
ggcctctccc aggtccgagc cctttccacc actggaacta cagctggcgc cttccttggc    3120
atgcacctgg ccaggactgg caggtgaggg tcgaggagac aggcctgtgt gccctacctt    3180
gatcaccaag ttcccttca aagctcgaaa tggctgcact gagtgctttt ctgggtgtga    3240
gggtgatgcg gcctcgcaga gtggcccagg ctccaggagg gcacgttcat gggagaacct    3300
ggggtagtgg tggggtcctg tgaggaggtc tgccaggatg gggatcccag ccaagaccct    3360
ggtctgccag gcatgagtgg gggcatgagt gggggccctg cctccctccc tcgtggttca    3420
gacagtgggg gaggcggggg gtctggatgc ccttctaggg tccccagcag ggtgctcatt    3480
gccctgtcct ctgcccctgc aatgggctgg ggctgggtcc ctgggtgggg ccatctggaa    3540
tgggcctgca gcatccctgc ccctgcagtc gctgtcttac ttgctctgat ctggcccatc    3600
tcggacacct ccttctcctg cttccccgc cccctgctc tctcctctgc agcctcccac     3660
gtctccctgt gccccacccc cagggccatc accttcctcc tccttctagg cagaagcctg    3720
ctgctgccgg ggatggggtg caccactccc cgtctcctcc ctctgcctct gcctgctgg    3780 ccctcccttc cctcttcccc cttcccgtca gggctctgct ccatctctct gcttaccctt    3840
ttgtctgtct tccaccgctc tgctcctctc cttgtccccc ccagctgccc ctgcctcacc    3900
cttgagggcc ctgaggttgt gccctgtcca gcagccactc agcacccttc tgctggactc    3960
tacgccttgg ggttgggccc agaccccca tgggggcctt gtctgagtgg aaggctgtat    4020 gggggtgcc tggtgagcag cagccagacg agcactgggg gaggtagccc gcccagcttg    4080
cctcttcccc agatatcaac agggtctttg tggcttcctg aaggctgtgg ctggaaaaag    4140
agggaggagc tggggagggt ctggccgctg ttctttctag aagcttttct tgtccagtg     4200
```

```
gcccccagcc caggtccccg tgttcttccc aggttggaaa gctgcagagg gagtgcccag    4260
ccactgtcag tcagcagctc ctgctcatct ctggcccttta cacccagcag gggcagctgc   4320
gagggccagg ggttgggtgg ggcaggaggg tggcagcgtc ctgggctcca tgcacttggc    4380
caaagaggac ttctgaaccc gtccatccca gtgcgggtct gagagtggaa cttgagggaa    4440
agggactgag tcccgggagc ccctctgccc cctgccctcc agccaggcag acttcctatc    4500
tgcatgtatg gggtttgtgt ctctgcttgt gtgtgtgtat ttgtgtgtgt gtaacctcca    4560
gtattcctgt ttgtctgggt ggggtcatat atttggttgc atgtgtgtgt gtgttcgtga    4620
accagcatgc acacacatat tgtcatgagg ccacgtgggt ctcctcagat gccccaacag    4680
ggcctgtgct gggaaggggt ggggctgagg gtggctgctg cagtggctgg atgggacag     4740 agcctctggc caacccaggc tgtgcttcag tggaggggg ttccctgtgg ccctgtctcc     4800
cagccatctg cgtctgtgtt catgacttag gaatgcccaa gccctgggga tcacagaggc    4860
cccattgtcc gccccgggc ttcctgtgtc cccctctgcc ctttaacccc tcgggagtgg     4920
ggcccctgga gggggcccgt ggggcctggc agtgtctgag ctgtttccag gcaccccac     4980 cccgccccc gcaaaccaac acaggctagg tatcccagga ctgctgtggg ccagggcctc     5040
tccctgcccc aggctgggct ccttccctgc tctccttttc aggccacagc cccaggaact    5100
ggatgcagtc tgttccttct ggcctggccg ctgaagcccc ctctagtgct agggtcatcc    5160
tagctccctg aggaggcctg gggcctgaga ggagccctag ttttgctgcc acctcatttc    5220
tctcgccttc tagggggtctc                                               5240

<210> SEQ ID NO 2
<211> LENGTH: 4330
<212> TYPE: DNA
<213> ORGANISM: Homo sapiens

<400> SEQUENCE: 2
tcgtcttttt ccacgcacag cagcaataca atattaattt attctgattt aagattagaa      60
gtaaatagag ctagaactaa catttataat aacgatagaa tgcatttgct taaaacaaga    120
ttggcaattc ttcataataa tagacatta tacagatttg tatttatagt ttttttcttt    180
ttctgcatct acaggtttga cccttttatg catgtaactt cacagtataa aggaaatcca    240
aacaatgtct cccttctcta gtttattccg cttaccccag tcctcctagg cttctgtgaa    300
tttcagaaag caaaaacaaa caaaaaaaaa acttttgtt caaggcgatt taaaaaaca    360 acttcacaag atagggagaa ttgtggtgtg cttgtcacat gttaccagtg gtaacaattt    420
taatgacaaa aaaatccact aattccaaat gcataaacaa aactacatta tttatctaca    480
gccagaagga tatggaaatt tagaggtaaa tgaaacattt tagtcaggca atgtaagacc    540
ttacagaaac tggaagagaa gtccccttct cttggtaatt cttttttttt cttttttaaag   600 ctgggatatc ttacagagga aggaaaaatt aacctttttt actttctttc tcactttta    660 aatcagccaa agtcaagccc gtttgccaac ctgcatgtcc atgcctgtaa gcccttctct    720
tggccaagga agaaaggaag aaagaaaaaa gaaacccagg ggcctgtatc ccctgattaa    780
acacagcaca gcactccagg cagacatgcc cggtggcggc tcctttgcac cattgacctc    840
aggccagaca cctcagcgcc aacaatggga cctcggcctt ccggctaggt ttgccccagg    900
ctgggcagga aaccagctcg gccgaagaca ggggccattt cgagcagtgg accccaaga    960 cagcaaaccc agcccagtca ggacttgaca cttaggacaa tatctatctc tatagaattt   1020
```

-continued

```
tagcatgata tggcttttc ccccagaaaa caacaaataa accagcacca agcaaacaca    1080
aagaaacaaa aagtcagaac aaaccagccc tgcacagatg taacgggcca ggagatggcg    1140
agtgtgggag ggaggaacag ggctccagca caggtgcgag ttcctgggca gagcctgaag    1200
acagagggag gggaccagcg ctcgggaagt gaaaaaaccg cgtcgcctgg agattcatca    1260
ggaaaaatta aagttggctg tgagctcccg gatccggttt tctcgattca ttttcttcag    1320
tttcatcctg cggttctgaa accagatttt cacttgtctg tccgtgaggt ggacgctgcg    1380
gctaatctct aggcgccgct ctcgagtaag gtacatattg aacagaaact ccttctccag    1440
ctccagtgtc tggtgcttcg tgtaggggca gcgcttcttc cgaccactct ttgccgtgag    1500
ccagttggct gcgttttcac ctttggaatt gcctggcatg taagagaata aagagggat     1560 gattaagtcg aggccacacg ggctgcccgc ggggtgaat tgcctccgtt tctcccataa     1620
gagagatgtc ccaagtcaca gagaagagag tcgtgccccc gtttttggct tgctgagagc    1680
aagcagttcc tccaaaagtc atgacaaaaa ttgagtgggc cttcaatcta catgacccctt   1740 ccaatttaca tttcccccac ttttccaaac acctgtttta gcgctaagcc gtagatgctt    1800
gcagaaggaa aggcctggga gggcaggctg tacatcttga acttaacgct tttctttgcc    1860
tcttgccata tggcagacaa gcatttcctg tagcccccag gctaggagcg cggggtgctt    1920
acttggaaga tgggccaggc agcttggctg tctcacccca gggccctgat tgcccaagac    1980
tcgataaggg gagaaagaag ggcatcattg gtccaatggg gaaggcagga aaaccgatt    2040 cgggggtcaa gggccctccc tcaagtttct ccaggagcca gggatagata gctgggcgat   2100
tccgaggtcc aggggaaggg aaatggccct tctctggctc tcagctcagg gccccccgct   2160
tccaggccgg atttgccttt tcttcttccc gcaacgaaga ttcccgcccc tcagcaactt   2220 tgaaaaagc atgggggatc gtaaactcga acttcgccgg ttaatgggct tatttattgg    2280
cgctggcggc tgcttatttt ggatgcctta caaacatccg cgctatctgc gggcgagcta   2340
ctttccctcc ctcccctcc ccccgcgtgg gcgcgccgc gcaggctggg cagggaccag     2400
ggctctgggt cctcccggcc acaggaaaga gcgcacagga gggggcctgc tcgctggtgt   2460
cctcgtccct agtcaggggg agctgaggcc agcgccgagg acgtcttgct gtggggcgct   2520
aagccggaca tgaattttac tgcgtcccca cgcccaaata ttaaaaagca agttcacaag   2580
gtcagcctgc ctgcagcttg ggccaaggcc ggccggctgc tgcgcgggct cctagttttc   2640
tgatccttct cctccttgtg tctgcctgtc tgcccgcctg actgcagccc tctgcagccc   2700
tgcttaccca gggaatcctt ctccggcgag gctttgctgc tctcggaagg ggccggggag   2760
agctcctccg cggccgagga cgacgcgtgc gcctcctcgt cgccctgcga gccccccgccg  2820 ctgccgcaag ccagcgtggg gggcggcggc gaatcgaggg ctcgctccctt ccgggccgca  2880 tcggccgagc cggaggctag cgcgggcggg agatcgaaac cgcgccccgg gggctgcgcg   2940
gggaacgggc cagccccgag ttgctgcgcg ccgccgccgc cgctgccata gcccttggcg   3000
gtgccgtagg cctgagaaag gcggaagtag ccaggcactg gcaccccgct ggaggtgccc   3060
agggcgcagc cgtcgggcgg cgggccccgc gggaagggag ccagttcggc ggcggtggcc   3120
gagactttgg ggcatttgtc cgccgagtcg tagaggcagt aggagctctc ttctttgatg   3180
ttctgcgcga aagagcacga ggtggcctgc ggcgctggct ggggtggttg cggcggggc    3240 ggcggctgct gctggggcgg cggcggcggc ccgtcaggcg gctccatccg gcaagaccgg   3300
ggcgcgtcta gccacaggtc tatgggcgag ggcccgtagc cgtgcgcccc gggacctaga   3360
cccccgccac cgccaccgct gcccggcgac gctgcctcat tgcgcttgcc gcccagcgtg   3420
```

```
gggaagagcc cgcagctctg cagcccgtag ggcaggtcgg cggcgggcgg caggtagacc    3480
ccgccgtggg cgtagtaacc gccaccgccg ccgccccccg cgccaccacc accgccgcct    3540
gcctcgcctc tgcccgagct gatgagcgag tcgaccaaaa aagagttcgc ggcggggctc    3600
tccgagcatg acattgttgt gggataattt ggcgaaggga gcagatagcc ctttctggct    3660
gacatttctt gtgcaaaaca tgctgaatac gattagcaat ccccccgcac cgcggcgggc    3720
gcccgcagcc aatcccgagc cagagtttcc gcgcgaccac tcccagtttg gtttcgtagg    3780
cgcggggccg ctctccgagg gcgccctcag agcccgcgat tgatataaat atgtaatctg    3840
tattgatggg ccaggagacg caccccgaca ccttggcccg aaggccggga gctgtggggg    3900
ctgccccaac gtggctggtg gggggcctgg ccattgggct cgccccgccc tacccggac    3960 gtgagcccca taccggggtc ccttagaagg gcccttgggc cccgcgcagt taacaagtgg    4020
ggtgtttatg gtgcgcgccc agtctgcctt gggtgctcac catccctgtc gcagaagctg    4080
ccactagtcc ccggtgtact ctaaccactg aagcggccgt gtcggggact cacgcgcttc    4140
ccattcagct ctggatctgg aactggcccc ttgtctgaat tctgcctcct caaaagtggc    4200
gaacctggcc ctatggccgt caggatcctc agagtgtcag gagcccagag tgaactagaa    4260
gctgacttgc ctctacttcc agtatccaca gattttccc caaaatgcag tggttgttcc    4320
ctagccccta                                                           4330

<210> SEQ ID NO 3
<211> LENGTH: 4661
<212> TYPE: DNA
<213> ORGANISM: Homo sapiens

<400> SEQUENCE: 3
ggttgccact ctcaatctcg aactagtttt tttctctttt aagggttgta tccataatgc      60
aaaaatggaa agaattaaaa agcacacgca aaacatgatt ctcgggattt ttctctattt     120
ttatggttga ctaattcaaa cagaaagaca catccaagag aaaattgcta agtttgatac     180
aagttatgaa acttgtgaag cccaagtact gcctggggat gaatttaact tgtatgacag     240
gtgcagagct gtcgctttca gacatcttaa gaaacacgga gttattttga atgactttct     300
ctcggtcaca agggagccac caacgtctcc acagtgaaac caactggctg gctgaaggaa     360
cagaaatcct ctgctccgcc tactgggat taggagctga gggcagtggt gaacattccc     420
aaaatattag ccttggcttt actggacatc cagcgagcag tgcagccagc attcctggcg     480
gctccctggc ccagtctctg gcgcatgcgt cctagcatct ttgggcaggc ttccccgccc     540
tcgtgacgcg tcggcccggg cctggcctcc cggcgatcac agcggacagg gggcggagcc     600 taaggggtg gggagacgcc ggcccttgg cccagctgaa acggaattc tttgccggct     660 ggctccccac tctgccagag cgaggcgggg cagtgaggac tccgcgacgc gtccgcaccc     720 tgcgccaga gcggctttga gctcggctgc gtccgcgcta ggcgcttttt cccagaagca     780
atccaggcgc gcccgctggt tcttgagcgc caggaaaagc ccggagctaa cgaccggccg     840
ctcggccact gcacgggcc ccaagccgca aaggacgac gggagggtaa tgaagctgag     900
cccaggtctc ctaggaagga gagagtgcgc cggagcagcg tggaaagaa gggaagagtg     960 tcgttaagtt tacggccaac ggtggattat ccgggccgct gcgcgtctgg gggctgcgga    1020
atgcgcgagg agaacaaggg catgcccagt ggggcggca gcgatgaggg tctggccagc    1080
gccgcggcgc ggggactagt ggagaaggtg cgacagctcc tggaagccgg cgcggatccc    1140
```

-continued

```
aacggagtca accgtttcgg gaggcgcgcg atccaggtag ctggggcccc agggcctcgc    1200
cggcaggggg cgcgcgaacg cggggcgcgg cctcggcgga tcgggctgg aacctagatc     1260 gccgatgtag atttgtacag gagtctccgt tggccggagg tgtgcattcc acgcgtaaaa    1320
caggctttta cccagcaaaa atcctaaaga gagacattga aaacccact gtttaagctt     1380 tttttagtgg ttttttgttct gccatctcat gatcagagat gcaaggaata gactgaattg   1440
gggagaaaag gagaaaagga aagcttattt agggaagaag attatcttgt ctgtctgctt    1500
tcaacgataa agataagtaa agtataagtt acgcattcta gattggattt aaggaattct    1560
acaaaatcat agtacatgga aaaaatcaat gtaaacttct aagctactat atgaaatctg    1620
ttgtattgtt ttctcataga ggttaattga gaatgagacg ggattcctca accacagtac    1680
ttagttcctt ttatgttagc agtgtcttat gagtgatgca taagagaaaa aatatatagt    1740
tctataggtt tctcattctt taattatcat actcagtgcc cagattacaa aaatattcct    1800
gcagcaactg ttaggtcctt tttgaatggc aaaggatctt cataaataat gcatctttat    1860
cttcattgtt aaaatacact tattcaatgt ttaagtacga atcctgcttt aattagtact    1920
gatatttttt atttcttta caatctcgga caactctttt gtactttacc gttggctagt     1980
ggtcatattc agtactcacc tcactatcac cctctaaaac taagctaata ttaagggatc    2040
ttgttaatag tatagatttt aaagaagtgt tcatttcttt tgaattctta gaataatggt    2100
ataacaaatg agggattttt aaaggagcaa aaatattgta aagtgcatct taaaacttaa    2160 aaatttatt ataattata aaaacaagtt atatatgtaa ttcaccattt tctgaaatac      2220
taacagcagc tattttcccc ttttttttcta tgtaaaatat ccttacatca ctagtagata   2280
taacttatca cggttttttaa gagatgaaat gaacatttct aatattaatg aaacaagcca   2340
acaaaacatg agaagtatac tgcctttcaa ttaaatggta tattttaaag tgcataaacc    2400
cataacaaat aactcgattt tagacattta gttaccaaaa attgtcttat aattgacttt    2460
aaatatgaca gcaaatgttt tcataatgtt catgtacaca aatggctgct acaggattac    2520
tcctgcaaaa catcattttt tctaagttat gcatcatcct gattgactgc taacatccaa    2580
gctctattta tttatttatt tattttattt tttttgagat gaggcctcac tctgtcggac    2640
aggctggagt gcagtggcac aatctcagct cactgcaacc tcttccagga tgcaagcgat    2700
tctcctgcct cagcctcctg agttgctggg actacaggca cgccccacca tgcccagcta    2760 atttttttatt ttttgtagta gagacgggat ttcaccatgt tggccaggct ggtctcgaac    2820
tcctgacctc aggtgatctg cctgctatgg cctcccaaag tgctgggatt acaggcataa    2880
gccactgggc ctggcccaag ctcttttat atagcaaaat atttactgtt taacattttt     2940
aaatcttagc tattataaaa tcctgtagta tacaaatata gttagtttta tattcatta     3000 aaaatattat agtctaaatt taaaatgatg aactgttaag gaaaaatcat ttattataat    3060
tttataagat tttgcatgat ttaatttact tttcccttct aatctccaac tttggctcaa    3120
attatcacac tacaagccag ttatgagctc agacacatga caaacaaaag ccttccgcac    3180
gggatttgct atgagaacta aataaattaa aaaaaaaga aagaaaaaaa cttagttgtt     3240
tattttctcc cctaaaccat tactcccaac ttctaacaaa cagtagttga ctacctaata    3300
aatatttgta gacctggatt atggaggagg ggtcagcaag gcaaataatt taaaacttta    3360
aaagccgaat aaatttaact ctgcccctaa atcatttaac aaaatagatt cccatgttcc    3420
aatgaaaatc aagattgtt tttccataat gatgatcatc actttaccat caactttctt    3480
gtctctgcac gtttagagaa taaaatggca tttaatttgt actgagtata acctgaaggt    3540
```

```
ggggtgggaa agtggattgc atcagcaaat gaagaaacac cagacatcag agacctgaac    3600
acctctgcac tgggtgaaaa ctttgcaatt aggtgtttct ttaaatggct ccacctgcct    3660
tgccccggcc ggcatctccc atacctgccc ccaccctggc tctgaccact ctgctctctc    3720
tggcaggtca tgatgatggg cagcgcccgc gtggcggagc tgctgctgct ccacggcgcg    3780
gagcccaact gcgcagaccc tgccactctc acccgaccgg tgcatgatgc tgcccgggag    3840
ggcttcctgg acacgctggt ggtgctgcac cgggccgggg cgcggctgga cgtgcgcgat    3900
gcctggggtc gtctgcccgt ggacttggcc gaggagcggg gccaccgcga cgttgcaggg    3960
tacctgcgca cagccacggg ggactgacgc caggttcccc agccgcccac aacgacttta    4020
ttttcttacc caatttccca cccccaccca cctaattcga tgaaggctgc caacggggag    4080
cggcggaaag cctgtaagcc tgcaagcctg tctgagactc acaggaagga ggagccgacc    4140
gggaataacc ttccatacat tttttttcttt gtcttatctg gccctcgaca ctcaccatga    4200
agcgaaacac agagaagcgg atttccaggg atatttagga gtgtgtgaca ttccaggggt    4260
cgtttgcttt tcagggtttt ctgagggaaa gtgcatatga aatccttgac tggacctggt    4320
ggctacgaat cttccgatgg atgaatctcc cactccagcg ctgagtggga gaaggcagtg    4380
attagcactt gggtgacggc agtcgatgcg ttcactccaa tgtctgctga ggagttatgg    4440
tgaacccaca acttaggccc tagcggcaga aaggaaaacc tgaagactga ggacaaagtg    4500
gaggagggcc gaggtgggct tcagtaagtc cccggcggcg ctttagtttg agcgcatggc    4560
aagtcacatg cgtaaacgac actctctgga agccctggag accctcgccc aactccacca    4620
gatagcagag gggtaagaga ggatgtgcaa gcgacgacag a                        4661
```

METHODS OF DETECTING MODIFIED AND UNMODIFIED DNA

CROSS REFERENCE TO RELATED APPLICATIONS

This application is a National Phase of PCT Patent Application No. PCT/IL2018/050854 having International filing date of Jul. 31, 2018, which claims the benefit of priority of U.S. Provisional Patent Application No. 62/538,881, filed Jul. 31, 2017, the contents of which are incorporated herein by reference in their entirety.

FIELD OF INVENTION

The present invention is in the field of DNA modification detection.

BACKGROUND OF THE INVENTION

In the human genome about 60%-80% of all cytosine-guanine dinucleotides (CpGs) are methylated. Methylation state plays extremely important roles in regulation of gene expression. Specifically, aberrant DNA methylation levels have been associated with various types of cancers, where tumor suppressor genes, such as p53, are hypermethylated, leading to gene silencing, while many oncogenes are hypomethylated to promote their over expression. Moreover, large cell-to-cell variations in methylation patterns indicate that intratumoral heterogeneity plays a critical role in tumor progression, while highly complicating bulk analysis of methylation patterns. Despite the growing evidence supporting the need for quantification of DNA methylation patterns, the availability of quantitative methods for sensing these genomic modifications, particularly at the single-molecule level, has remained to date limited. Unlike the DNA primary sequence, chemical DNA modifications are not preserved in DNA amplification, complicating sensing of epigenetic markers. Furthermore, bulk sensing methods often require averaging across thousands of DNA fragments—a process that limits the ability to detect heterogeneity within tumors. To overcome these limitations and enable simple and efficient single-cell epigenetic profiling, single molecule sensing technologies have been recently developed, such as single molecule real time (SMRT) sequencing, although this method involves large and expansive instrumentation.

Nanopores (NPs) represent an emerging single-molecule analysis technique capable of probing the structure of complex biological molecules and their interactions with other biomolecules. In the nanopore system an electrical field is used to mobilize an electrically charged biopolymer towards and through a nanoscale aperture. When the biopolymer is threaded through the pore it blocks a fraction of the ionic current that flows through it, resulting in an ion-current blockade event. Since the molecules are threaded in a single-file manner, this method enables direct scanning of useful molecular features along long biopolymers. For example, engineered protein nanopores, such as the MspA channel, have been developed for direct DNA sequencing of long DNA strands. Furthermore, solid-state NPs (ssNPs) have been fabricated with sub-nanometer precision to match the size (the cross-section) of many target analytes, enabling additional biosensing applications such as DNA barcoding of pathogens, mapping binding of transcription factors to their DNA targets and for label-free identification of single nucleotides, to name but a few. To detect epigenetic biomarkers including 5-methylcytosine (5 mC) or 5-hydroxymethylcytosine (5 hmC), bulky groups, such as methyl-CpG-binding domain (MBD) proteins or streptavidin, were conjugated to the DNA in order to produce an observable ion-current blockade on top of the blockade level of the bare DNA. This method is appealing in its simplicity but may not be used to probe densely methylated regions in the genome, due to the bulkiness of the conjugated proteins. Furthermore, to date direct NP quantification of un-methylated 5-methylcytosine sites has not been reported.

Detection of epigenetic markers, including 5-methylcytosine, is crucial due to their role in gene expression regulation, and due to the mounting evidence of aberrant DNA methylation patterns in cancer biogenesis. Single-molecule methods to date have primarily been focused on hypermethylation detection; however, many oncogenes are hypomethylated during cancer development, presenting an important unmet bio-sensing challenge. A simple method of detecting unmethylated CpGs in dense regions of methylated and unmethylated DNA is thus greatly needed.

SUMMARY OF THE INVENTION

The present invention provides methods of detecting the presence of a target modified DNA sequence or a target unmodified DNA sequence. Kits for doing same are also provided. The invention is at least partially based on the surprising finding that target DNA sequences corresponding to the binding sites of DNA methyltransferases (MTases), can be marked by a synthetic version of the MTases natural cofactor, and detection of this cofactor via nanopore technology can determine the presence of the target DNA sequence in DNA molecule. This method is enhanced by the fact that modification specific MTases can be employed, and thus the depositing of the cofactor on the target DNA sequence indicates that the modification, or lack of modification, specific to the MTase is present. This method can also determine the number of target sequences are present in the molecule, such as might be desired if the DNA molecule comprises repeating sequences.

Nanopore sensing technology is particularly well suited for this method because the nanopore allows for coupling the detection of the molecule itself and the detection of the cofactor simultaneously. The molecule partially blocks ion flow though the nanopore which is electrically detected, this allows for precise measuring of the dwell time of the molecule and thus the molecules length. At the same time the cofactors presence can be measured, either via electrical or optical sensing, and the exact number of cofactors on the molecule (whose length is known) can be determined. This system also can be multiplexed, with multiple enzymes and multiple cofactors, providing robust data concerning the sequences and their modification in analyzed DNA. Nanopores allow for easy multiplexing and rapid analysis of large numbers of molecules.

According to a first aspect, there is provided a method of detecting the presence of at least one target modified or unmodified DNA sequence in a DNA molecule, the method comprising:

a. contacting the DNA molecule with at least one DNA methyltransferase enzyme (MTase) in the presence of a synthetic cofactor of the MTase, wherein the enzyme differentially binds and deposits at least a detectable moiety from the synthetic cofactor on the target sequence depending on the presence of the modification, b. passing the contacted DNA molecule through a nanopore of an apparatus comprising a nanopore, and an electrical sensor, wherein the electrical sensor is configured to detect ion flow through the nanopore, and wherein the detectable moiety is detectable as it passes through the nanopore; and c. detecting the DNA molecule as it passes through the nanopore and detecting if the detectable moiety is present as the DNA molecule passes through the nanopore, wherein the enzyme binds and deposits on modified DNA and the presence of the detectable moiety indicates the presence of the target modified DNA sequence or the enzyme binds and deposits on unmodified DNA and the presence of the detectable moiety indicates the presence of the target unmodified DNA sequence;

thereby detecting the presence of at least one target DNA sequence with or without a modification.

According to another aspect, there is provided a kit comprising:

a. at least one DNA methyltransferase enzyme (MTase);

b. at least one synthetic cofactor of the MTase comprising a detectable moiety; and c. a nanopore apparatus comprising a nanopore, and an electrical sensor, wherein the electrical sensor is configured to detect ion flow through the nanopore;

wherein the detectable moiety is detectable as it translocates through the nanopore.

According to some embodiments, the synthetic cofactor is a steric S-adenosyl-L-methionine (AdoMet) analog.

According to some embodiments, the synthetic cofactor comprises a bulky group. According to some embodiments, the bulky group is gamma cyclodextrin.

According to some embodiments, the synthetic cofactor comprises a fluorophore, and the apparatus comprises an optical sensor, wherein the optical sensor is configured to detect fluorescence at the nanopore. According to some embodiments, the fluorophore is selected from a red fluorophore, an orange fluorophore, a green fluorophore and a blue fluorophore.

According to some embodiments, the detecting if the detectable moiety is present comprises determining the fluorescence per base pair of the molecule. According to some embodiments, the detecting if the detectable moiety is present comprises detecting fluorescence before the molecule translocates through the nanopore, after the molecule translocates through the nanopore or both, and removing background fluorescence from fluorescence measured as the molecule translocates through the nanopore.

According to some embodiments, the DNA modification is DNA methylation. According to some embodiments, the DNA methylation is selected from 5-methylcytosine and 5-hydroxymethylcytosine.

According to some embodiments, the enzyme binds to and transfers the detectable moiety to only modified or only unmodified target sequence.

According to some embodiments, the enzyme binds to a target sequence comprising a cytosine-guanine dinucleotide (CpG).

According to some embodiments, the enzyme is selected from M.TaqI, M.SssI, M.BscCI, M.EcoDam, M.HhaI, and MpeI. According to some embodiments, the MTase is M.TaqI and the method detects unmethylated target sequence.

According to some embodiments, the methods of the invention are for detecting a modified or unmodified target sequence, wherein the target sequence is within 5 base pairs of a differently modified target sequence.

According to some embodiments, the depositing comprising covalent linkage of the detectable moiety to the DNA molecule.

According to some embodiments, the apparatus comprises a first fluid reservoir and a second fluid reservoir and wherein the first and second fluid reservoirs are in electrical contact with each other via the nanopore.

According to some embodiments, the passing comprises running electrical current from the first reservoir to the second reservoir via the nanopore and wherein the first and second reservoirs contain fluid suitable for transferring the DNA molecule through the nanopore via the electrical current. According to some embodiments, the DNA molecule is within a solution, and wherein the passing comprises placing the solution in the first reservoir.

According to some embodiments, the methods of the invention further comprise removing from the solution synthetic cofactor that is not deposited on DNA before the placing.

According to some embodiments, the nanopore apparatus further comprises an optical sensor configured to detect fluorescence at the nanopore.

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE INVENTION

Figure 1A:
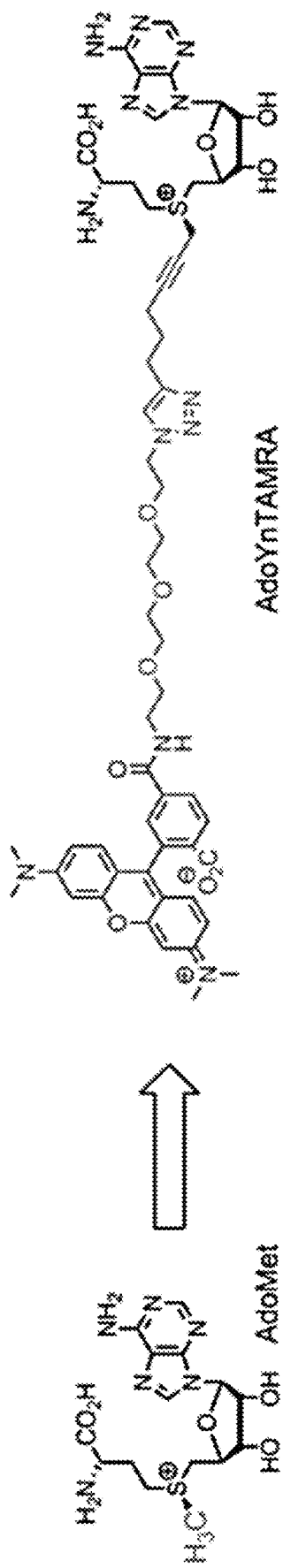
FIGS. 1A-E: A one-step enzymatic method coupled to electro-optical nanopore sensing for quantification of DNA methylation at the single molecule level. (1A) Diagram of M.TaqI catalyzing the transfer of the extended side chain from the synthetic cofactor analogue AdoYnTAMRA to the amino group of adenine with the double stranded 5'-TCGA-3' DNA sequence leading to fluorescently labeled DNA and the cofactor product S-adenosyl-l-homocystein. (1B) A schematic illustration of our method. Double-stranded DNA is reacted with DNA MTase and custom made AdoMet analogues equipped with a fluorescent moiety. The labeled DNA molecules are then analyzed one by one using a nanopore device. (1C) The DNA readout process involves threading of the linearized DNA through a solid-state nanopore roughly 4 nm in diameter as shown in the TEM micrograph (inset). (1D) Line graph showing the nanopore ion current and the fluorescence emissions are interrogated simultaneously. Entries of labeled 10 kbp DNA molecules are recorded as simultaneous downwards spike in the ion current and upwards photon bursts, as shown in the lower panel. Photon spikes not associated with DNA translocations are readily observed and rejected (lower line marked with an asterisk). (1E) Line graph showing the nanopore ion current and the fluorescence emissions interrogated simultaneously for the 5 kbp DNA labeled with M.TaqI and AdoYnCF640R.
Figure 1A:
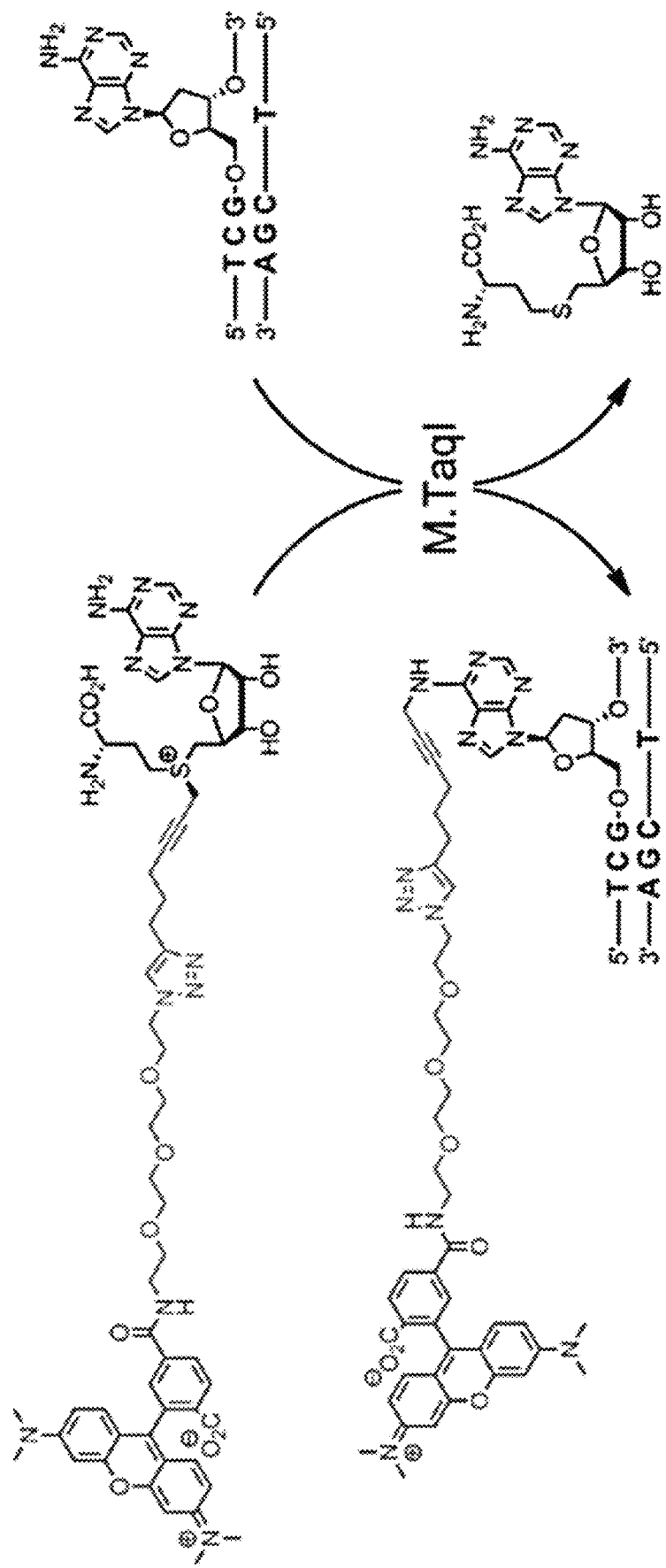

The present invention, in some embodiments, provides methods of treating . . . . The present invention further concerns a method of treating . . . . A kit comprising . . . is also provided.

To enable hypomethylation quantification we have developed an electro-optical ssNP sensing method to probe unmethylated CpG sites in kilobase long double-stranded DNA (dsDNA) molecules. Single molecule fluorescence sensing can substantially expand the range of NP sensing applications while offering a highly parallel platform with broad signal bandwidth.21-26 Recently, single-molecule fluorescence sensing has been employed for the detection of short, self-quenched molecular beacons threaded through a ssNP.27 In the current study, we have employed electro-optical sensing in ssNPs to directly detect sequence-specific methylation in long DNAs. Moreover, we show that the emitted photons intensity just before and after the passage of each DNA molecule through the ssNP, quantitatively correlates with the number of unmethylated CpGs in the DNA target, regardless of the NP size or the actual dwell time of each molecule in the NP device.

Our method involves a one-step enzymatic reaction, using DNA methyltransferases (MTases) with small molecular weight synthetic cofactors to directly conjugate fluorescent probes to unmethylated CpG sites. An ultra-sensitive electro-optical nanopore sensing tool, which permits single fluorophore, multi-color quantification is then applied to produce highly quantitative single-molecule fluorescence measurements. In our system two independent, time-resolved measurements take place simultaneously during the threading and passage of each DNA molecules through a ssNP: i) an electrical ion current measurement, acting as a gate signal which reports the dwell-time of each DNA molecules in the pore, regardless if it is labeled or not, and ii) a high-sensitivity single molecule fluorescence readout for single or multiple colors, which is used to quantify the un-methylated CpG sites in specific DNA recognition sequences. Notably, our method is generalizable to many DNA MTases targeting multiple specific sequences, each coupled to its own color-encoded probe.

By a first aspect, there is provided a method of detecting the presence of at least one target modified DNA sequence in a DNA molecule, the method comprising:
  a. contacting the DNA molecule with at least one DNA methyltransferase enzyme (MTase) in the presence of a synthetic cofactor orthogonal to the MTase, wherein the enzyme binds and deposits at least a detectable moiety from the synthetic cofactor on the target sequence when the target sequence is modified,
  b. passing the contacted DNA molecule through a nanopore of an apparatus comprising a nanopore, and an electrical sensor, wherein the electrical sensor is configured to detect ion flow through the nanopore, and wherein the detectable moiety is detectable as it passes through the nanopore; and
  c. detecting the DNA molecule as it passes through the nanopore and detecting if the detectable moiety is present as the DNA molecule passes through the nanopore, wherein presence of the detectable moiety indicates the presence of the target modified DNA sequence in the DNA molecule;
    thereby detecting the presence of at least one target modified DNA sequence in a DNA molecule.

According to another aspect, there is provided a method of detecting the presence of at least one target unmodified DNA sequence in a DNA molecule, the method comprising:
  a. contacting the DNA molecule with at least one DNA methyltransferase enzyme (MTase) in the presence of a synthetic cofactor orthogonal to the MTase, wherein the enzyme binds and deposits at least a detectable moiety from the synthetic cofactor on the target sequence when the target sequence is unmodified,
  b. passing the contacted DNA molecule through a nanopore of an apparatus comprising a nanopore, and an electrical sensor, wherein the electrical sensor is configured to detect ion flow through the nanopore, and wherein the detectable moiety is detectable as it passes through the nanopore; and
  c. detecting the DNA molecule as it passes through the nanopore and detecting if the detectable moiety is present as the DNA molecule passes through the nanopore, wherein presence of the detectable moiety indicates the presence of the target unmodified DNA sequence in the DNA molecule;
    thereby detecting the presence of at least one target unmodified DNA sequence in a DNA molecule.

In some embodiments, the method of the invention differentiates between a modified and an unmodified sequence. In some embodiments, the method of the invention quantifies the number of the target sequence with or without the modification in the DNA molecule. A skilled artisan will appreciate that selection of the MTase will determine what sequence and what modification are investigated. Each MTase will bind to a target sequence, and the binding will be dependent on the modification status. Some MTases will bind only if the DNA is unmodified. Some MTases will bind only if the DNA is modified. This provides specificity for the assay. The modification need not be on the base pair to which the MTase attaches the cofactor. Indeed, the modification may be on a different base, but still block MTase binding and deposition.

In some embodiments, one target sequence is detected. In some embodiments, a plurality of target sequences is detected. In some embodiments, at least 1, 2, 3, 4, 5, 6, 7, 8, 9 or 10 target sequences are detected. Each possibility represents a separate embodiment of the invention. In some embodiments, the same target sequence is bound by at least two different enzymes, but each enzyme is sensitive to a different modification or lack of modification. For instance, one enzyme may bind the sequence only when modified and another enzyme may bind the same sequence but only when unmodified.

In some embodiments, the target sequence occurs at least once in the DNA molecule. In some embodiments, the target sequence occurs once in the DNA molecule. In some embodiments, the DNA molecule comprises a plurality of the target sequence. In some embodiments, the target sequence is repeated in the DNA molecule. In some embodiments, the repeats are sequential. In some embodiments, the repeats are one after another. In some embodiments, the repeats are separated by intervening sequence. In some embodiments, the repeats are within a CpG island. In some embodiments, the method of the invention can differentiate between adjacent repeats of the target sequence that are differentially modified. In some embodiments, the method can detect a modified or unmodified target sequence, wherein the target sequence is adjacent to a differently modified target sequence. In some embodiments, the method can detect a modified or unmodified target sequence, wherein the target sequence is within 1, 2, 3, 4, 5, 6, 7, 8, 9 or 10 base pairs of a differently modified target sequence. In some embodiments, the difference is modification is between modified and unmodified. In some embodiments, the difference in modification is between one modification and another modification. In some embodiments, the difference in modification is between modification of one base of the sequence and another base of the sequence.

In some embodiments, the DNA modification is DNA methylation. In some embodiments, the DNA methylation is selected from 5-methylcytosine and 5-hydroxymethylcytosine. In some embodiments, the DNA methylation is adenine methylation. In some embodiments, the methylation is cytosine-guanine dinucleotide (CpG) methylation. In some embodiments, the methylation is non-CpG methylation.

In some embodiments, the DNA molecule is contacted within conditions sufficient to allow binding of the MTase and transfer of the detectable moiety to the target sequence. In some embodiments, the contacting is done in the absence of the natural cofactor. In some embodiments, the contacted in done in a solution. In some embodiments, the solution is devoid of the natural cofactor. In some embodiments, the solution is configured to allow transfer of the detectable moiety to the target sequence. Such conditions are described herein. In some embodiments, the conditions are those described herein in the "Sample preparation and validation" section. The conditions may comprise a salt buffer, that may optionally have any one of KOAc, Tris-HOAc, $MgOAc_2$, a blocking agent and a detergent. The detergent may be for example DTT or Triton-X or Tween. The blocking agent may be for example BSA or another non-specific protein. In some embodiments, the conditions are devoid of the natural cofactor. In some embodiments, the contacting is at room temperature. In some embodiments, the contacting is at 4 degrees Celsius. In some embodiments, the contacting is at 37 degrees Celsius. In some embodiments the passing comprises placing the solution in a reservoir of the apparatus. In some embodiments, the reservoir is the first reservoir.

In some embodiments, the conditions for binding and transfer are not suitable for nanopore apparatus running. In some embodiments, the methods further require a buffer change. In some embodiments, the binding and transfer are performed at low salt concentrations and translocation through the nanopore is at high salt concentrations. In some embodiments low salt concentration is about 10 mM. In some embodiments low salt concentration is equal to or below 1, 0.9, 0.8, 0.7, 0.6, 0.5, 0.4, 0.3, 0.2, 0.1, 0.09, 0.08, 0.07, 0.06, 0.05, 0.04, 0.3, 0.02 or 0.01 M. Each possibility represents a separate embodiment of the invention. In some embodiments low salt concentration is between 1 and 500, 1 and 400, 1 and 300, 1 and 200, 1 and 100, 1 and 50, 1 and 40, 1 and 30, 1 and 20, 1 and 15, 1 and 10, 2 and 500, 2 and 400, 2 and 300, 2 and 200, 2 and 100, 2 and 50, 2 and 40, 2 and 30, 2 and 20, 2 and 15, 2 and 10, 3 and 500, 3 and 400, 3 and 300, 3 and 200, 3 and 100, 3 and 50, 3 and 40, 3 and 30, 3 and 20, 3 and 15, 3 and 10, 5 and 500, 5 and 400, 5 and 300, 5 and 200, 5 and 100, 5 and 50, 5 and 40, 5 and 30, 5 and 20, 5 and 15, or 5 and 10 mM. Each possibility represents a separate embodiment of the invention. In some embodiments, high salt concentration is about 1M. In some embodiments, high salt concentration is equal to or above 300, 400, 500, 600, 700, 800, 900 or 1000 mM. Each possibility represents a separate embodiment of the invention. In some embodiments, high salt concentration is between 300-2000, 300-1500, 300-1250, 300-1000, 500-2000, 500-1500, 500-1250, 500-1000, 600-2000, 600-1500, 600-1250, 600-1000, 700-2000, 700-1500, 700-1250, 700-1000, 800-2000, 800-1500, 800-1250, 800-1000, 900-2000, 900-1500, 900-1250, or 900-1000 mM. Each possibility represents a separate embodiment of the invention. In some embodiments, the same buffer is used for binding/transfer and for nanopore translocation. In some embodiments, solution in which the binding/transfer is performed is placed in the solution in a reservoir of the apparatus, thus increasing the salt concentration such that the nanopore apparatus operates optimally.

In some embodiments, the natural cofactor is S-adenosyl-L-methionine (AdoMet). In some embodiments, the synthetic cofactor is an AdoMet analog or derivative. In some embodiments, the analog or derivative comprises a detectable moiety. The moiety is detectable as it passes through the nanopore. The term "analog" as used herein, refers to a molecule that is similar, but not identical, to the AdoMet but that can still be a substrate for transferred by an MTase. An analog may have deletions or mutations. It should be understood, that all analogs of AdoMet that can still be a substrate for transferred and that comprise a detectable moiety may be used. Further, an analog may be analogous to a fragment of AdoMet coupled to a detectable moiety. In some embodiments, the analog comprises a detectable moiety.

The term "derivative" as used herein, refers to any molecule that is based off AdoMet, but can still be a substrate for transfer by the MTase. A derivative is not merely a fragment of the molecule, rather it may have additional modification made to the molecule. Further, a derivative may be a derivative of a fragment of the polypeptide of the invention. The derivative may be AdoMet coupled to a detectable moiety.

In some embodiments, the analog or derivative comprises side chains instead of a methyl group. In some embodiments, the side chains are unsaturated. In some embodiments, the analog or derivative comprises a triple bond within the transferred chain, next to the reactive carbon. In some embodiments, a side chain is coupled to a detectable moiety.

The term "moiety", as used herein, relates to a part of a molecule that may include either whole functional groups or parts of functional groups as substructures. The term "moiety" further means part of a molecule that exhibits a particular set of chemical and/or pharmacologic characteristics which are similar to the corresponding molecule. Thus, a detectable moiety has the characteristic of being able to be detected by the apparatus. In some embodiments, the detectable moiety is transferred/deposited by the same mechanism and in the same way as a methyl group would be transferred/deposited by the MTase.

In some embodiments, synthetic cofactor comprises a detectable moiety. In some embodiments, the detectable moiety is electrically detectable as it passes through the nanopore. In some embodiments, the electrically detectable moiety is a bulky group. In some embodiments, the detectable moiety is optically detectable. In some embodiments, the optically detectable moiety is a fluorophore. In embodiments in which the detectable moiety is optically detectable the apparatus further comprises an optical sensor. In some embodiments, the optical sensor is configured to detect fluorescence at the nanopore.

As used herein, the term "bulky group" refer to side chains on a molecule that hinder at least one of rotation, interaction or movement of the molecule. Bulky groups for nanopore identification are well known in the art. In some embodiments, the bulky group comprises a sugar ring. In some embodiments, the sugar ring is a glucose ring. In some embodiments, the glucose ring is cyclodextrin. In some embodiments, the bulky group is gamma cyclodextrin. In some embodiments, the bulky group is sufficiently big to alter ion flow through the nanopore, but not so big that it cannot pass through the nanopore. This will depend on the diameter of the nanopore, and the skilled artisan will choose the bulky group appropriately. In some embodiments, the bulky group has a diameter of less than 10, 9, 8, 7, 6, 5, 4, 3 or 2 nm. Each possibility represents a separate embodiment of the invention. In some embodiments, the bulky group has a diameter of less than 2 nm. In some embodiments, the bulky group has a diameter of between 10-1, 9-1, 8-1, 7-1, 6-1, 5-1, 4-1, 3-1, 2-1, 10-2, 9-2, 8-2, 7-2, 6-2, 5-2, 4-2, 3-2, 10-3, 9-3, 8-3, 7-3, 6-3, 5-3 or 4-3 nm. Each possibility represents a separate embodiment of the invention. In some embodiments, the bulky group produces a distinctive ion current blockade as it passes through the nanopore. A skilled artisan can distinguish this blockade from the blockade of the bare DNA.

In some embodiments, the fluorophore is a fluorochrome. In some embodiments, the fluorophore is selected from a blue fluorophore, a red fluorophore, an orange fluorophore and a green fluorophore. In some embodiments, the fluorophore is selected from a red fluorophore, an orange fluorophore and a green fluorophore. In some embodiments, the fluorophore is selected from a red fluorophore, and an orange fluorophore. In some embodiments, the fluorophore is selected from a red fluorophore, and a green fluorophore. In some embodiments, the fluorophore is selected from a red fluorophore, and a green fluorophore. In some embodiments, the fluorophore is detectable by a fluorescent microscope. In some embodiments, the fluorophore is suitable for nanopore detection. In some embodiments, the fluorophore is selected from TAMARA and CF640R. In some embodiments, the fluorophore is selected from TAMARA, CF640R and Atto488. Any other fluorophores known in the art may be used, including but not limited to GFP, YFP, CFP, Cy5, Cy7, and APC. In some embodiments, the fluorophore is a molecular beacon.

In some embodiments, the synthetic cofactor is orthogonal to the MTase. The synthetic cofactor corresponds to a given MTase and is a substrate for transfer of the detectable moiety to the target sequence if the MTase binds the target sequence. In some embodiments, free synthetic cofactor is removed before the passing. If the DNA molecule is in solution it can be isolated, such as by ethanol precipitation or filtration, and then passed through the nanopore. Due to the ability to detect ion flow changes when the DNA molecule passes through the nanopore and to measure dwell time, it is not essential to remove the synthetic cofactor as false readings can be removed from the data.

In some embodiments, the enzyme binds to and transfers the detectable moiety to only modified target sequence. In some embodiments, the enzyme binds to and transfers the detectable moiety to only unmodified target sequence. In some embodiments, the enzyme binds to and transfers the detectable moiety to only modified or only unmodified target sequence. In some embodiments, the enzyme binds to a target sequence comprising at least one CpG. In some embodiments, the target sequence comprises more than one CpG. In some embodiments, all CpGs must be modified or unmodified in order for the enzyme to bind. In some embodiments, the enzyme transfers to a first CpG in the target sequence, but modification of a second CpG blocks binding and transfer to the first CpG. In some embodiments, the enzyme is a bacterial MTase. In some embodiments, the enzyme is selected from M.TaqI, M.SssI, M.BscCI, M.EcoDam, M.HhaI, and MpeI. In some embodiments, the enzyme is selected from M.BscCI, M.EcoDam, M.HhaI, and MpeI. In some embodiments, the enzyme is M.TaqI. In some embodiments, the depositing of the detectable moiety onto the target sequence comprises covalent linkage of the detectable moiety to the DNA.

In some embodiments, the detecting if the detectable moiety is present comprises detecting all moieties on the DNA molecule. In some embodiments, the moiety is fluorescent, and the detecting comprises detection of the total fluorescence while the molecule is translocating through the nanopore. In some embodiments, the detecting comprises determining the dwell time of the molecule in the nanopore. In some embodiments, the detecting comprises determining the length of the molecule based on the dwell time. In some embodiments, the detecting comprises dividing the total measured fluorescence by the length of the molecule to generate the fluorescence per unit length (base pair). In some embodiments, the number of moieties on the DNA molecule is determined by the fluorescence per base pair. In some embodiments, the photon sum of a translocation even is normalized by the residence (dwell) time in the pore. In some embodiments, the fluorescence produced from a single moiety divided by the number of bases in the DNA molecule provides the threshold for determines a positive detection. In some embodiments, each multiple of that threshold value indicates another moiety on the molecule. In this way a difference of even a slight moiety on several Kbp of DNA can be detected.

In some embodiments, the detecting if the detectable moiety is present comprises detecting fluorescence before the molecule translocates through the nanopore, after the naopore translocated through the nanopore or both. By measuring the ion flow through the nanopore and marking when blockade begins and ends the exact dwell time (translocation) of the DNA molecule can be determined. This is the time during which fluorescence or ion flow change (if the moiety is a bulky group) is measured. A background measurement of fluorescence can be determined by measuring fluorescence before and/or after a translocation event. In some embodiments, at least 1, 5, 10, 15, 20, 25, 30, 35, 40, 45 or 50 msec before or after is measured. Each possibility represents a separate embodiment of the invention. In some embodiments, the detecting comprises removing (subtracting) background fluorescence from the fluorescence measuring during the translocation of the DNA molecule. A more accurate reading can be achieved by removing this background, this is called the net photon sum. Combining the background normalization step and the averaging fluorescence over the length of the molecule provides very accurate readings. This can be observed in Table 2, provided hereinbelow. This data is called the net photon flux. In some embodiments, the detecting comprises determining net photo sum for the DNA molecule. In some embodiments, the detecting comprises determining net photo flux for the DNA molecule. Thus, the number of target sequences with or without the modification can be quantitatively determined in DNA molecules of varying sizes and with very similar numbers (even a difference of only 1) of modified or unmodified sequences.

In embodiments where the moiety is a bulky group the background is determined during the translocation, not before or after. Each spike in ion blockade indicates another moiety. Thus, the total number of spikes indicates the total number of modified or unmodified target sequences. The position of the target sequences can also be determined by comparing when in the dwell time each spike occurred, as an earlier spike during the translocation indicates a bulky group earlier in the molecule.

In some embodiments, the DNA molecule is genomic DNA. In some embodiments, the genomic DNA has been sheared. In some embodiments, the DNA molecule is plasmid DNA. In some embodiments, the DNA has not undergone amplification. In some embodiments, the DNA does not undergo amplification. In some embodiments, the DNA has not undergone extension. In some embodiments, the DNA does not undergo extension. In some embodiments, the methods of the invention do not comprise amplification. DNA implication can introduce errors, and the methods of the invention are performed without amplification or extension.

In some embodiments, the methods are for detecting the presence of at least one target modified or unmodified DNA in a plurality of DNA molecules. In some embodiments, the plurality of DNA molecules is in a DNA sample. In some embodiments, the DNA sample is isolated genomic DNA. In some embodiments, the isolated genomic DNA is from a subject. In some embodiments, the plurality of DNA molecules comprises molecules of different lengths. In some embodiments, the molecules of different lengths are at least 0.25, 0.5, 0.75, 1, 1.5, 2, 2.5, 3, 4, 5, 6, 7, 8, 9 or 10 kb different in length. Each possibility represents a separate embodiment of the invention. A skilled artisan will appreciate that not all the molecules need be this different in length but just some. The length differences can make detection difficult, but the unique properties of the electrical and optical combined sensing provided by the nanopore allow for overcoming the difficulty.

Nanopores further provide for rapid analysis of a large number of molecules. In some embodiments, at least 1000 molecules can be analyzed in 0.5, 1, 1.5, 2, 3, 4, 5, 6, 7, 8, 9, 10, 20, 30, 40, 50, or 60 minutes. Each possibility represents a separate embodiment of the invention. Capture rate of the nanopore depends on the concentration of the DNA added (more DNA=faster capture), thus it is ideally suited for samples with large amounts of DNA. Methods that rely on visual analysis, such as nanochannels, are more limited when large DNA amounts are analyzed.

Nanopore Apparatus

In some embodiments, the apparatus is a nanopore apparatus. In some embodiments, the apparatus is part of a nanopore system. Nanopore apparatuses are well known in the art and any known such apparatus may be used. The apparatus may include any components necessary for the running of the nanopore, such as a power source, an input reservoir, a collection reservoir, a channel, a film which comprises the nanopore. The nanopore may be any type of nanopore known in the art, including but not limited to a solid state nanopore, a plasmonic nanopore, a biological nanopore and a nanopore with a nanowell, to name but a few. The apparatus may comprise more than one nanopore and may have an array of nanopores. The nanopores may all be of the same kind, or a mix of types of nanopores. The apparatus may employ isotachophoresis (ITP) focusing of the analyte to the nanopore. The nanopore apparatus may be a nanopore chip.

In some embodiments, the nanopore is a Solid state Nanopores (ssNPs). In some embodiments, the nanopore is a nanopore chip. In some embodiments, the nanopore chip is configured in a solid-state membrane comprising a semiconductor or insulating material. In some embodiments, the nanopore chip is fabricated in a silicon compound membrane. In some embodiments, the nanopore chip contains multi-layer metallic structures. In some embodiments, the nanopore is fabricated using any one of: a TEM microscope, a helium ion microscope, and a method of dielectric breakdown. In some embodiments, the nanopore is fabricated using any one of: a TEM microscope, a helium ion microscope, and a method of dielectric breakdown.

As used herein, the terms "film" and "membrane" are used interchangeably and refer to a thin water-impermeable separation between the first and second reservoirs. In some embodiments, the film is ion-impermeable. In some embodiments, the film comprises silicon. In some embodiments, the film is silicon based. In some embodiments, the film comprises silicon nitride (SiNx). In some embodiments the film comprises a metal oxide. In some embodiments, the metal oxide is selected from aluminum oxide ($AlO_2$), titanium oxide ($TiO_2$), silicon oxide ($SiO_2$) and hafnium oxide ($HfO_2$). In some embodiments, the film is set in a silicon wafer. In some embodiments, the wafer is a crystal orientation wafer. In some embodiments, the wafer is thicker in regions that lack a nanopore. In some embodiments, the wafer provides stability to the separation between the first and second reservoirs. In some embodiments, the wafer comprises a diameter of at least 1, 10, 50, 75 or 100 mm. Each possibility represents a separate embodiment of the invention. In some embodiments, the wafer comprises a thickness of at least 50, 100, 150, 200, 250, 300, 350 or 400 μm. Each possibility represents a separate embodiment of the invention. In some embodiments, the film comprises a metallic layer. Nanowells, plasmonic nanopores, and metallic layered nanopores are all known in the art, and a skilled artisan may use them in constructing the apparatus used for the method of the invention.

In some embodiments, the film has a universal thickness. In some embodiments, the film has a constant thickness across its entire area. In some embodiments, the film has a variable thickness. In some embodiments, the film is thinner in the area of the nanopore. In some embodiments, the film comprises a thickness of less than 500, 450, 400, 350, 300, 250, 200, 150, 100, 75, 50, 25, 20, 15, 10, or 5 nm. Each possibility represents a separate embodiment of the invention. In some embodiments, the film comprises a thickness of less than 100 nm. In some embodiments, the film comprises a thickness of about 25 nm. In some embodiments, the film comprises a thickness of about 10 nm. In some embodiments, the film comprises a thickness of less than 10 nm. In some embodiments, the membrane comprises a thickness of about 25 nm distal to the nanopore and a thickness of about 10 nm proximal to the nanopore. In some embodiments, the membrane comprises a thickness of about 25 nm distal to the nanopore and a thickness of less than 10 nm proximal to the nanopore. In some embodiments, a thin membrane proximal to the pore increases spatial recognition. In some embodiments, a thin membrane proximal to the pore decreases the optical background. In some embodiments, a thin membrane proximal to the pore increases a signal to noise ratio from the molecule. A person skilled in the art will appreciate that the thinner the pore, the fewer the bases in the pore at one instance and thus the greater the spatial recognition of each base of the nucleic acid molecule which also will contribute to decreased background. In some embodiments, the film comprises a thickness that allows light from the light source to pass through the film. In some embodiments, the film allows at least 10%, 20%, 30%, 40%, 50%, 60%, 70%, 80%, 90%, 95%, 97%, 99% or 100% of light to pass through it. Each possibility represents a separate embodiment of the invention.

The production of nanopores in a film is well known in the art. Fabrication of nanopores in thin membranes has been shown in, for example, Kim et al., Adv. Mater. 2006, 18 (23), 3149 and Wanunu, M. et al., Nature Nanotechnology 2010, 5 (11), 807-814. Further, methods of such fabrication of films in silicon wafers, and methods of producing nanopores therein are provided herein in the Materials and Methods section. In some embodiments, the nanopore is produced with a transition electron microscope (TEM). In some embodiments, the nanopore is produced with a high-resolution aberration-corrected TEM or a noncorrected TEM.

In some embodiments, the nanopore comprises a diameter not greater than 1, 2, 3, 4, 5, 10, 15, 20, 15, 30, 35, 40, 45 or 50 nm. Each possibility represents a separate embodiment of the invention. In some embodiments, the nanopore comprises a diameter not greater than 5 nm. In some embodiments, the nanopore comprises a diameter of about 5 nm. In some embodiments, the nanopore comprises a diameter between 0.5 and 10, 0.5 and 15, 0.5 and 20, 1 and 10, 1 and 15, 1 and 20, 3 and 10, 3 and 15, 3 and 20, 5 and 10, 5 and 15, or 5 and 20 nm. Each possibility represents a separate embodiment of the invention.

In some embodiments, the film comprises at least one nanopore. In some embodiments, the film comprises at least 2 nanopores. In some embodiments, the film comprises a plurality of nanopores. In some embodiments, the film comprises an array of nanopores. In some embodiments, the array comprises dimensions of 5×5, 5×10, 5×15, 5×20, 5×25, 5×30, 5×35, 5×40, 5×45, 5×50, 10×10, 10×15, 10×20, 10×25, 10×30, 10×35, 10×40, 10×45, 10×50, 15×15, 15×20, 15×25, 15×30, 15×35, 15×40, 15×45, 15×50, 20×20, 20×25, 20×30, 20×35, 20×40, 20×45, 20×50, 25×25, 25×30, 25×35, 25×40, 25×45, 25×50, 30×30, 30×35, 30×40, 30×45, 30×50, 35×35, 35×40, 35×45, 35×50, 40×40, 40×45, 40×50, 45×45, 45×50, or 50×50 μm. Each possibility represents a separate embodiment of the invention. In some embodiments, the array comprises dimensions of 30 μm by 30 μm. In some embodiments, the nanopores are separated by about 1 μm. In some embodiments, the nanopores are separate by at least 1, 1.5, 2, 2.5, 3, 3.5, 4, 4.5, 5, 6, 7, 8, 9 or 10 μm. Each possibility represents a separate embodiment of the invention. In some embodiments, the nanopores are separated by at least 1 μm. In some embodiments, every nanopore will have a corresponding nanowell. In some embodiments, the detector is configured to detect fluorescence at each nanopore-nanowell. In some embodiments, the detector is configured to detect fluorescence at all nanopore-nanowells. In some embodiments, multiple detectors detect fluorescence at multiple wells.

In some embodiments, the first reservoir is suitable to receive a sample comprising the molecule to be detected. In some embodiments, the second reservoir is suitable for the molecule to pass into after detection. In some embodiments, the reservoirs are the same size. In some embodiments, the first reservoir is larger than the second. In some embodiments, the second reservoir is larger than the first. In some embodiments, the second reservoir is attached to a drainage system for emptying the reservoirs. In some embodiments, the first reservoir holds a volume such that the concentration of molecules in reservoir is not too dilute that molecules infrequently contact the nanopore and not too concentrated that there is crowding and/or blockage of the nanopore. In some embodiments, the first reservoir is configured such that the concentration of molecules in the reservoir is between 1 femtomole and 1 micromole. In some embodiments, the first and second reservoirs are in electrical contact via the nanopore In some embodiments, the apparatus comprises a means to induce movement of the DNA molecule through the nanopore. In some embodiments, the means to induce movement comprises a means of inducing an electrical current from the first reservoir to the second reservoir. In some embodiments, the means to induce movement comprises a negative electrode within the first reservoir and a positive electrode in the second reservoir and wherein the molecule has a negative charge. In some embodiments, the means to induce movement comprises a positive electrode within the first reservoir and a negative electrode in the second reservoir and wherein the molecule has a positive charge. In some embodiments, the molecule is treated with a substance that provides a charge to the molecule before addition to the first reservoir.

In some embodiments, the apparatus comprises at least one sensor. In some embodiments, the apparatus comprises at least an electrical sensor. In some embodiments, the electrical sensor is any one of a voltage, current, resistance, conductivity, ion current flow and impedance sensor. In some embodiments, the electrical sensor measures ion current flow. In some embodiments, the sensor is a multimeter. In some embodiments, the sensor is a voltmeter. In some embodiments, the apparatus is configured for electrical sensing. In some embodiments, the apparatus further comprises an optical sensor. In some embodiments, the optical sensor is a fluorescent sensor. In some embodiments, the fluorescent sensor is a microscope. In some embodiments, the microscope is a confocal microscope. In some embodiments, the optical sensor is a photo detector. In some embodiments, the photo detector is a photo diode.

In some embodiments, the nanopore is configured for at least one of electrical identification, optical identification, bulky group electrical identification and electro-optical identification. In some embodiments, the nanopore is configured for electrical identification. In some embodiments, the nanopore is configured for optical identification. In some embodiments, the nanopore is configured for bulky group electrical identification. In some embodiments, the nanopore is configured for electro-optical identification. In some embodiments, the nanopore is configured to sense the DNA molecule electrically and the cofactor electrically and/or optically. In some embodiments, bulky group and fluorescent cofactors can be used so that detection of the cofactors is electrical and optical. Detection of the molecule through the nanopore is still electrical. In some embodiments, the apparatus is as described herein in the "Nanochip fabrication" section. In some embodiments, the apparatus is as described herein in the "Experimental setup" section.

In some embodiments, the apparatus further comprises a control unit for recording electrical and/or optical measurements. In some embodiments, the control unit performs the determining, including any normalization steps. A control unit, such as is known in the art, may be any computer, microcomputer CPU or the like that can perform the methods of the invention. In some embodiments, the passing and detecting are automated and performed automatically by the control unit.

By another aspect, there is provided a kit comprising:
a. at least one DNA methyltransferase enzyme (MTase);
b. at least one synthetic cofactor of said Mtase comprising a detectable moiety; and
c. a nanopore apparatus comprising a nanopore, and an electrical sensor, wherein the electrical sensor is configured to detect ion flow through the nanopore.

In some embodiments, the detectable moiety is detectable as it passes (translocates) through the nanopore. In some embodiments, the apparatus is any of the embodiments of apparatuses described herein. Similarly any MTase or synthetic cofactor described herein may be a part of the kit.

As used herein, the term "about" when combined with a value refers to plus and minus 10% of the reference value. For example, a length of about 1000 nanometers (nm) refers to a length of 1000 nm+−100 nm.

It is noted that as used herein and in the appended claims, the singular forms "a," "an," and "the" include plural referents unless the context clearly dictates otherwise. Thus, for example, reference to "a polynucleotide" includes a plurality of such polynucleotides and reference to "the polypeptide" includes reference to one or more polypeptides and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements or use of a "negative" limitation.

In those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

Various embodiments and aspects of the present invention as delineated hereinabove and as claimed in the claims section below find experimental support in the following examples.

EXAMPLES

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Maryland (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N. Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Strategies for Protein Purification and Characterization—A Laboratory Course Manual" CSHL Press (1996); all of which are incorporated by reference. Other general references are provided throughout this document.

Methods

Nanochip Fabrication and Assembly for Electro-Optical Sensing

Figure 3A:
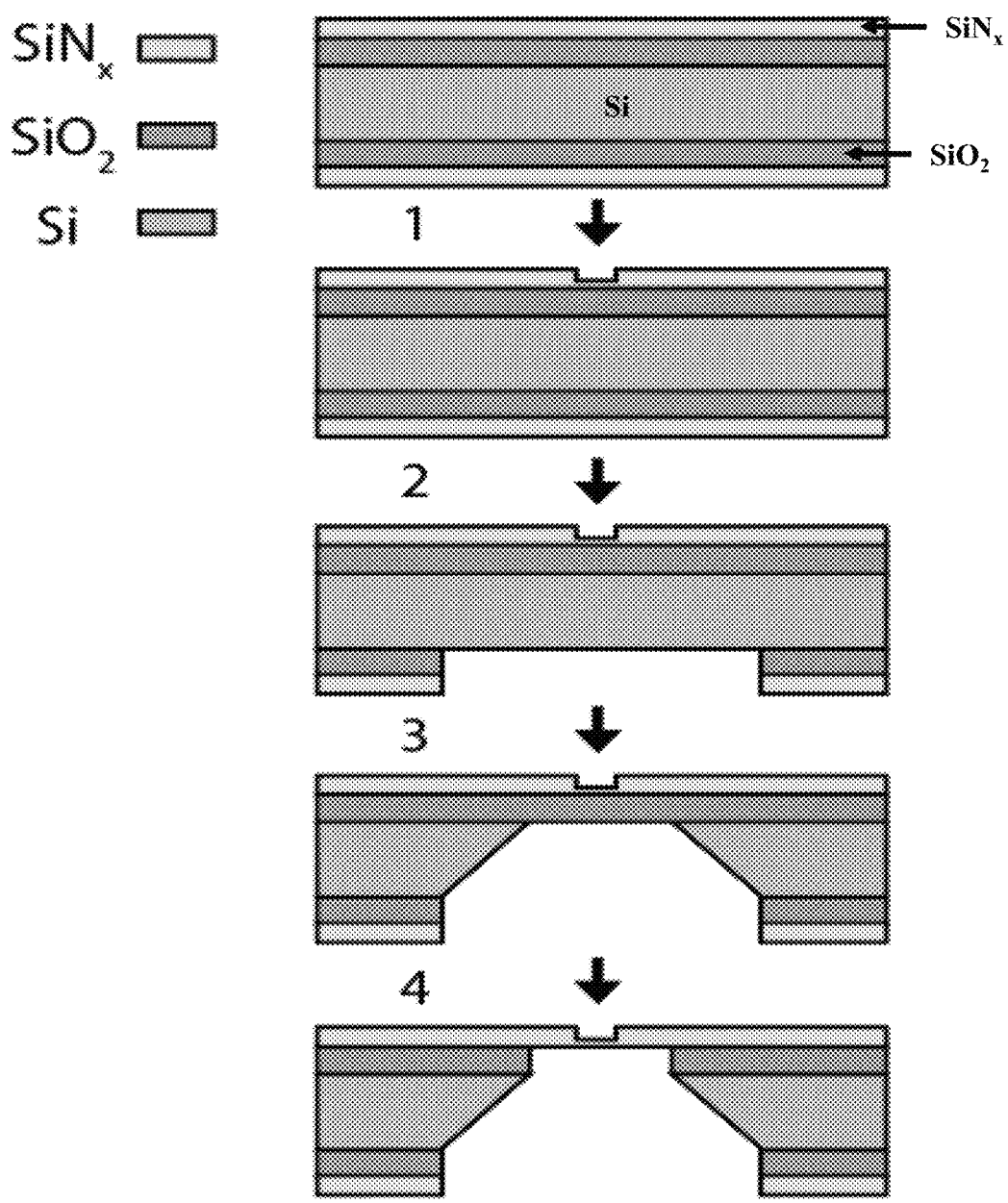
FIGS. 3A-E: Chip fabrication and positioning (3A) A diagram of the four main steps involved in nanopore chip fabrication: 1. Patterning the thin regions by photolithography and RIE; 2. Patterning the windows by photolithography, RIE and BOE; 3. KOH etch; 4. BOE. (3B) Nanopore chip images obtained from the back side (upper image) and front side (lower image), the SiNx membrane containing the thin circular region is seen. (3C) Schematic of chip configuration containing free $SiN_x$ membrane with a thinner region in the middle. (3D) White light optical image of the $SiN_x$ membrane, showing the ~3 μm thinned region. The laser spot can be seen on the membrane (white spot). Outer and inner circles representing the z-scan position and dashed line representing y-scan path. (3E) Line graphs of results from the three scans, to obtain optimal nanochip alignment at the confocal spot.
Figure 3B:
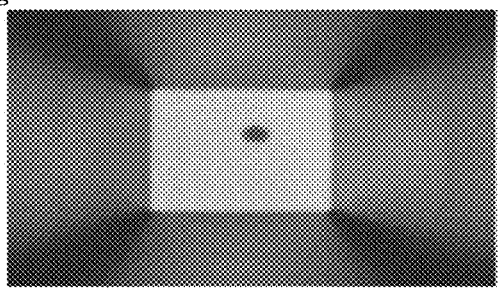
Figure 3B:
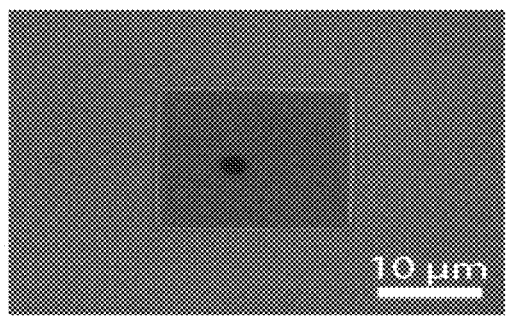

The fabrication process is illustrated schematically in FIG. 3A. Nanopore chips were fabricated in house starting from a 4" double-sided polished Si wafers coated with 500 nm of thermal SiO2 (Virginia Semiconductors, VA, USA). 50 nm thick low-stress silicon nitride (SiNx) was first deposited on both sides of the wafers using Low Pressure Chemical Vapor Deposition (LPCVD). Optical lithography and Reactive Ion Etching (RIE) were then used to pattern ~3 μm (diameter) circles on the "front" SiNx side, to locally reduce the SiNx (at the bottom of each "well") to 10-20 nm (step 1). Windows and dice lines were back-side aligned, and a hard mask pattern was created by a second photolithography step and RIE processes followed by Buffered Oxide Etch (BOE) which removed the SiO2 and exposes the Si layer (step 2). KOH etch was performed until the wafer was fully etched (step 3). Finally, the front side of the membranes (containing the thinned areas) was protected with photoresist and a second BOE step was performed, leaving a clean, freestanding SiNx membrane (step 4). Final nanopore chip images were obtained from both sides. The darker circle in the membrane is the 3 μm well, in which nanopores were drilled at a subsequent step (FIG. 3B).

Nanopores were drilled in the thin circular region of each of the SiNx films by focusing a beam of electron of a high-resolution Transmission Electron Microscope (Titan FEI TEM) with acceleration voltage of 300 keV, following our previously published protocol.

Figure 3C:
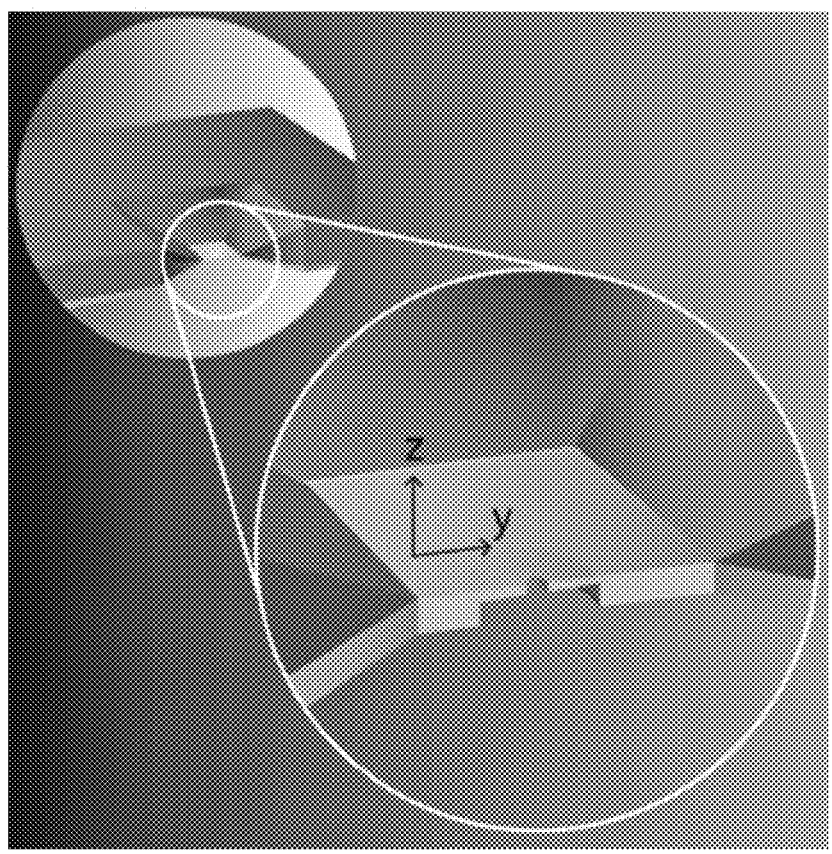
Figure 3D:
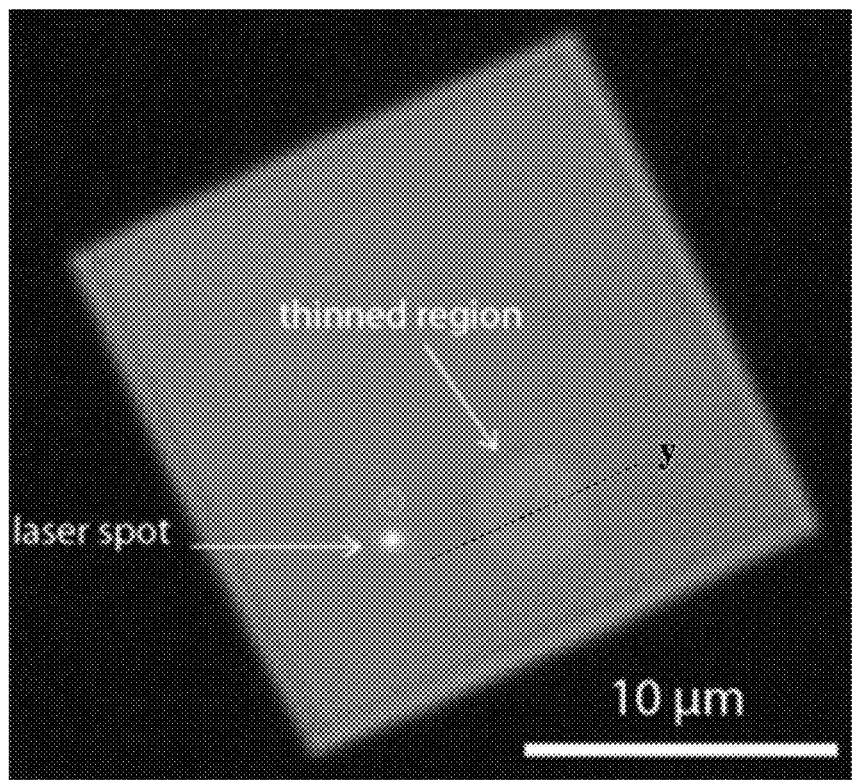

This can also be summarized as follows: reactive Ion etching (RIE) is used to locally thin 3 μm diameter wells in the 50 nm thick low-stress SiNx deposited on silicon wafer substrate to roughly 15 nm. Back-side alignment and RIE are then used to create hard mask square pattern on the back side of the wafer, such that the front side well pattern is centered with the hard mask pattern. Free standing SiNx membranes of size ranging from 10 to 25 μm square were created by anisotropic KOH wet etch. A schematic illustration of the chip, and a white light optical micrograph of the membrane/well area of a typical device are shown in FIGS. 3C and 3D respectively. Nanopores are drilled in the thin circular region of each of the SiNx films by focusing an electron beam using a high-resolution Transmission Electron Microscope (Titan FEI TEM).

The drilled pores are hydrated, mounted onto a custom-made Teflon holder, immersed in buffer, and placed in a home-made cell equipped with a quartz cover-slide bottom. The nanochip cell is mounted on a 3D nanopositioner stage capable of performing nanometer movements and is electrically shielded by a properly grounded home-made copper box. The entire setup is mounted on a vibration isolating optical table.

For the optical sensing a custom made confocal microscope was constructed. Briefly: two collimated laser lines are focused to a diffraction-limited spot at the nanopore position. The emitted light is collected by the same objective, focused onto a spatial pinhole to reject out of focus light, and directed onto two spectrally separated Avalanche Photo Diodes (APDs) for two-color imaging. The ion current flowing through the pore is measured using the two Ag/AgCl electrodes connected to high bandwidth amplifier (Axon 200B) and filtered at 10 kHz. For data acquisition we used two data acquisition boards: NI-6211 DAQ for analog signal acquisition and for applying the voltage bias sampled at 125 KHz, and NI-6602 for photon counting sampled at 500 kHz. The two cards were triggered simultaneously via a hardware connection and were fully controlled by a custom LabVIEW program.

Chips Cleaning

The drilled pores are hydrated and cleaned using pirahna solution (1:3 concentrated sulfuric acid: 30% (w/v) H2O2), rinsed in Milli-Q water (EMD Millipore), vacuum dried, and mounted onto a custom-made Teflon holder with Ecoflex 5 (Smooth-ON) silicone rubber. Next, the chip is wetted and placed in a home-made cell equipped with a quartz cover-slide bottom that permits low background imaging of the SiNx membrane using a high NA microscope objective. The custom cell also permits fluid buffer access (1 M KCl, 40 mM Tris-HCl, 1 mM EDTA at pH 7.5) to the top and bottom chamber (cis and trans, respectively). Two Ag/AgCl electrodes are immersed in the cis and trans chambers and connected to high bandwidth amplifier (Axon 200B).

Experimental Flow, Nanopore Alignment and Data Analysis

Figure 3E:
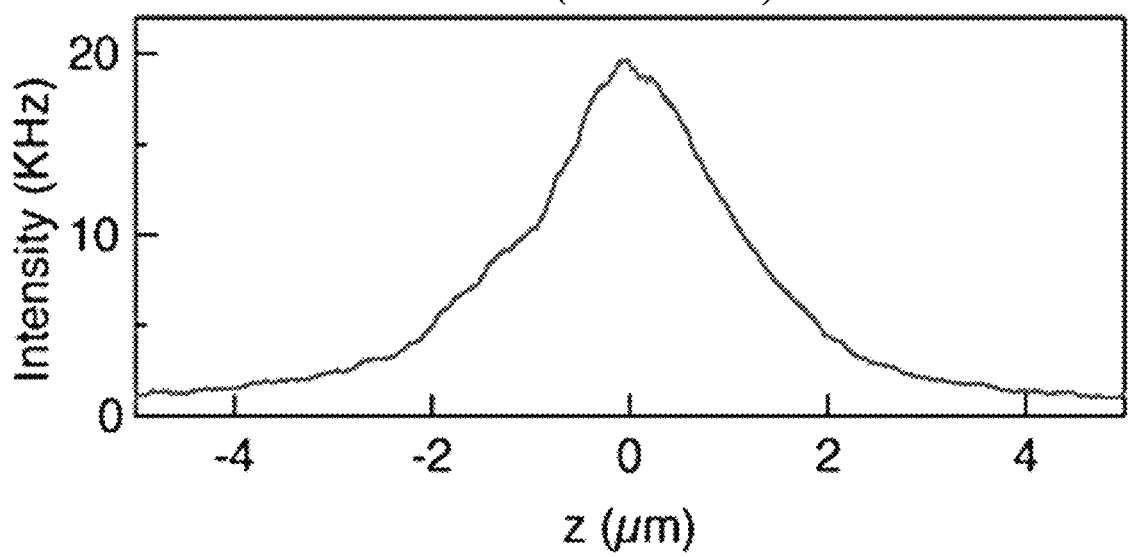
Figure 3E:
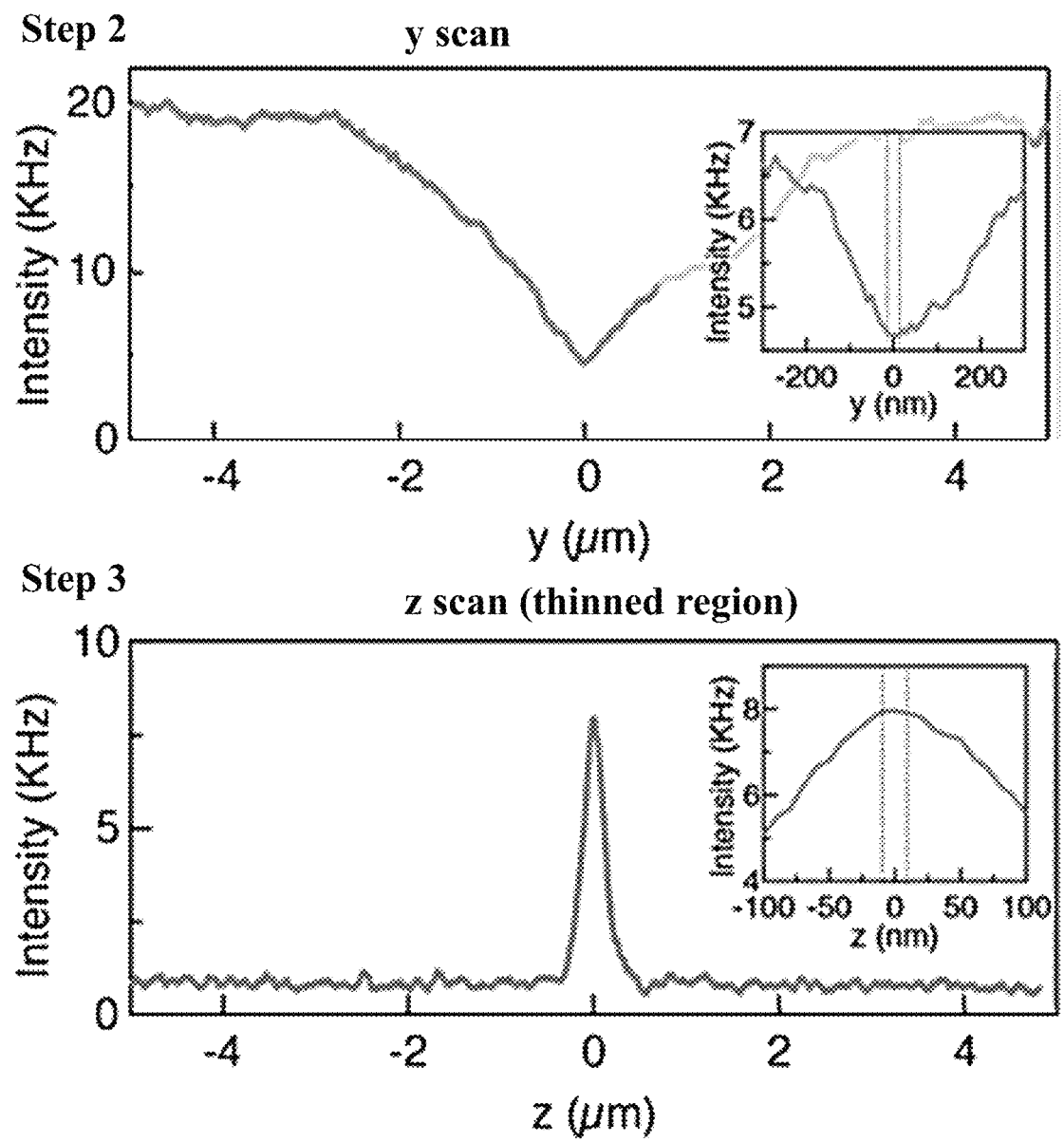

The locally thinned, TEM drilled, chips allow us to substantially reduce the optical background emanated by the membrane hence increasing the signal-to-noise ratio (SNR) of the optical measurements. In addition, this chip configuration highly facilitates the accurate positioning of the nanopore at the confocal laser spot, taking advantage of the fact that the photoluminescence (PL) emanated by the SiNx is strongly suppressed at thinned membrane areas, as well as in those areas that are exposed to strong e-beam intensities during pore drilling. An alignment procedure was carefully performed prior to each experiment, including the following steps: First, white light illumination was used to coarsely align the 3 μm well and the laser spot in the z direction (FIG. 3D). Then, three scans were performed using the nanopositioner to determine the optimal alignment in 3-dimensions. In each case the PL was recorded during the scans (FIG. 3E).

In step 1, a z-scan was performed outside the thin region (marked in a larger circle in FIG. 3D) to obtain the rough membrane position in z-direction, indicated by a clear peak in the scan (curve). In step 2, the z position was fixed to the value where the highest PL was detected in step 1, and membrane was scanned in the x-y dimensions, looking for the point with the minimal PL value. The middle panel of FIG. 3E presents a y-scan of the thin region (scan path is presented by a dashed line in FIG. 3D) in which a clear minimum in the PL is detected with nanometric precision. In step 3, the x-y position was fixed to the point with the lowest PL (smaller inner circle in FIG. 3D) and a second z scan was performed using finer resolution, looking again for the maximum PL representing the membrane position in z-dimension (FIG. 3E, bottom panel). As can be seen in the inset of FIG. 3E (bottom panel) the membrane location is determined with roughly ±10 nm resolution in z, marked by a dashed rectangle.

In a typical experiment ~10 pM of DNA molecules was introduced into the cis chamber. Theoretically in this concentration range<1 molecule resides on average in the confocal volume. This yielded low optical background that enables single fluorophore sensing with high SNR. Each experiment starts by recording both the open pore current of the nanopore and the optical background before adding the DNA. Then the unmethylated, labeled, DNA sample is added to the cis chamber and the electrical and optical signals of the translocation events are recorded. Next the chamber was thoroughly washed, and the same pore was used to translocate the methylated, unlabeled, sample. As a labeled DNA molecule reached the confocal volume an abrupt increase in the optical signal was observed. Synchronization of the electrical and optical signals allowed us to reject events where DNA molecules approach the nanopore but did not translocate through ("unsuccessful translocation") or small fraction of electrical only events. Throughout the experiments our program detected electrical translocation events according to threshold parameters set by the user. The electrical events, padded from both sides, were saved simultaneously with the optical signal detected at the same time.

For data analysis an offline program reads each event at the time from the electrical signal and analyzes it to extract its dwell time (tD), the amplitude drop (IB=iblock/iopen), start time (tstart) and end time (tend). Next, the optical signal extracted from the exact same temporal section is analyzed in the following manner: first the optical data between tstart and tend is extracted and integrated to obtain the average number of photons emitted during the electrical event. Then a second analysis is performed according to optical threshold parameters set by the user to obtain the start time and end times of the optical signals as well as the optical dwell-time tO (see FIG. 4A).

Sample Preparation and Validation

Figure 2A:
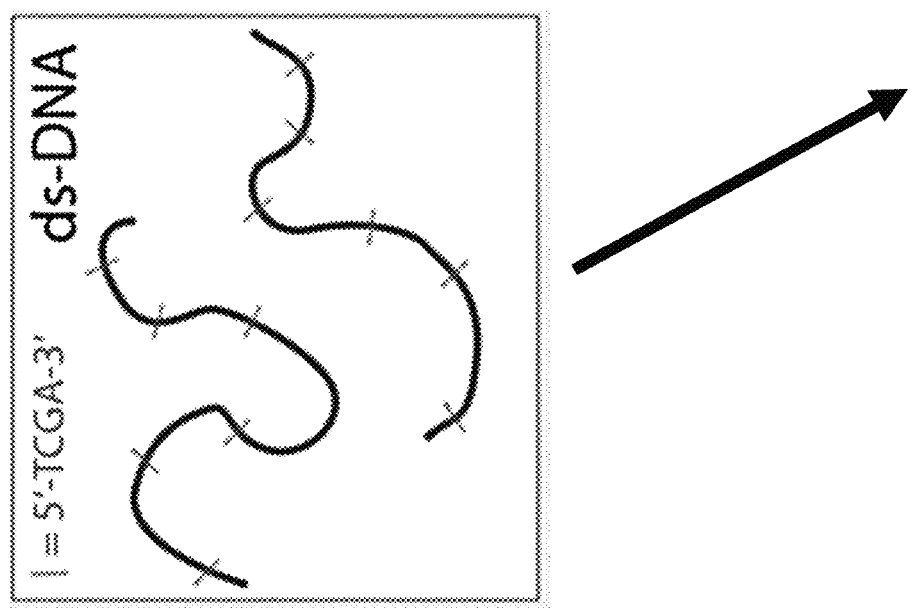
FIGS. 2A-E: Bulk and single-molecule validation of the M.TaqI labeling using custom AdoYnTAMRA. (2A) Schematic representation of the biochemical assay: DNA samples containing known number of M.TaqI recognition sites (5'-TCGA-3') are split to two: one half (left branch) is treated with M.SssI DNA MTase in the presence of native AdoMet, and the second half (right branch) is kept in its original unmethylated state. After purification of the methylated sample, both samples are then incubated with M.TaqI and AdoYnTAMRA under equal conditions. The DNA samples are then challenged with the REase R.TaqI which cleaves unmethylated and CpG-methylated 5'-TCGA-3' sequences but leaves A-modified 5'-TCGA-3' sequences intact. (2B) Western blot analysis of 2.5 kbp, 5 kbp and 10 kbp DNA, either pre-treated with M.SssI/AdoMet or not prior to the incubation with M.TaqI/AdoYnTAMRA, by R.TaqI. Syber Gold staining of the DNA (right panel), shows that only the CpG-methylated fragments were digested. TAMRA excitation (left panel) shows single bands for the −M.SssI samples (unmethylated). Together these gels validate the activity of the M.TaqI/AdoYnTAMRA as expected. (2C) Distribution of M.TaqI recognition sites (5'-TCGA-3') along the three DNA samples used throughout the paper. A 2,500 bp DNA with 6 sites. A 4,995 bp DNA with 7 sites. And a 10,016 bp DNA with 21 recognition sites. (2D) Agarose gel electrophoresis of 2.5, 5 and 10 kbp labeled and unlabeled DNA (in the absence of M.TaqI). The left panel shows a gel scan image of the DNA. Fluorophores were excited by a 532 nm laser and filtered at 580 nm. The right panel shows SYBR Gold staining of labeled DNA and unlabeled DNA. The image confirms that TAMRA fluorophores are added by M.TaqI. (2E) Representative electro-optical traces of the six DNA samples as in panel b. Optical signals are only observed for the −M.SssI samples (unmethylated).
Figure 2A:
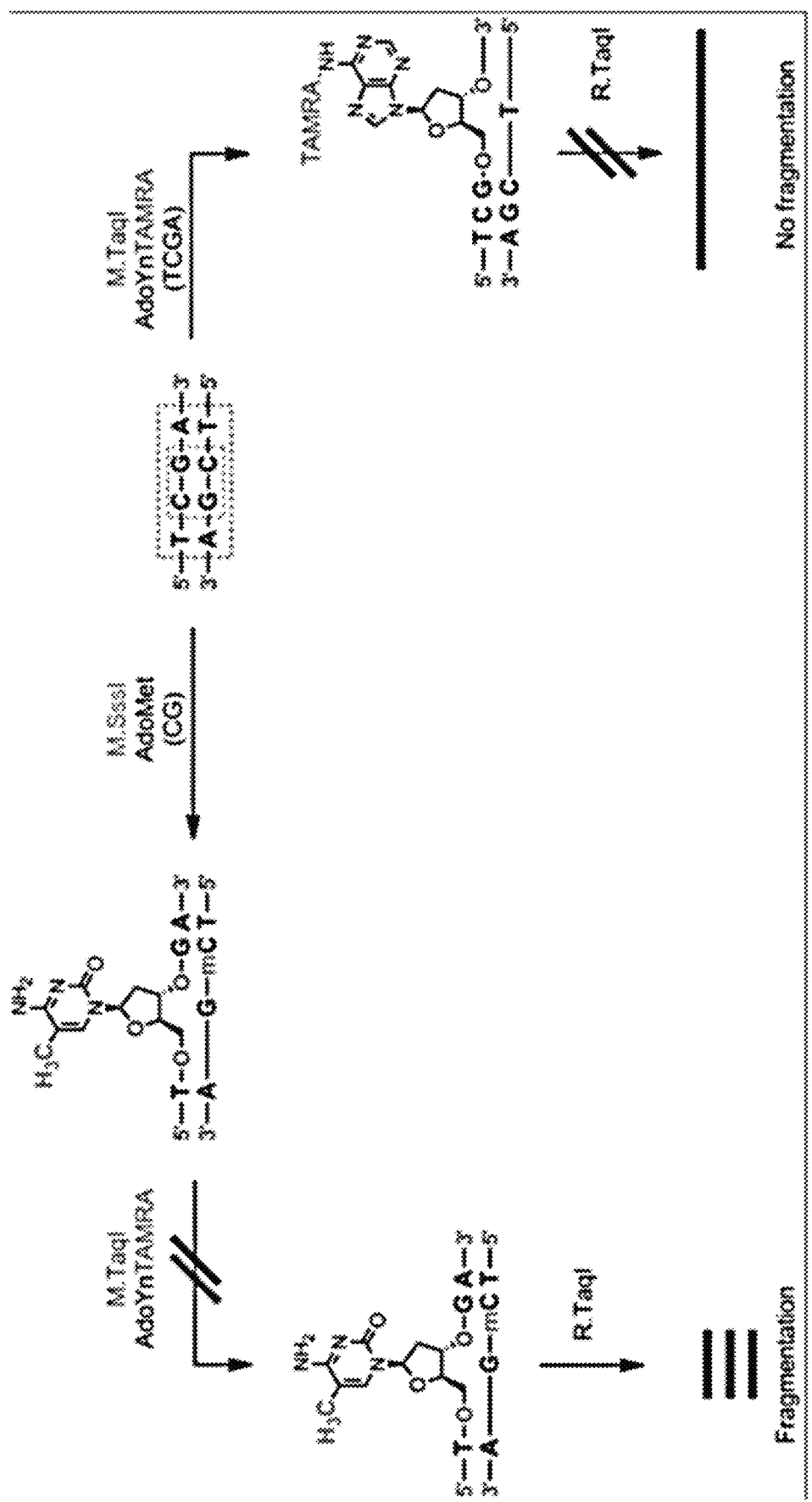
Figure 2A:
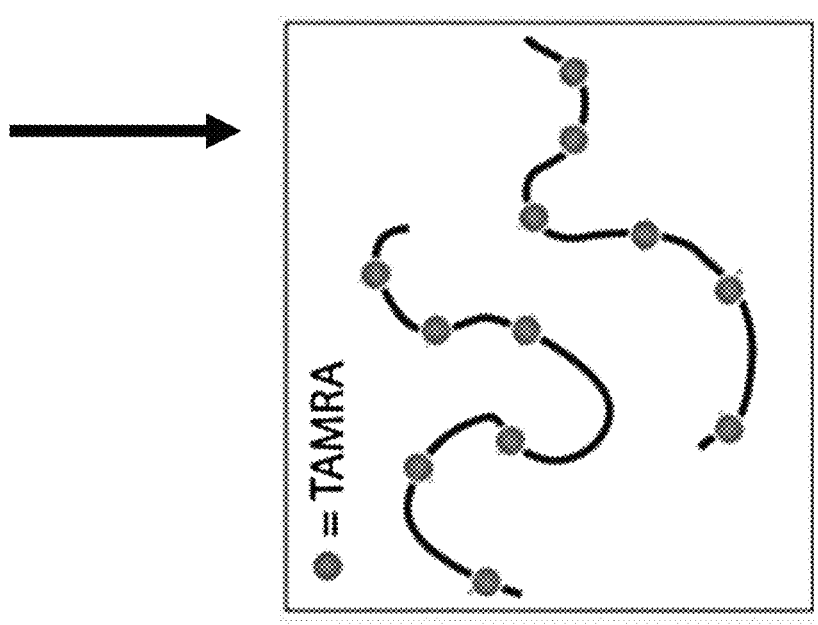
Figure 2A:
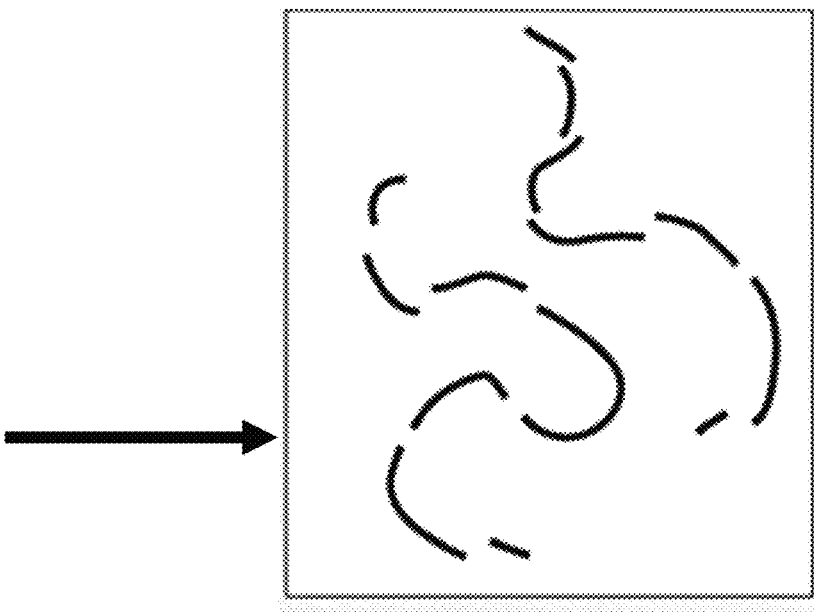
Figure 2B:
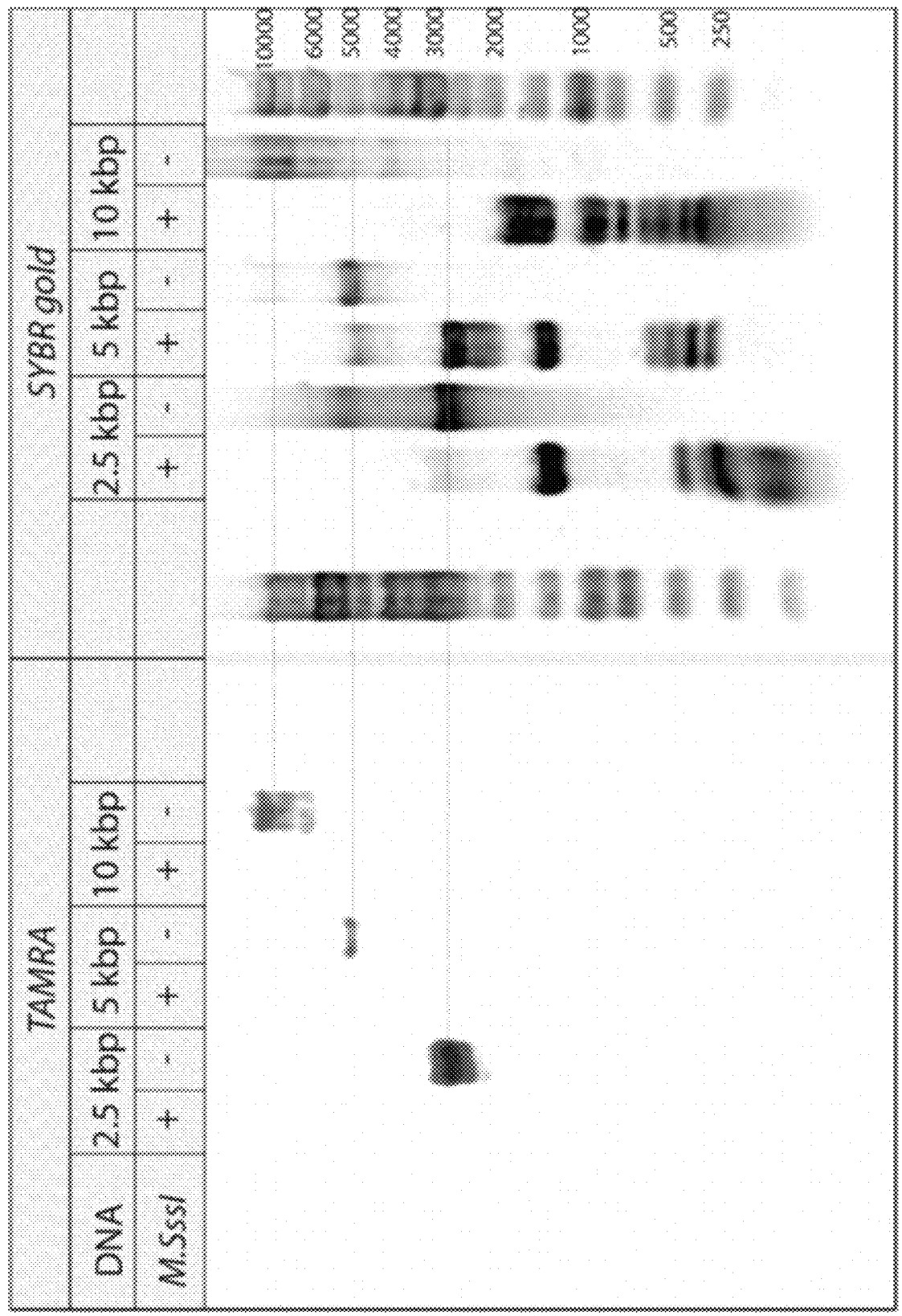
Figure 2C:
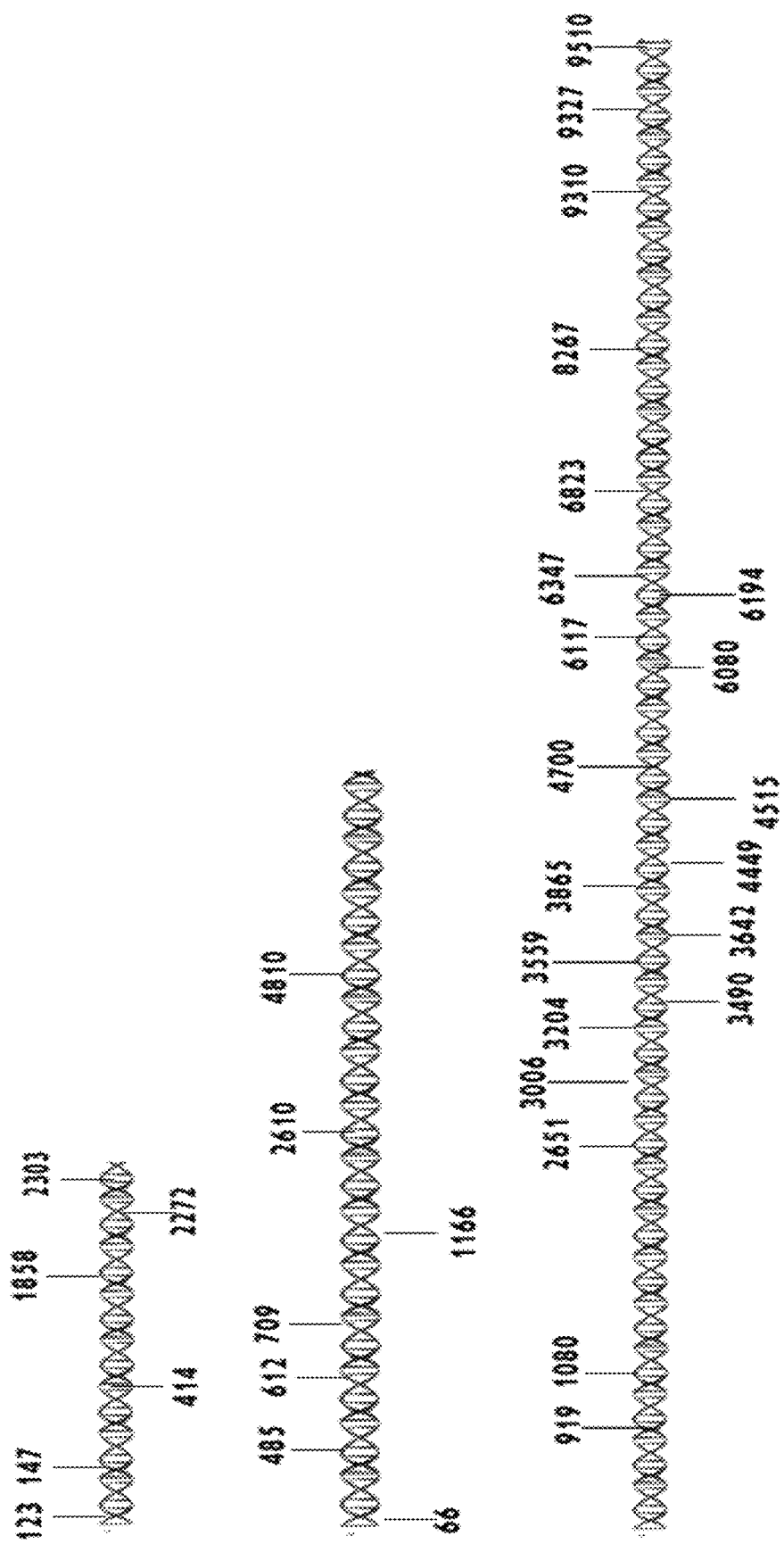
Figure 9:
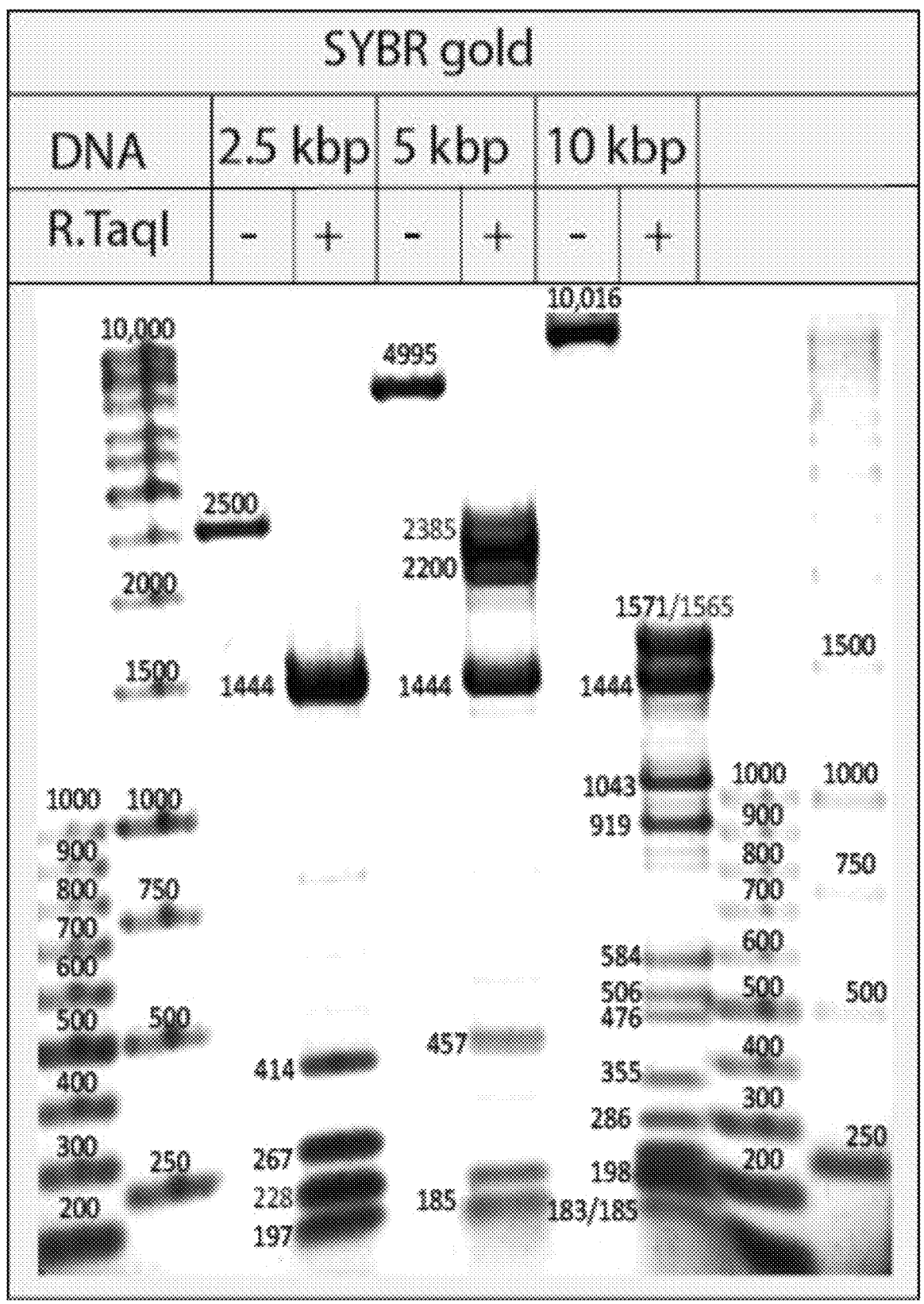
FIG. 9: Photograph of gel showing validation of M.TaqI sites by fragmentation and analysis by 1.2% agarose gel electrophoresis. SYBR Gold image of 2.5 kbp, 5 kbp and 10 kbp unlabeled DNA samples cleaved by R.TaqI. The left lane in each DNA length is a negative control of DNA without R.TaqI endonuclease treatment.

To validate the existence of M.TaqI recognition sites in the DNA samples used, we digested unlabeled DNA with R.TaqI (recognition site 5'-TCGA-3'). The cleaved samples and their controls (uncut DNA) were analyzed on a 1.2% agarose gel stained with SYBR Gold for imaging. FIG. 9 presents the obtained fragments from the digested DNA compared to the non-digested DNA. The fragments resolved are consistent with our sequencing analysis of the location of 5'-TCGA-3' sites (FIG. 2C).

For the validation experiment 5 μg of DNA (No Limit, Thermo Scientific) at 0.5 μg/μl was divided into two equal samples. The first sample was methylated using M.SssI (Thermo Scientific) by treating it with 80 μM S-adenosyll-methionine (New England Biolabs) in M.SssI reaction buffer (10 mM Tris-HCl, pH 7.5, 10 mM MgCl2, 0.1 mg/ml BSA) at a total volume of 30 µl, for 1 h at 37 oC. The reaction was stopped by heating to 65 oC for 30 min. To remove the residual cofactor, we performed ethanol precipitation using standard protocols. The pellets were vacuum dried and re-suspended in 5 µl of DDW.

The methylated and unmethylated DNA samples were then treated with M.TaqI and AdoYnTAMRA (or AdoYnCF40R). Labelling reactions were carried out as follows: roughly 2.5 µg DNA was dissolved in a buffer containing 50 mM KOAc, 20 mM Tris-HOAc, pH 7.9, 10 mM MgOAc$_2$, 1 mM DTT, 0.01% by volume Triton X-100, 100 µg/ml BSA) and AdoYnTAMRA (40 µM final concentration, prepared in house) as well as 10 equivalents of M.TaqI per TCGA site. Reactions were performed at total volume of 25 µl for 2.5 h at 65° C. Reactions were stopped by adding 40 µg of proteinase K (20 µg/µl) (Thermo Scientific) and incubation for 1 h at 45° C. To remove the residual cofactor, we performed ethanol precipitation using standard protocols. After washing the pellet 5 times with 70% ethanol it was vacuum dried and re-suspended in 20 µl of DDW for UV-Vis absorption quantification. Two color labeling was performed similarly to the one color labeling, however since we find that that M.TaqI has slight preference for AdoYnTAMRA over the AdoYnCF640R we used 10 µM final concentration of AdoYnTAMRA and 30 µM of AdoYnCF640R.

Validation of the prepared DNA samples was performed as follows: 300 ng of TAMRA-labeled DNA or 300 ng M.SssI-methylated DNA were treated with 1 µl of 10 U/µl R.TaqI restriction enzyme (Thermo Scientific) in 10 µl R.TaqI buffer. The samples were incubated for 3 h at 65° C. The reactions were stopped by adding 0.5 M EDTA, pH 8.0 to a final concentration of 20 mM. 2 µl of 6× electrophoresis loading buffer (50 mM Tris, 60 mM EDTA, 60% glycerol) were added and the samples were loaded on a 0.8% agarose gel. Samples were allowed to run for 90 min at 100 V, and then imaged using a 532 nm laser gel scanner (GE Healthcare, Typhoon) followed by SYBR Gold staining (30 min) and re-imaging.

Data Acquisition

During an experiment a custom LabVIEW (LV) program detects electrical translocation events according to threshold parameters set by the user. These events, in addition to a specific padding of typically 30 ms before and after each event, are concatenated and saved. The optical signals detected at the same period of time by each APD (see Experimental setup) are concatenated and saved as well. To synchronize the electrical and optical data acquisition, the two cards were triggered and synchronized via a common hardware connection. In addition to the raw data we save a text file containing information about the experiment and a list with the start index and end index of each event. This data is used to extract the events from the binary data files for offline analysis.

Data Analysis

Figure 4:
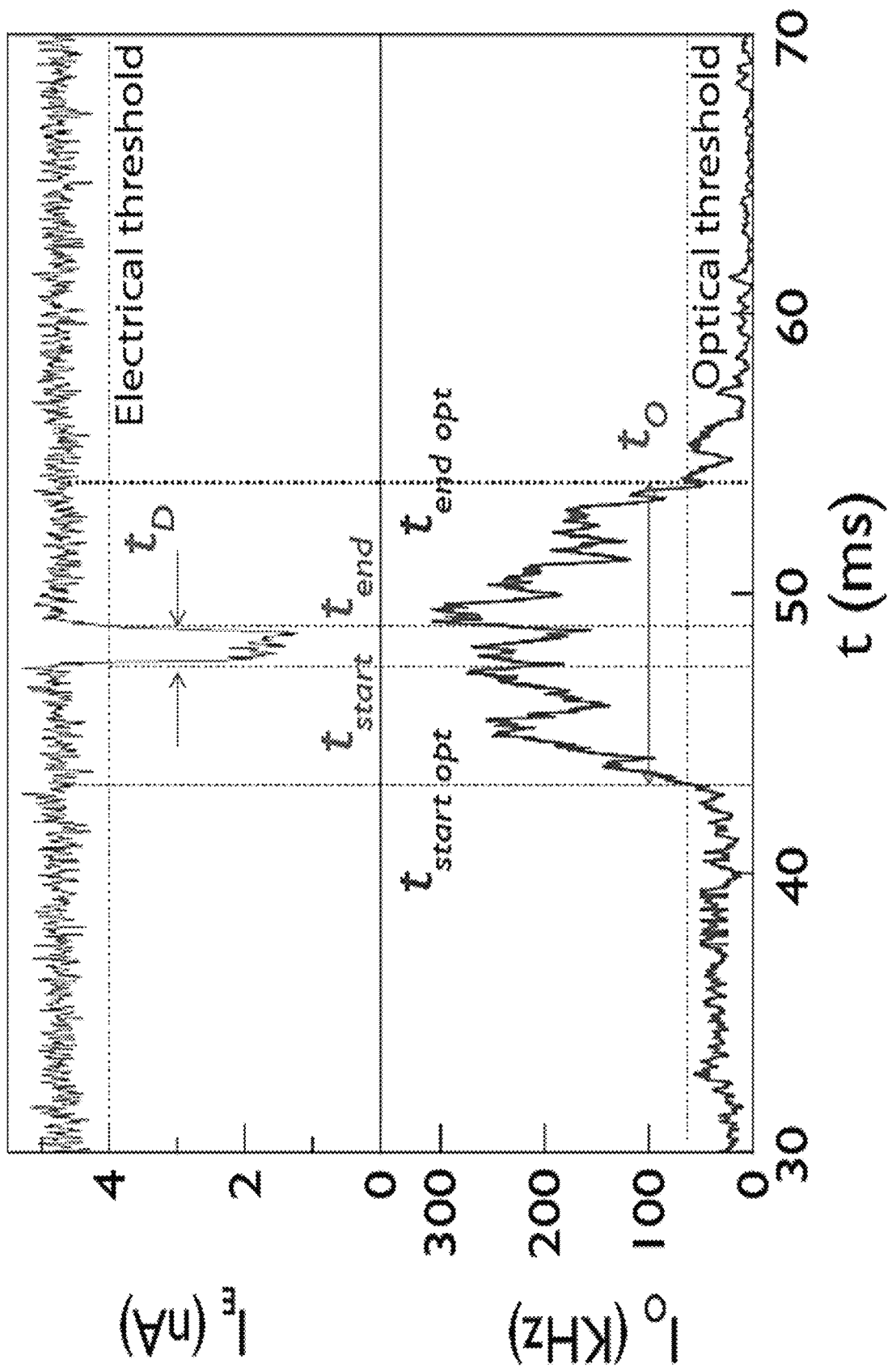
FIG. 4: Event analysis. Line graph showing that for each event the electrical signal is analyzed according to an electrical threshold (upper horizontal dashed line) to extract the beginning (tstart) and end (tend) of the electric event. Then the optical signal is analyzed according to an optical threshold (lower horizontal dashed line) to extract the beginning (tstart_opt) and end (tend_opt) of the optic event. Events in which the electrical and optical signals are not synchronized, (i.e. if tstart_opt>tend or tend_opt<tstart) are rejected.

The offline analysis for each event starts by extracting the dwell time, ($t_D$) amplitude drop ($I_B=I_{blocked}/I_{open}$), start time ($t_{start}$) and end time ($t_{end}$) of its electrical signal according to the electrical threshold. Next, the optical signal between $t_{start}$ and $t_{end}$ is extracted and integrated to obtain the number of photons emitted during the electrical event. Then a second analysis is performed according to the optical threshold to obtain the start time of the optical signal ($t_{start\_opt}$), the end time ($t_{end\_opt}$) and the total dwell time of the optical signal ($t_O$). The optical data between $t_{start\_opt}$ and $t_{end\_opt}$ is extracted and integrated to obtain the number of photons emitted during the entire optical event (FIG. 4). Events in which the electrical and optical signals are not synchronized, (i.e. if $t_{start\_opt}>t_{end}$ or $t_{end\_opt}<t_{start}$) are rejected.

After the initial analysis three main parameters are calculated: The average photon flux during the electrical event (sum of the number of counts during the electrical event divided by $t_D$), the average photon flux during the optical event (sum of the number of counts during the optical event divided by $t_{D\_opt}$), and the photon fluxes before and after each of the optical events (representing the optical background for each event), used to define the background.

To compare between the labeled and unlabeled (unmethylated and methylated) DNA samples we used the photon flux obtained during $t_D$. This allowed us to acquire the total photon detected during each DNA translocation, regardless of if the DNA is labelled or not. As shown in Example 3 (FIG. 5A-D) the background signal distribution overlaps with the fully methylated (un-labeled) DNA. For the methylation quantification stage, we quantified the photons flux from each DNA molecule during to and subtract the background photon flux calculated before and after the optical event start/end time. This way our results were not affected by small changes in the background level during the experiment.

Experimental Setup

Figure 6:
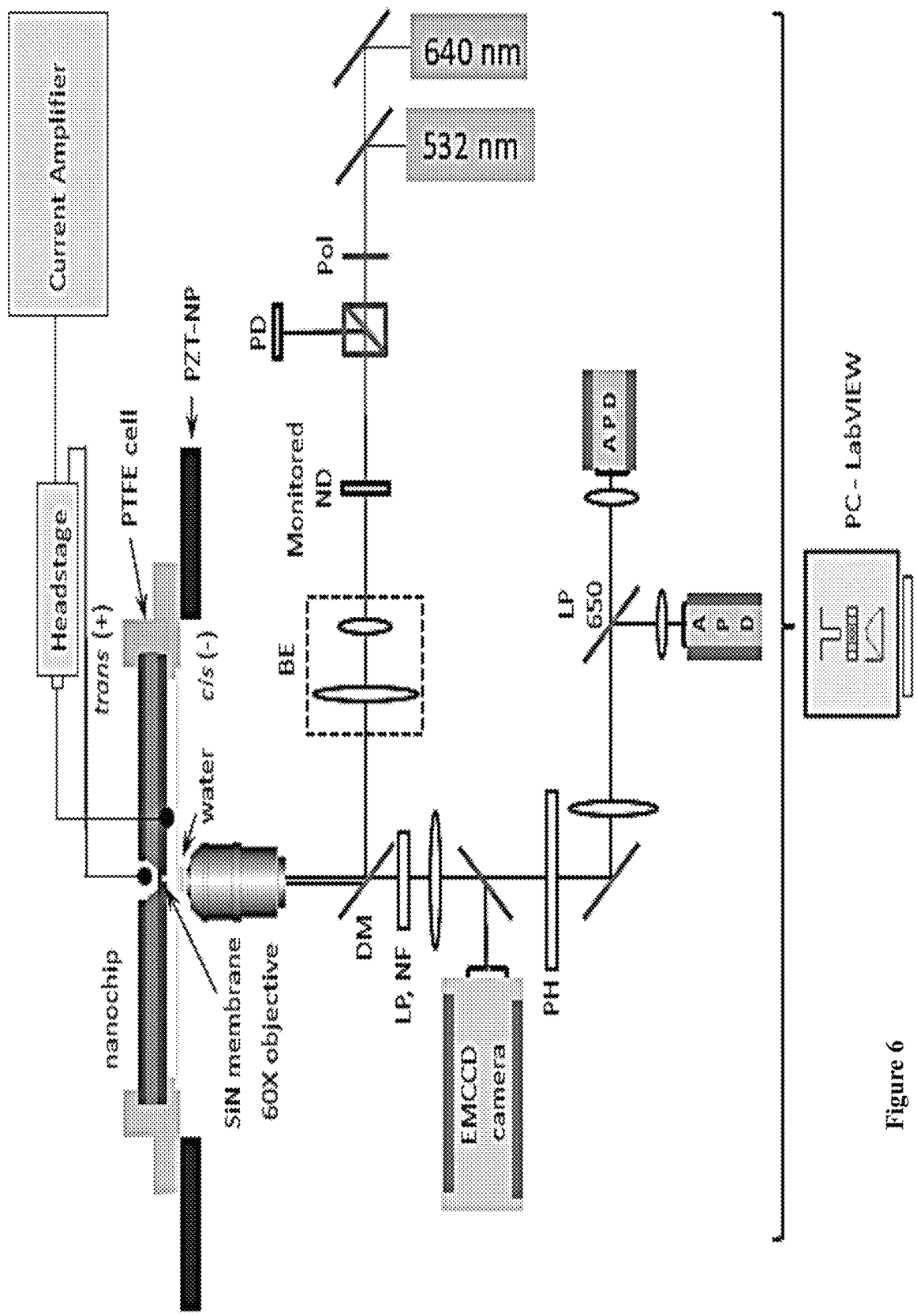
FIG. 6: A schematic of the experimental setup. Abbreviations: PD, Photo-diode; Pol, Half-wavelength wave plate; BE, Beam Expender; DM, Dichroic Mirror; LP, long pass; NF, Notch Filter; PH, Pinhole; APD, Avalanche Photo-Diode; PZT-NP, Piezo-Nanopositioner; PTFE, Polytetrafluoroethylene.

FIG. 6 displays schematically our electro-optical measurement system. For the synchronous optical and electrical measurements, the nanochip is mounted on a closed-loop XYZ nanopositioner (Physik Instrumente, P 561.3) with sub-nm accuracy on top of a high-NA objective (Olympus Plan Apochromat 60×/1.2) in a custom built confocal setup. A 532 nm solid state laser (QiOptiq, iFlex Mustang) and a 640 nm solid state laser (QiOptiq IFlex2000) are used for the excitation, and their intensity is adjusted using natural density (ND) filter wheel (Thorlabs FW212CNEB). The laser beams are expanded to completely fill the back aperture of the objective using a custom-made telescope. Emitted light is collected by the same objective and filtered using the appropriate long pass and notch filters (Semrock) and then focused using a single 20 cm focal length lens onto either an EMCCD camera (ANDOR, iXon 887) or to a 50 µm pinhole (Thorlabs) in confocal mode. Light passing through the pinhole is collimated using a 10 cm lens, split using a dichroic mirror (Semrock) with center wavelengths of λ=650 nm and focused using additional 2.5 cm focal length achromatic doublet lenses onto two APDs (Perkin Elmer SPCM-AQR-14). All lenses were obtained from Thorlabs. The ion current is synchronously measured using two Ag/AgCl electrodes connected to an Axon Axopatch 200B patch-clamp and filtered at 10 KHz. For data acquisition we used National Instruments NI-6211 DAQs for analog signals (sampled at 125 KHz) and NI-6602 for photon counting (sampled at 500 KHz). The two cards were triggered and synchronized via a common hardware connection and were fully controlled by a custom LabVIEW (National Instrument) program. Back reflection was continuously measured using a photodiode (Thorlabs) to monitor and correct stage or sample drift during the experiment.

Example 1

Electro-Optical Sensing of Methyltransferase Coupled Fluorophores

DNA MTases catalyze the transfer of the activated methyl group from the natural cofactor S-adenosyl-1-methionine (AdoMet) to the C5 or N4 position of cytosine or the N6 position of adenine, within specific double-stranded DNA sequences ranging from two to eight base pairs. The catalytic repertoire of DNA MTases has been extended with synthetic AdoMet analogues used for functionalization and labeling of DNA. Here, we synthesized and used double-activated AdoMet analogues, which contain extended unsaturated side chains instead of a methyl group at the sulfonium center. The extended side chain, which replaces the methyl group in AdoMet, reduces the reaction rate of the transfer by the MTase due to unfavorable steric effects within the transition state. In order to accelerate the reaction rate, a triple bond was placed within the transferred chain, next to the reactive carbon, which led to stabilization of the transition state and hence to a faster reaction rate. The extended side chain in the AdoMet analogues were equipped with either the orange fluorophore TAMRA (ex. 555 nm, em. 580 nm), or the red fluorophore CF640R (ex. 642 nm, em. 662 nm). These fluorophores were selected due to their high brightness and single-molecule compatibility. To incorporate the reporter molecules we used the DNA MTase from Thermus aquaticus (M.TaqI), which recognizes the double-stranded DNA sequence 5'-TCGA-3' and modifies the associated adenine residue. M.TaqI is CpG methylation sensitive and only modifies DNA if the CpG within the recognition site is unmethylated (FIG. 1A).

Figure 1B:
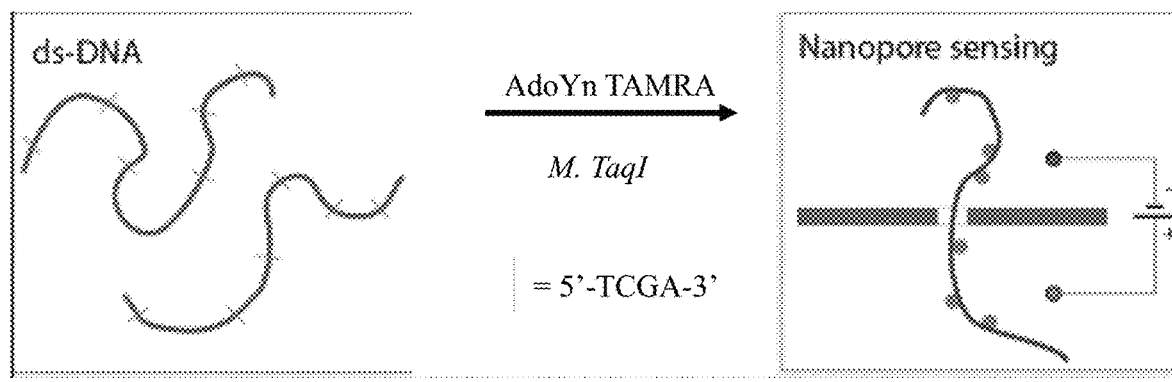
Figure 1C:
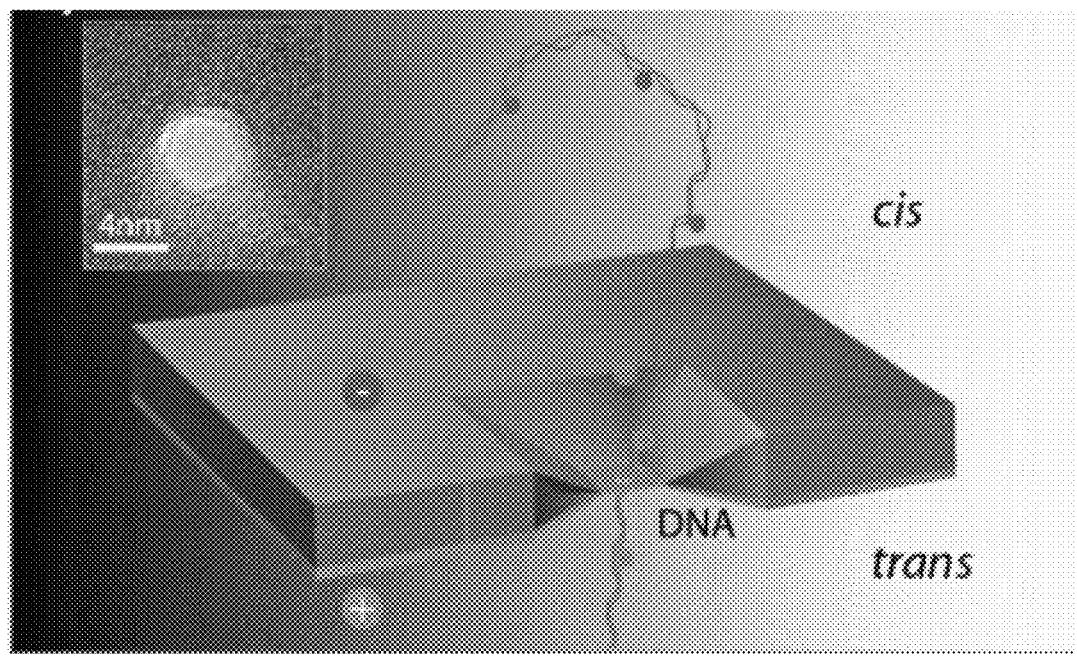
Figure 1D:
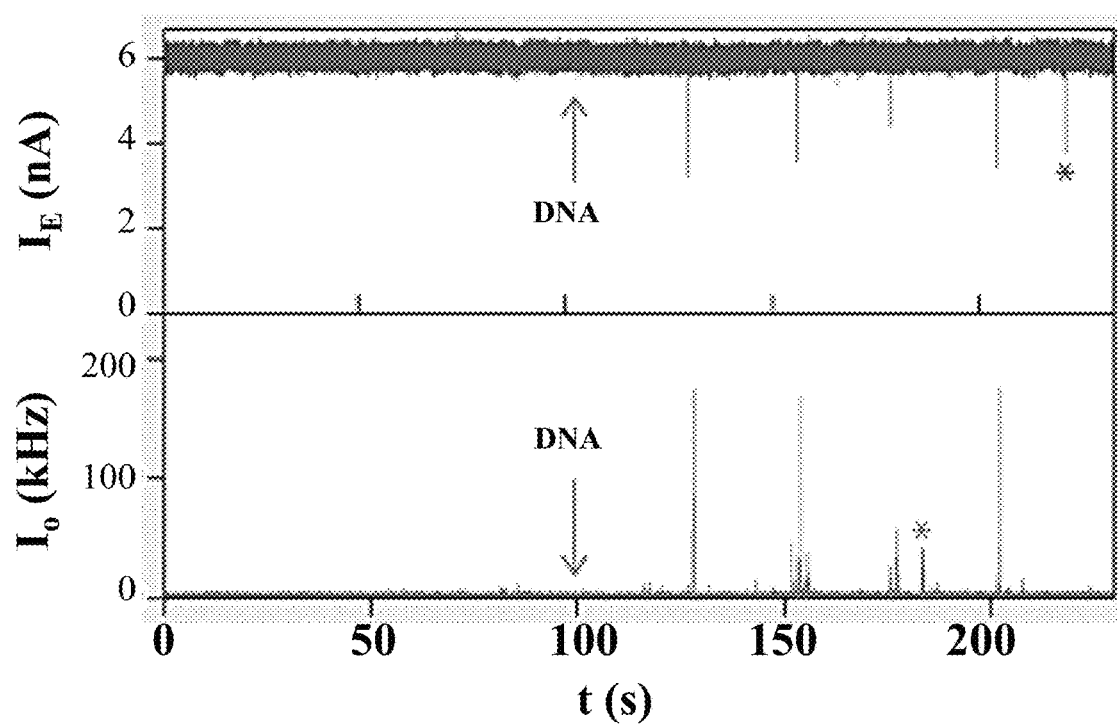
Figure 1E:
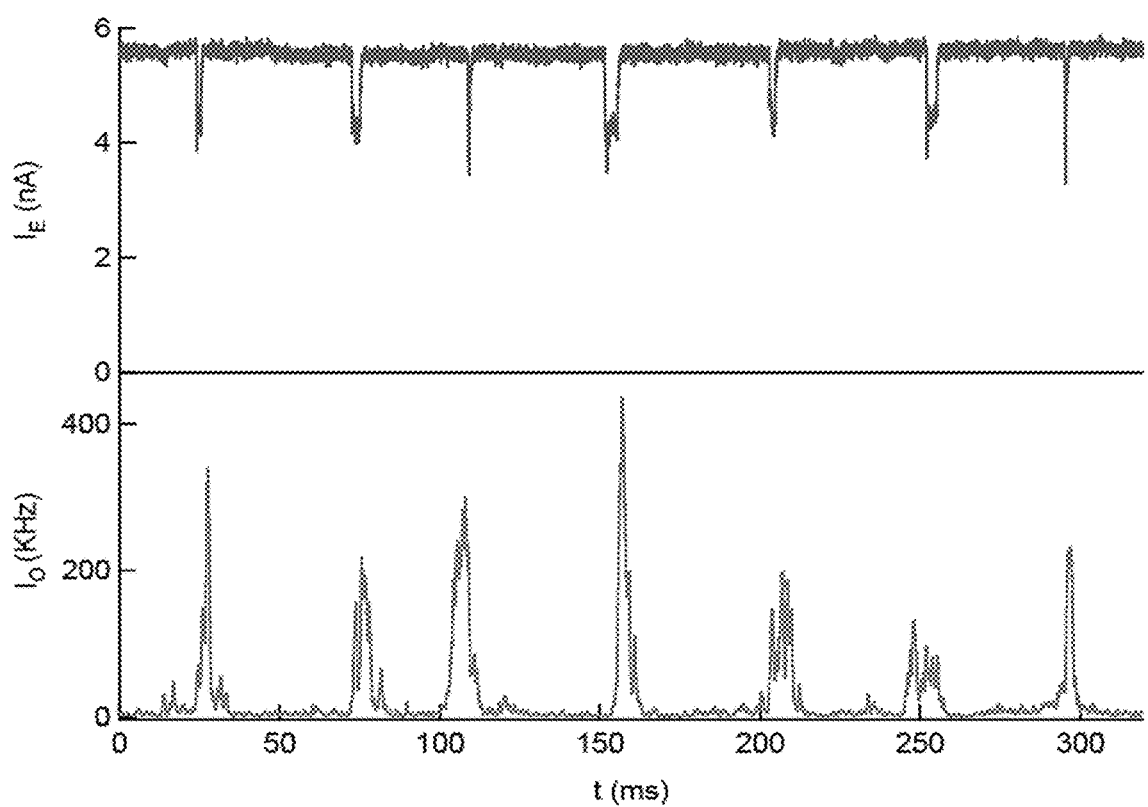

Our approach is illustrated schematically in FIG. 1B: DNA molecules are labeled using M.TaqI in the presence of the synthetic AdoMet analogue AdoYnTAMRA (or AdoYnCF640R). After removal of residual cofactor molecules, a small DNA quantity (roughly 1 femtomole) is introduced to the cis chamber of our nanopore apparatus, where ion current flow and photon emission from the pore area are measured synchronously. FIGS. 1C-D depict the nanopore sensing process (1C) and show typical time traces of electrical (top line) and optical (lower line) signals obtained using a 4 nm diameter pore before and after introducing the DNA at t=100 s (1D). A few seconds after the addition of the DNA, we observe discrete downward spikes (or 'blockades') in the ion current (IE), each corresponding to the translocation of an individual DNA molecule from the cis to trans chamber. The vast majority of electrical translocation events are accompanied with synchronous bursts of photons (IO). Notably, some lower-amplitude photon bursts appear even when there is no electrical blockade (an example is marked with an asterisk). These photon bursts correspond to molecules that pass through the optical detection volume near the pore, but do not translocate through. Occasionally, we can also identify rare electrical translocation events that are not associated with photon bursts (an example is marked with an asterisk). These events represent either incomplete labeling by the DNA MTase or bleached fluorophores. In this study, we synchronously detect the ionic current and photon emission during DNA transport through the pore in order to circumvent inaccurate identification of DNA methylation. FIG. 1E shows a similar analysis but using AdoYnCF640R to label the 5 kbp DNA fragment.

Example 2

Validation of the Methylation Detection Scheme

In order to validate and calibrate the DNA labeling and sensing assays, we developed a variant of the biochemical protection/restriction assay for bulk and single-molecule characterizations. Our assay is depicted schematically in FIG. 2A. Uniform length unmethylated DNA samples containing known numbers of M.TaqI recognition sites (5'-TCGA-3'), were either treated with the DNA MTase M.SssI in the presence of its native cofactor AdoMet to methylate all CpG dinucleotides, including these within the 5'-TCGA-3' recognition site for M.TaqI (left branch), or kept in the original unmethylated state (right branch). Both samples were then incubated with M.TaqI and AdoYnTAMRA under identical conditions. To verify our sample preparation, we took advantage of the fact that the cognate restriction endonuclease (REase) R.TaqI cleaves CpG-methylated as well as unmethylated 5'-TCGA-3' sequences, but does not restrict the DNA if the adenine within the 5'-TCGA-3' sequences is modified. Therefore, agarose gel electrophoresis could be used to directly verify that M.TaqI labeled sites were not restricted by R.TaqI, while unlabeled samples were digested, as is shown in FIG. 2B.

Three different DNA molecules, roughly 2.5, 5 and 10 kbp long having 6, 7 or 21 recognition sites respectively were chosen in order to quantify different methylation levels. FIG. 2C presents the three DNA lengths used in the experiments (2.5 kbp, 5 kbp, 10 kbp) with the location of the M.TaqI recognition sites (5'-TCGA-3') in base pairs obtained by sequencing analysis. Each DNA sample was treated as explained in FIG. 2A and was subject to gel electrophoresis analysis. We first imaged the gel in the TAMRA channel (532 nm laser excitation and a 580 nm bandpass filter) as shown in FIG. 2B, left. Then the gel was stained with SYBR Gold in order to highlight the unlabeled DNA bands (FIG. 2B, right). We note that fragmentation bands appear only for the M.SssI-treated samples for all three DNA molecules, whereas the non M.SssI-treated samples remain uncut. Each of the uncut bands aligns well with a single band that appears for TAMRA emission (left panel), but the M.SssI methylated samples do not show any TAMRA labeling. These results confirm that CpG methylation blocks labeling of DNA by M.TaqI, providing a fluorescent reporter for the DNA methylation state.

Figure 2D:
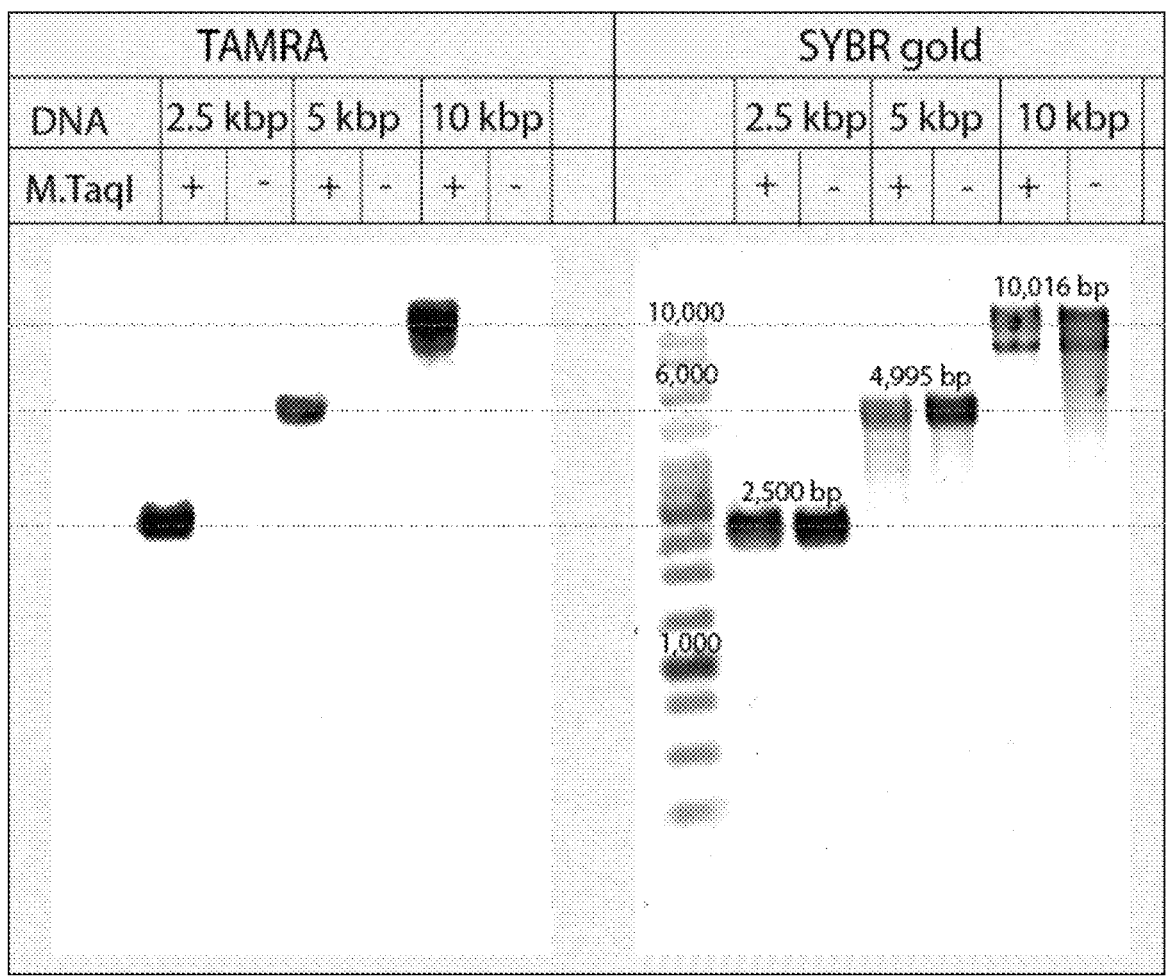

In order to validate that DNA labeling occurs only in the presence of M.TaqI, a negative control experiment showing that no labeling occurs in the absence of M.TaqI was performed. Labeling experiments were performed for the three lengths of DNA, with and without the enzyme, keeping all other conditions the same. We then loaded 150 ng of each of the six samples (2.5 kbp, 5 kbp and 10 kbp DNA with or without M.TaqI) onto a 0.8% agarose gel, and analyzed the fluorescence before and after staining with SYBR Gold using a gel scanner. In FIG. 2D we present a scan image of the gel before staining (excitation at 532 nm for TAMRA, left panel) and post-staining with SYBR Gold (right panel). The gel confirms that fluorophores are added only in the presence of M.TaqI.

Figure 2E:
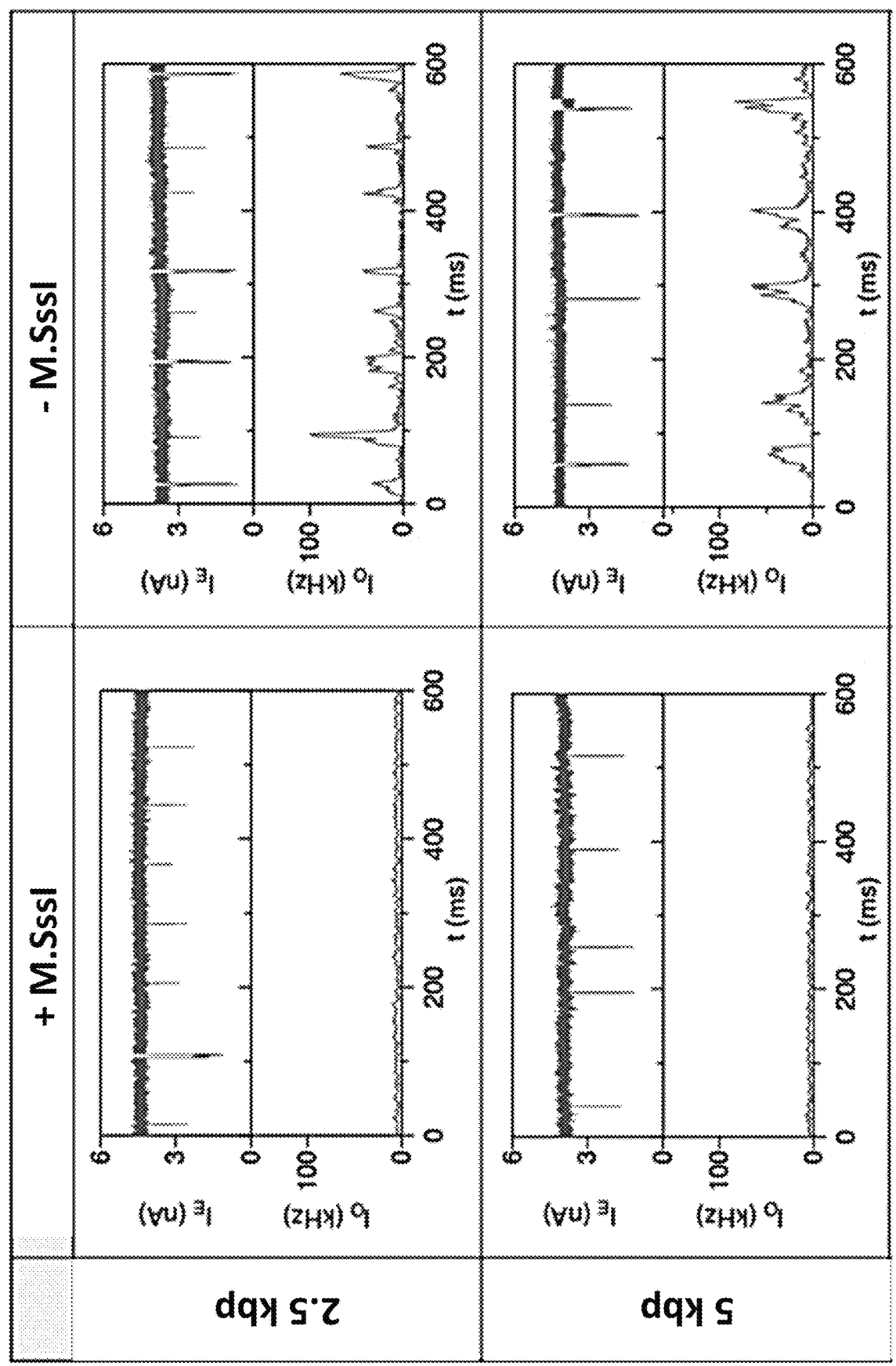
Figure 2E:
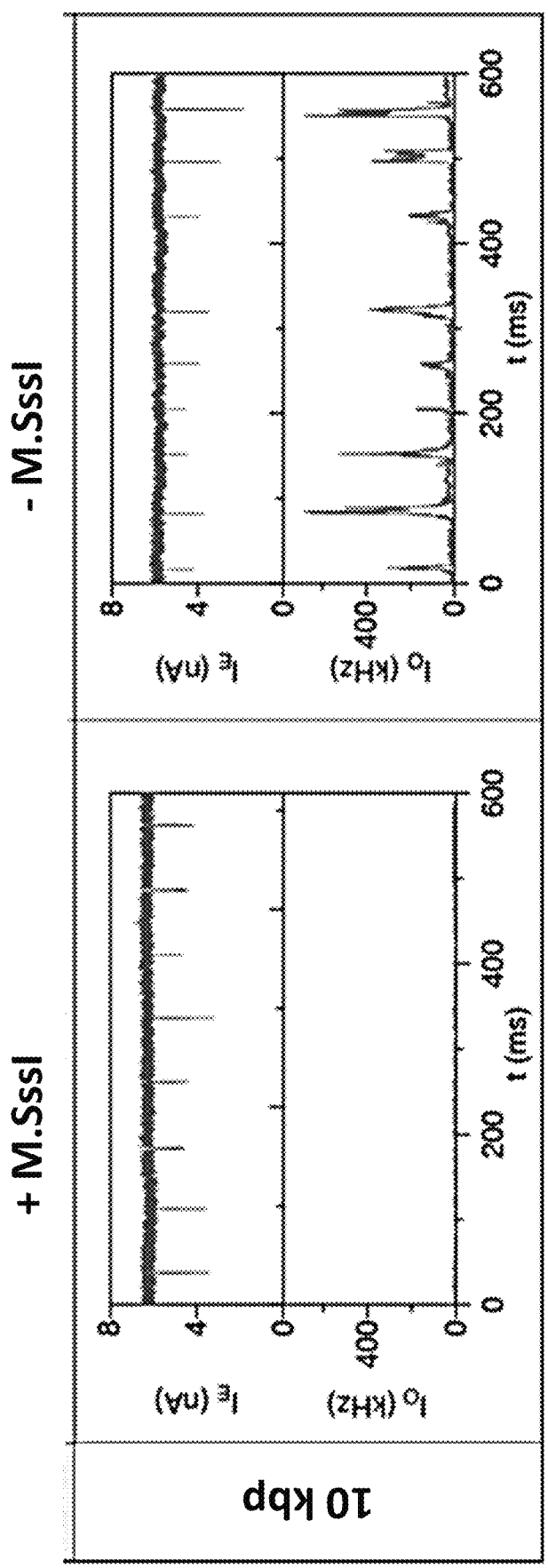

Having validated the enzymatic labeling reaction with M.TaqI and AdoYnTAMRA, we analyzed these six DNA samples using our electro-optical nanopore device. FIG. 2E shows representative electrical and optical nanopore translocation events (concatenated to preserve space) for each of the three DNA model molecules. Each DNA sample was either methylated by pre-treatment with M.SssI (left column) or left unmethylated (right column) as described above. For these experiments we used nanopores in the range of 3-5 nm diameter and laser excitation at 532 nm (120 µW). The alignment of the setup was confirmed by always starting the experiments with labeled DNA, used to fine tune the nanopore location to yield maximal optical signals, and then washing the cis chamber with clear buffer before adding the unlabeled DNAs. Our results clearly indicate that DNA methylation by M.SssI does not affect the electrical translocation pattern, but completely abolishes any photon bursts. In contrast, labeling of the native (unmethylated) DNA results in synchronized electrical blockades and photon spikes, as shown in the right column. A closer inspection of IO for the methylated samples shows that while the optical signals are nearly flat, they are slightly above zero (average value). We attribute this small background intensity primarily to photoluminescence contribution of the thin SiNx membrane. The background emission facilitates alignment of the membrane to the confocal illumination spot, as explained in the Methods section.

Example 3

The Photon Emission Rate is Linearly Dependent on M.TaqI Labeling

Figure 5A:
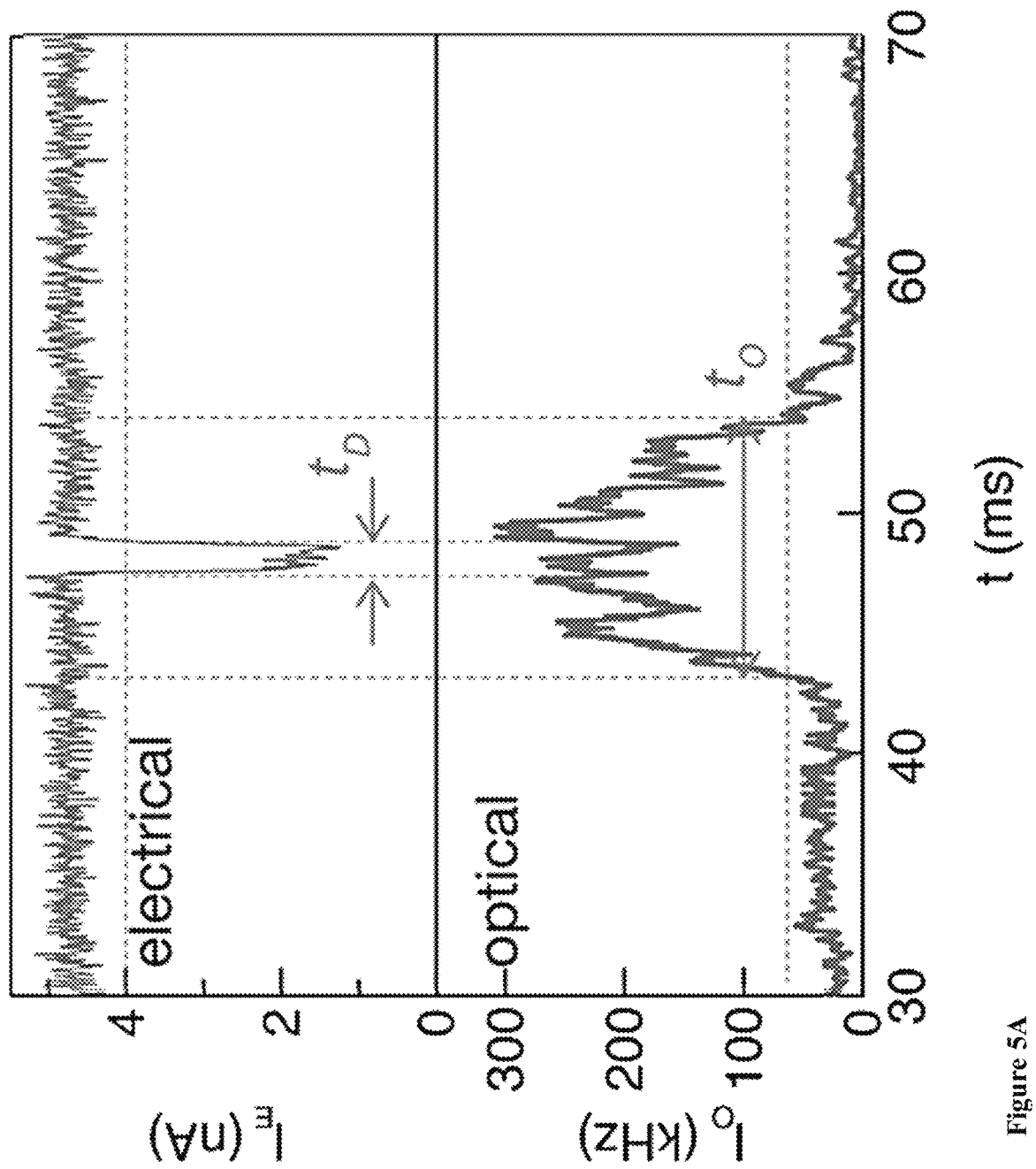
FIGS. 5A-E: A detailed analysis of the electro-optical nanopore signals and DNA controls. (5A) Zoom-in view of a typical DNA translocation event. The optical signals rise before the DNA enters the pore and decay after it leaves the pore. Threshold values are used to define the electrical and optical dwell times ($t_D$ and $t_O$, respectively). (5B) Histograms showing the distributions of $t_D$ and $t_O$ measured for the three DNA lengths. The number of events is indicated in each case. The data was approximated by exponential tail-fits to the histograms. (5C) Scatter plot of fractional blocked current versus dwell time for the methylated (+M.SssI) and unmethylated (−M.SssI) samples. Unlike the optical signals the electrical signals show no significant distinction between the same length DNA samples. (5D) Representative electro-optical events of DNA (methylated and unmethylated) containing either 6, 7 or 21 M.TaqI sites (2.5 kbp, 5 kbp and 10 kbp, respectively) as indicated either for unmethylated (−M.SssI, top) or methylated-(+M.SssI, bottom). (5E) Semi-log histograms of the normalized photon count during the electrical dwell-time for the three DNA length. In each case both the methylated (+M.SssI) and unmethylated (−M.SssI) samples are compared, showing at least 5× contrast. The photon background histograms prior to DNA introduction are also shown in grey. Data are fitted by single Gaussian functions.
Figure 5B:
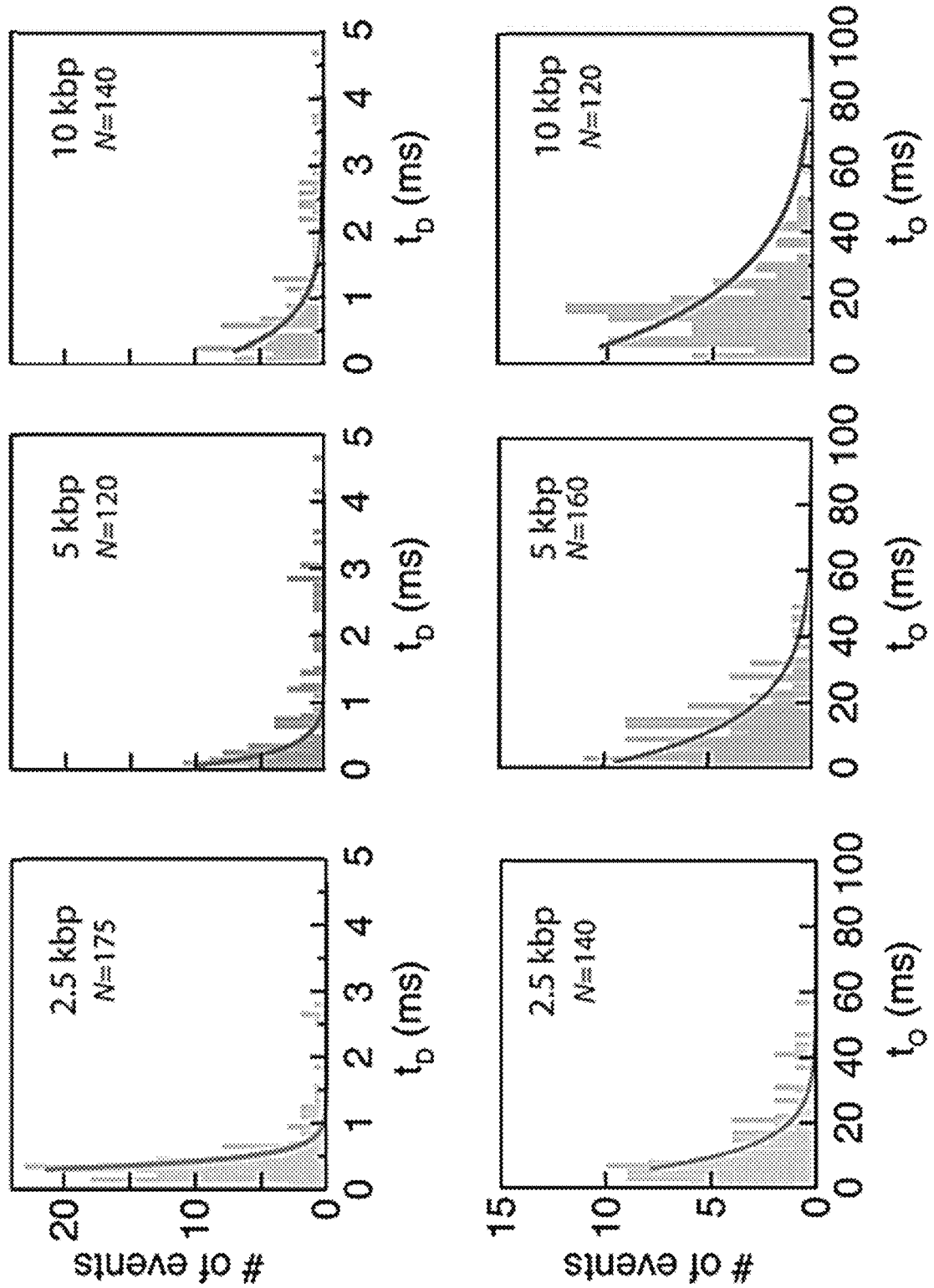
Figure 5C:
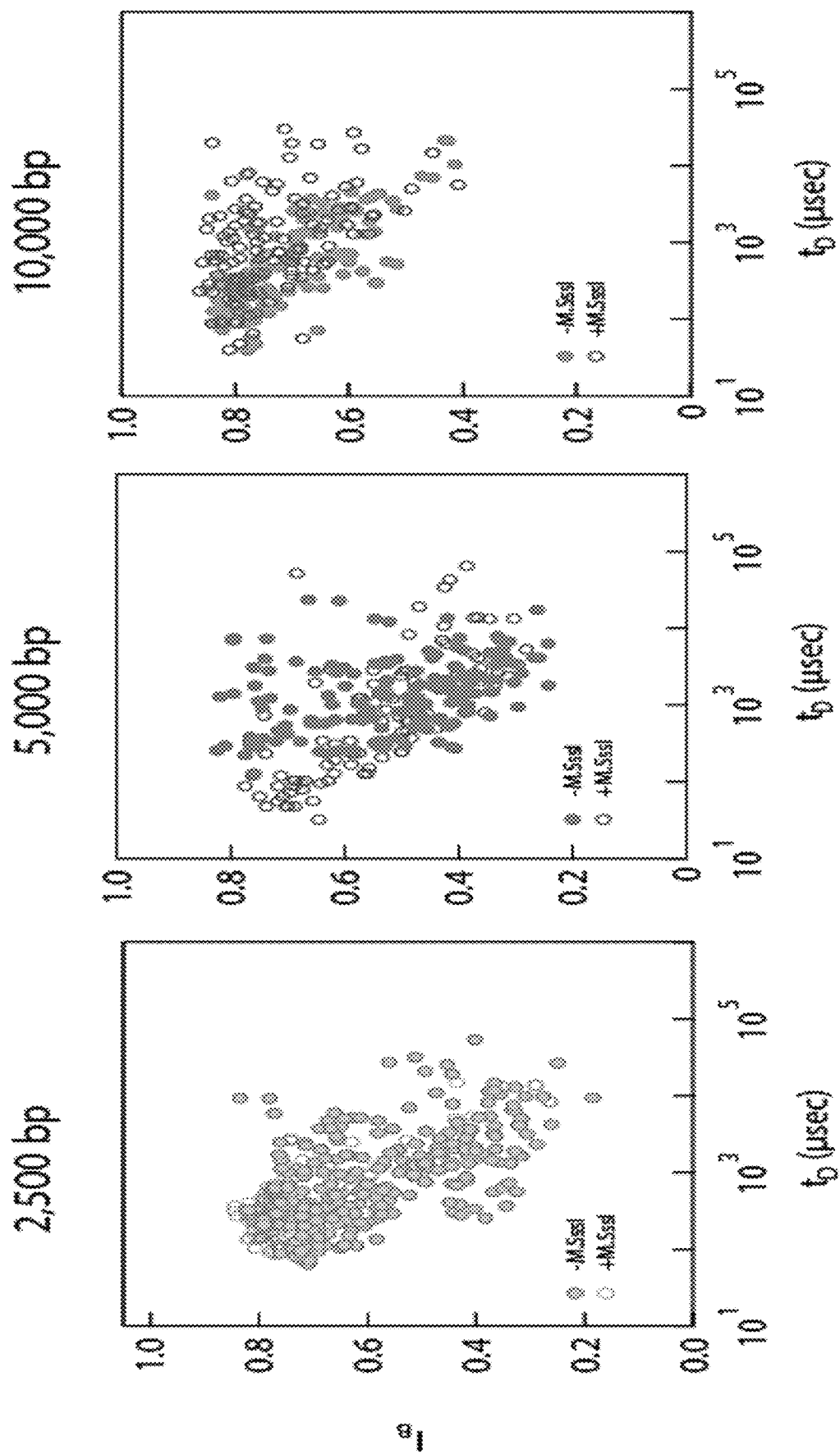

To further quantify the electro-optical signals in our nanopore apparatus we collected about 150 translocation events for each of the six DNA samples and performed detailed analysis of the data using a custom LabVIEW code. The ion current amplitude and the photon rate were extracted by applying two separate thresholds to the data, each one with 3 standard deviations either below the open pore current or above the optical background, respectively. These thresholds were used to automatically define the electrical dwell time of the DNA in the pore (tD) and the optical event length (tO) as shown in FIG. 5A (see Methods for details). Since the illumination volume (defined by the confocal spot) extends beyond the nanopore membrane, we expect that always tO>tD. This expectation is borne out by our data: in FIG. 5B we show the corresponding histograms of tD (top, methylated DNA) and tO (bottom, unmethylated DNA). Electrical event diagrams of all six samples are shown in FIG. 5C. The translocation dynamics were approximated by exponential tail-fits to the histograms yielding the following values: 158±11 μs, 240±32 μs and 540±76 μs for the methylated 2.5 kbp, 5 kbp and 10 kbp DNA, respectively. In contrast the total optical dwell time, which includes both the diffusion-drift time of the molecules in the vicinity of the pore as well as their translocation time, were more than an order of magnitude longer: 10.1±1.3 ms, 13.9±1.6 ms and 17.4±1.8 ms for the labeled 2.5 kbp, 5 kbp and 10 kbp DNA, respectively. We can take advantage of the longer optical timescales. Specifically, this offers two important benefits: (i) since the diffusion-drift dynamics of the DNA near the pore has much weaker dependency on the pore diameter than the translocation dwell time, we expect that tO is less influenced by the pore diameter or its shape, as compared with tD which is strongly affected by pore properties. (ii) The longer optical dwell time effectively increases signal integration and therefore can be used to improve the SNR (signal to noise ratio) of the optical sensing.

Figure 5D:
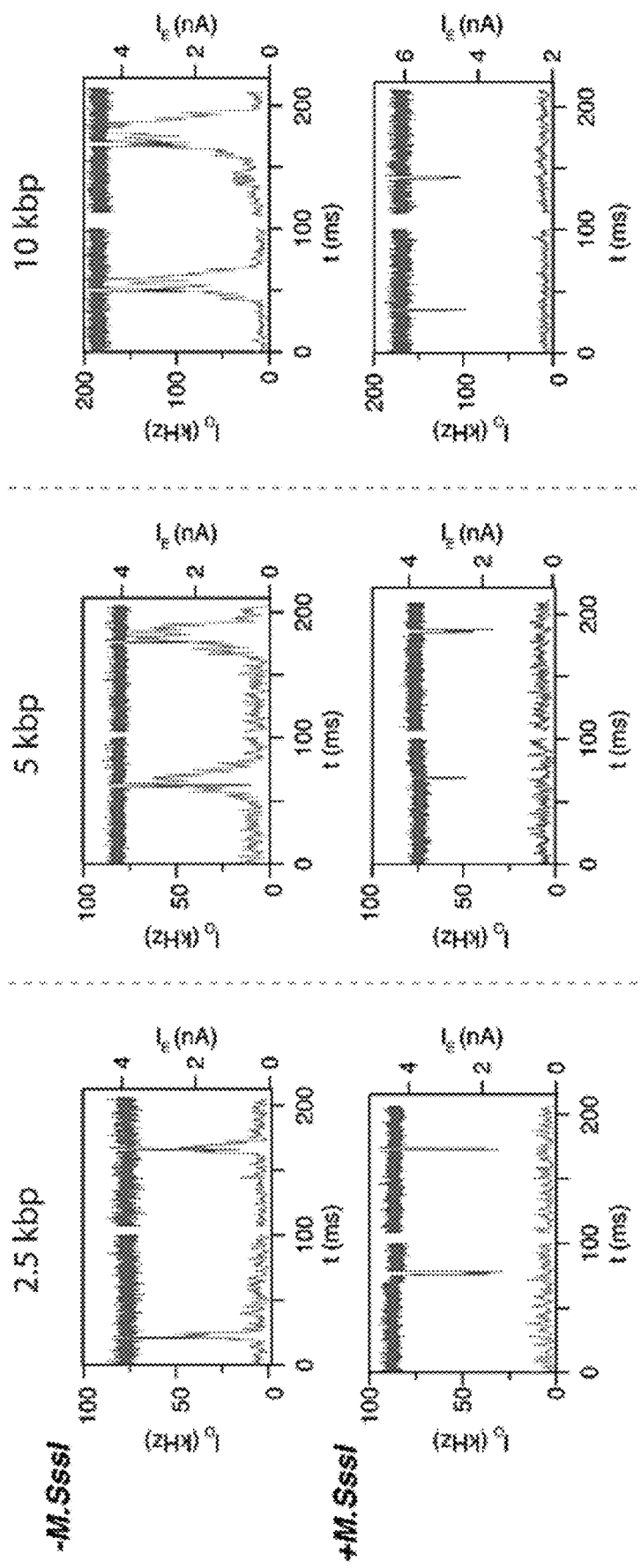
Figure 5E:
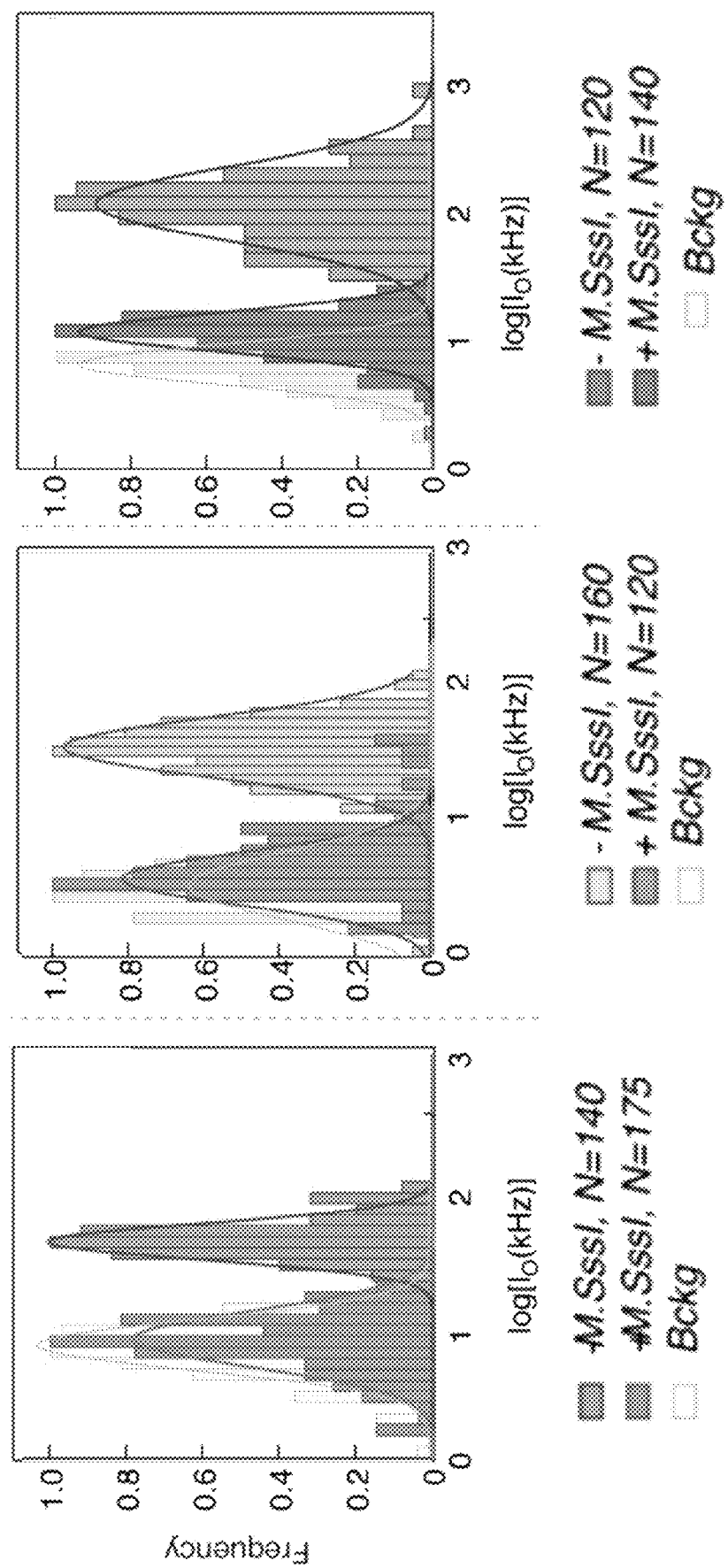

Comparison of representative electro-optical events of DNA containing either 6, 7 or 21 M.TaqI sites (2.5 kbp, 5 kbp and 10 kbp, respectively) is shown in FIG. 5D. We observe two salient features: 1) The amplitude and dwell-time of the optical signals clearly increases with increasing number of M.TaqI sites and length of the DNA. 2) The fully methylated ("+M.SssI") DNA did not produce an optical signal, as expected. To quantitatively compare the fluorescence signals between the methylated and unmethylated molecules, we extracted from each event the total number of photons that were detected during its transient in the nanopore (tD). Additionally, our program evaluates the optical background level for each and every event, before its arrival to the pore to obtain the net fluorescence counts. In order to avoid biasing of the results by the slow translocation events (essentially the tail of the tD distributions shown in FIG. 5B top panels), we normalize each of the events' photon sum by its residence time in the pore. In this way each event contributes evenly to the photon sum histogram. Our results are presented in FIG. 5E as semi-log plots for the three different DNAs, along with the distribution of the background emission obtained in the beginning of the experiment, prior to the addition of the DNA sample. The data were fitted with a single Gaussian function for each case, allowing us to quantify the peak values of our statistical data sets (Table 1). From this analysis we can define the optical signal gain as the ratio between the peak of the unmethylated sample and the methylated one. The values that we obtain for the three DNA lengths are: ×5.1, ×8.0 and ×9.0 for the 2.5 kbp, 5 kbp and 10 kbp DNA, respectively. Notably, the distributions of the background signals (grey bars and lines) nearly overlaps with the corresponding one of the methylated DNA (except for the 10 kbp methylated sample, which produced slightly higher background, probably due to residual free dyes remaining after the nanopore alignment).

TABLE 1

Fitted values for the semi-log plots for the three different DNA samples

| | log $I_{max}$ | | |
|---|---|---|---|
| DNA | −M.SssI | +M.SssI | Background |
| 2,500 | 1.52 ± 0.18 | 0.82 ± 0.29 | 0.77 ± 0.26 |
| 5,000 | 1.51 ± 0.31 | 0.61 ± 0.34 | 0.58 ± 0.28 |
| 10,000 | 2.05 ± 0.41 | 1.09 ± 0.21 | 0.76 ± 0.30 |

To establish a direct, quantitative correlation between the optical signal in each event and the number of M.TaqI sites, we corrected each and every DNA translocation event with its own optical background, measured just prior to the arrival of the DNA to the detection volume. This allowed us to measure the net photon sum of each event and calculate the net photon flux of each event by normalizing it by its optical dwell time tO. This normalization was proven to be better than normalizing by the electrical dwell time tD (as was done in FIG. 5E) due to the longer integration time. Furthermore, it produced results that are practically insensitive to the exact nanopore size or membrane thickness. This insensitivity is significant since it is well known that nanopore size and thickness affect substantially the electrical dwell time and blocked current. Therefore, the optical signals permitted a more robust and quantitative comparison among the various DNA samples measured using slightly different nanopores. Our results are presented in FIG. 4 and Table 1, showing the net photon flux histograms for the three −M.SssI samples. The histograms were fitted using Gaussian functions, from which we extract the peak values (Imax) and standard deviations. The inset of FIG. 4 shows the values of Imax for the three DNA samples. Notably, as can be seen in Table 1, the contribution of each M.TaqI site to the overall signal is independent of the DNA sample used, yielding a constant value within the experimental variations of 4.60±0.25 photons/ms and targeted CpG site.

Figure 7:
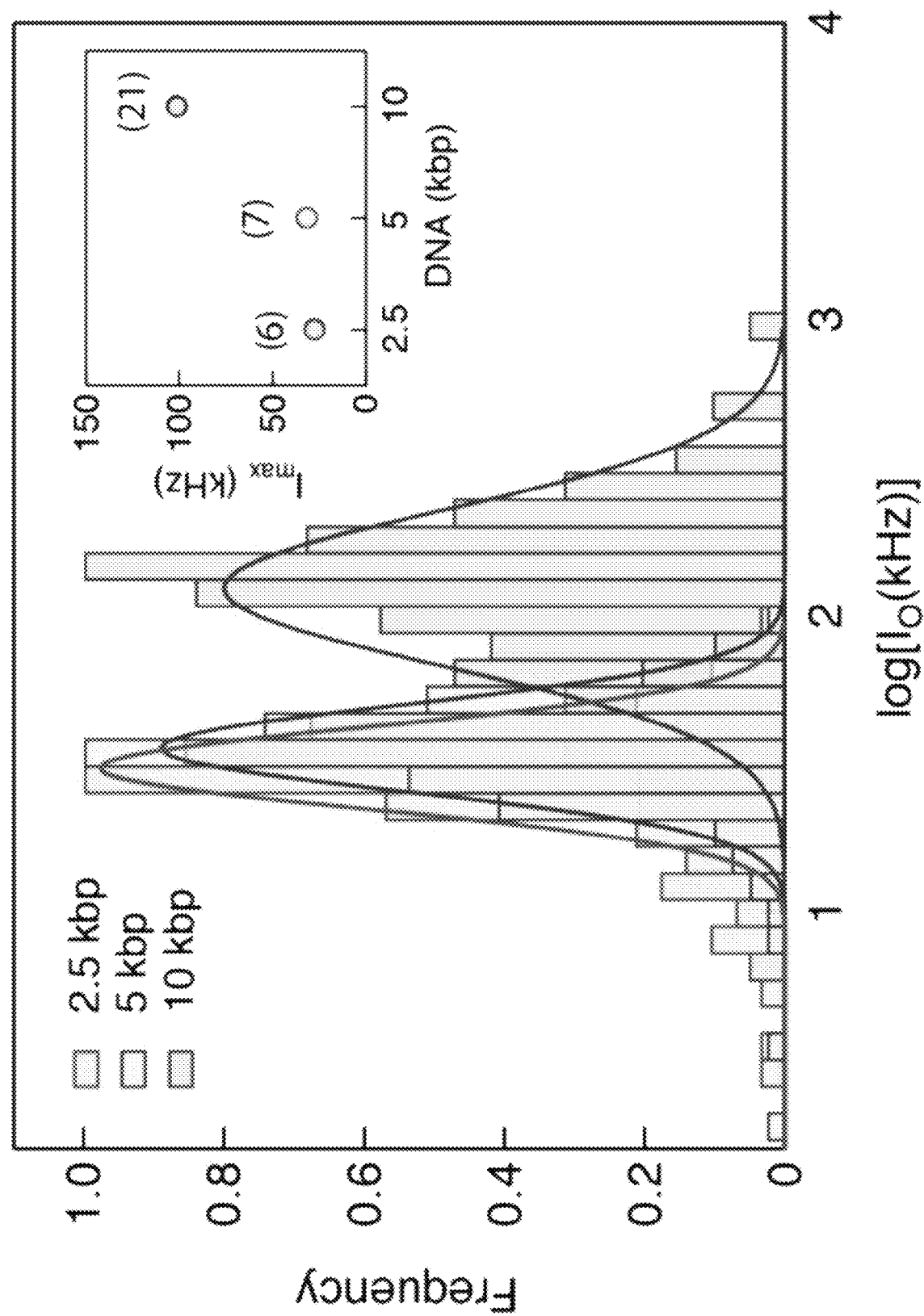
FIG. 7: Histograms comparing the normalized TAMRA photon emission of the three DNA samples, as indicated. Semi-log intensity histograms of the data yield well-defined peaks for the intensities approximated by Gaussian functions (solid lines). The inset shows the peaks ($I_{max}$) of the intensity for the three DNA lengths, also indicating the number of M.TaqI sites for each DNA. Notably, $I_{max}$ scales precisely with the number of M.TaqI sites, not with DNA length (see also Table 2).

The results presented in FIG. 7 and in Table 2 suggest that optical detection of MTase-labeled DNA molecules using synthetic AdoMet analogues can be used to quantitatively measure the number of target CpG sites in random DNA samples. A comparison between the obtained photon count for the 2.5 and 5 kbp DNA having almost the same number of TCGA sites suggests that under the conditions used, non-specific labeling remains negligible as the two fold longer 5 kbp DNA yield identical photon count per TCGA site as the 2.5 kbp DNA, within the experimental error. At the same time the fact that we received constant photon flux values per targeted CpG for all samples support that the DNA samples are, by large, fully labeled. This is also supported by the protection of the DNA samples against fragmentation by R.TaqI (FIG. 2B). Furthermore, despite the fact that the three molecules displayed much different diffusion and translocation dynamics, the photon normalization of each event individually, removed these unavoidable thermal variations, allowing us to establish the electro-optical nanopore sensing as a robust way for single molecule quantification of unmethylated CpGs.

TABLE 2

Electro-optical measurements of the fluorescence peak intensities for each of the TAMRA labeled DNAs, and the intensity per CpG within the M.TaqI recognition sites.

| DNA | # CpG | $I_{max}$ | $I_{max}$/#CpG |
|---|---|---|---|
| 2.5 kbp | 6 | 27.5 ± 1.6 | 4.58 ± 0.27 |
| 5 kbp | 7 | 31.6 ± 1.6 | 4.51 ± 0.23 |
| 10 kbp | 21 | 101.4 ± 2.4 | 4.82 ± 0.12 |

Example 4

Multicolor Electro-Optical Sensing for Orthogonal Site Labeling Quantification

Figure 8A:
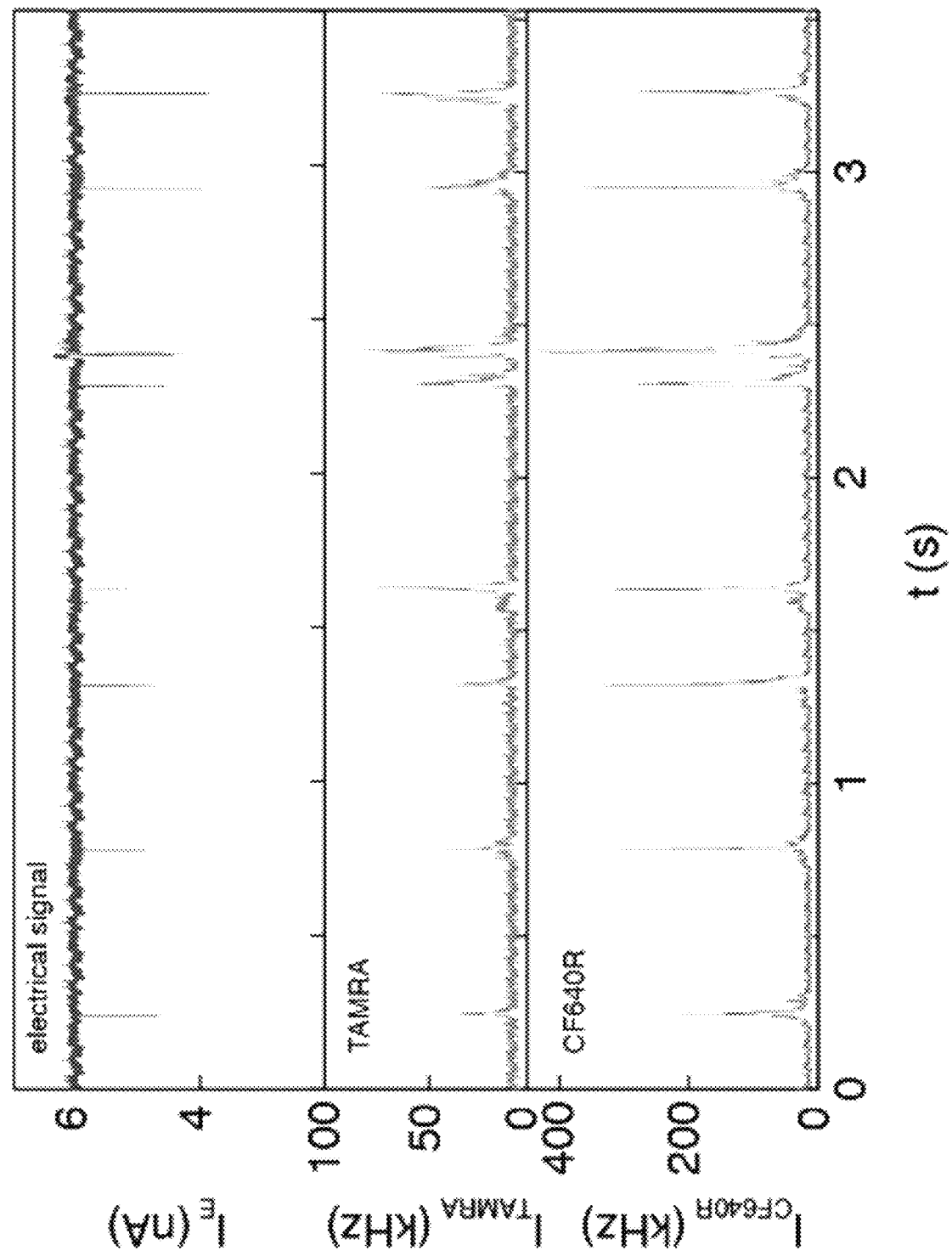
FIGS. 8A-D: Two color sensing of M.TaqI labeled 10 kbp DNA. (8A) Typical electrical (top) and optical (middle, TAMRA channel and bottom, CF640R channel) events. The time between events was removed for display purposes. (8B) Photograph of agarose gel electrophoresis of 10 kbp DNA labeled with AdoYnTAMRA and AdoYnCF640 in the presence of M.TaqI. (left) Gel scan image of the gel using two lasers 532 nm and 633 nm. (right) SYBR Gold staining of labeled DNA. (8C) Histograms of intensity calibration of the green and red channels performed by acquiring TAMRA only or CF640R only labeled 5 kbp DNA events. The two histograms corresponding to the two colors are shown (the number of events is indicated in each case). The ratio of the peak values is used to calibrate the brightness and detection efficiency ratio between the two channels. (8D) Top: the normalized counts scatter plot of 115 individual events. Middle: three representative dual-color intensity traces (indicated by numbers) for different TAMRA/CF640R ratios. Bottom: Heatmap using the intensity calibration to evaluate the number of TAMRA versus CF640R labels on each DNA molecule. Two-dimensional histogram of the data displays the occurrences of DNA molecules with specific TAMRA and CF640R labels.
Figure 8B:
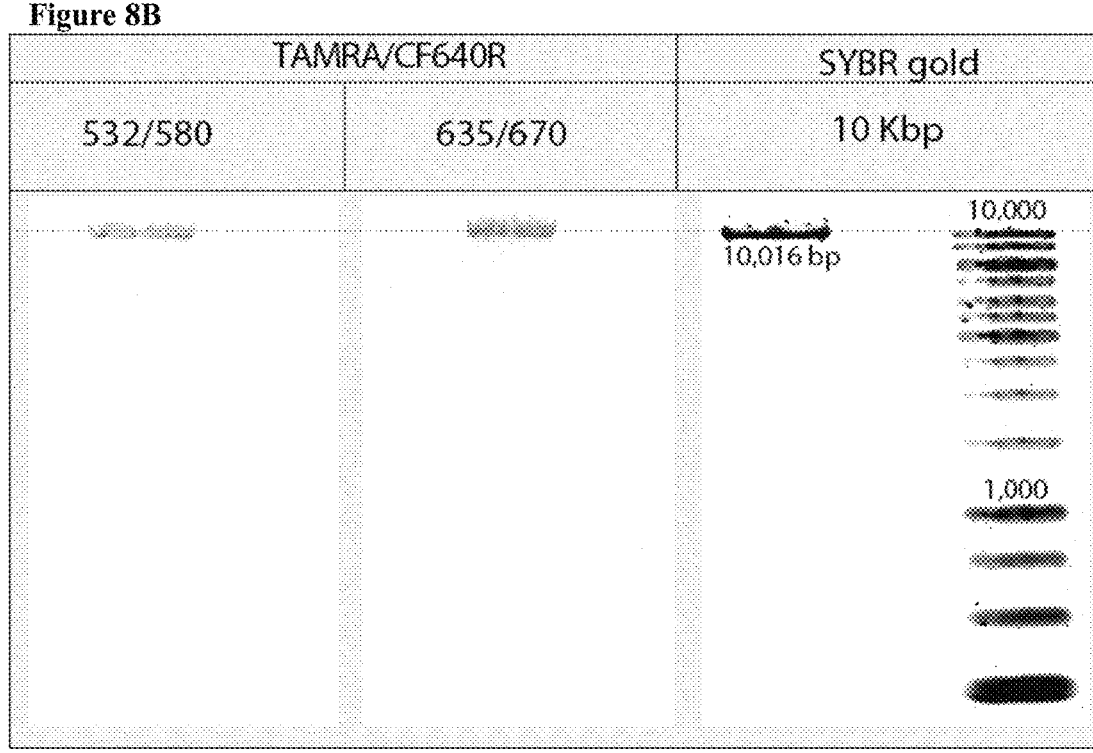

Having established a proof of principle for labeling and single-molecule quantification of unmethylated sites, we seek to further expand the ability of the method for multiple colors. The ability to detect and quantify multiple colors simultaneously may open up the possibility to specifically target multiple, different recognition sequences each one with its own unique DNA MTase and custom AdoMet analogue. In addition, it may permit the co-quantification of DNA methylation with other DNA modifications such as 5-hydroxymethylcytosine or DNA damage lesions, permitting a fully orthogonal labeling method for epigenetic biomarkers. For the sake of proof of principle demonstration, we synthesized an additional AdoMet analogue coupled to the red fluorophore CF640R (AdoYnCF640R). The two AdoMet analogues were allowed to react simultaneously with the 10 kbp DNA (harboring 21 unmethylated M.TaqI sites) in the presence of M.TaqI, resulting in random but complete labeling of the DNA with the TAMRA and CF640R dyes. The DNA sample was analyzed using our nanopore system, excited simultaneously by two lasers (532 nm, 120 µW and 640 nm, 94 µW) and emission was acquired by two avalanche photodiodes (APDs) separated by a high-pass dichroic mirror (cutoff wavelength 650 nm), as detailed in the Methods section. In FIG. 8A we present a representative set of events obtained in this experiment: each electrical DNA translocation events (blue curve) is accompanied by bursts of photons in both the "green" (TAMRA) and "red" (CF640R) detectors, indicating that our samples are labeled with both fluorophores. Bulk gel analysis of the sample (FIG. 8B) confirmed the dual labeling. DNA samples labeled with the two AdoMet analogs (AdoYnTAMRA and AdoYnCF640R) were loaded onto a 0.8% agarose gel. FIG. 8B, left panel, presents a gel scan image in which the sample was excited using two lasers separately: i) 532 nm (filtered using 580/20 nm band), and ii) 633 nm (filtered using 670/20 nm band). The image confirmed that the sample was labeled with both TAMRA and CF640R fluorophores. SYBR Gold staining image of the gel is presented on the right panel of FIG. 8B.

Figure 8C:
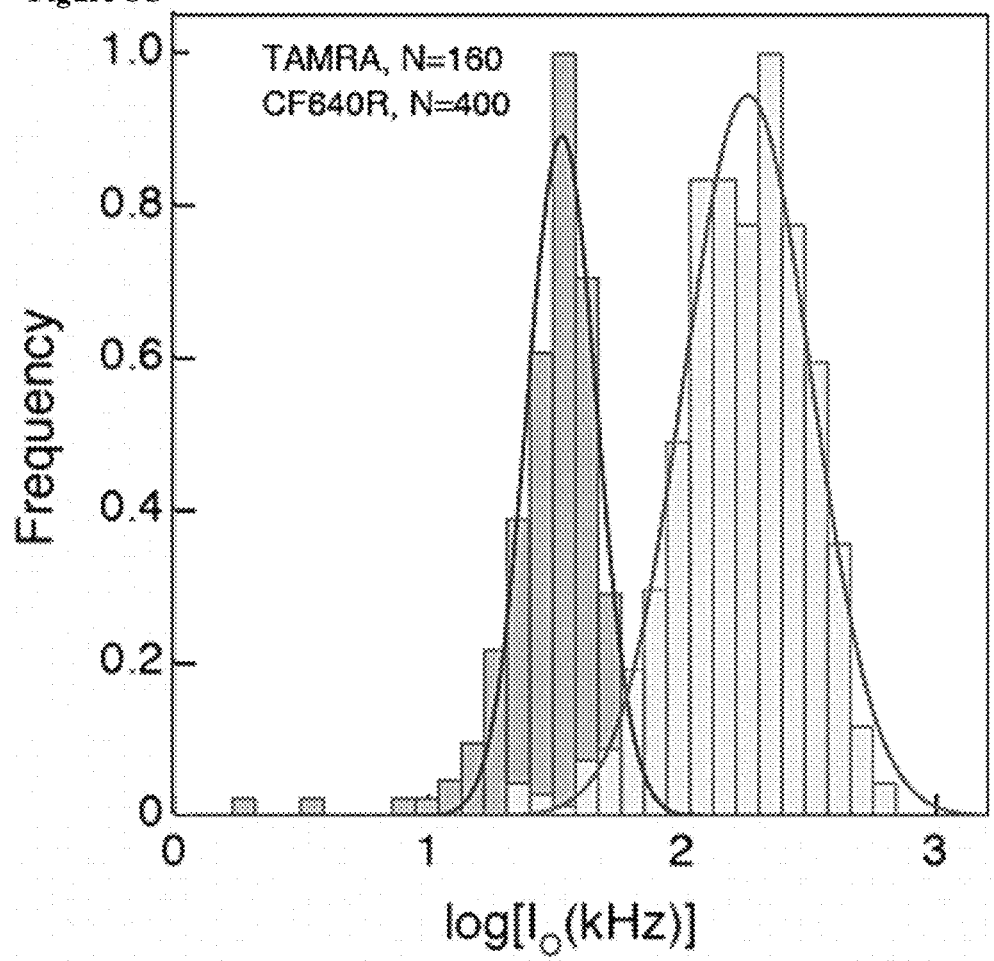

From examination of the dual color translocation events it is apparent that the CF640R photons burst intensities are substantially stronger than those associated with the TAMRA. There could be two possible reasons for this: first, this could be due strong bias in the labeling with AdoYnCF640R over the AdoYnTAMRA. However, this option is unlikely since in preliminary studies we observed that M.TaqI has a fourfold lower activity with AdoYnCF640R compared to AdoYnTAMRA and thus we used an excess of the red over the green cofactor (3:1) in the two color labeling reaction to adjust the two reactivities. Second, which was later confirmed, is that the molecular brightness of the CF640R (multiplication of its specific absorption and quantum yield) and the detection efficiency of its emission path in our electro-optical apparatus are substantially higher as compared with the one associated with TAMRA channel. To calibrate the ratio of fluorophore brightnesses and detection efficiencies between the two channels, we used M.TaqI and AdoYnCF640R to label the 5 kbp DNA fragment as used in FIG. 5A-E, and translocated the sample using a 4 nm pore and excitation laser of 640 nm with intensity of 94 µW (representative events are shown in Supporting Information). We utilized the normalization method discussed in FIG. 7, to obtain net photon flux intensity using the CF640R in the red emission channel. First, we corrected the leakage of the TAMRA fluorescence to the red channel by calculating the ratio between the green and red APDs signals obtained for the translocation of the 10 kbp DNA fragment used in FIG. 5A-E. Next, we compared the TAMRA (green) and CF640R (red) labeling of the 5 kbp DNA (FIG. 8C). From fitting the histogram with Gaussian functions we obtained peaks at 31.6 KHz and 169.4 KHz for the TAMRA and CF640R, respectively. These results allow us to normalize the TAMRA/CF640R counts in the system such that their relative level for each and every translocation event are unbiased by the detection efficiencies or fluorophore brightness and hence it represents the labeling ratio with the two AdoMet analogues.

Figure 8D:
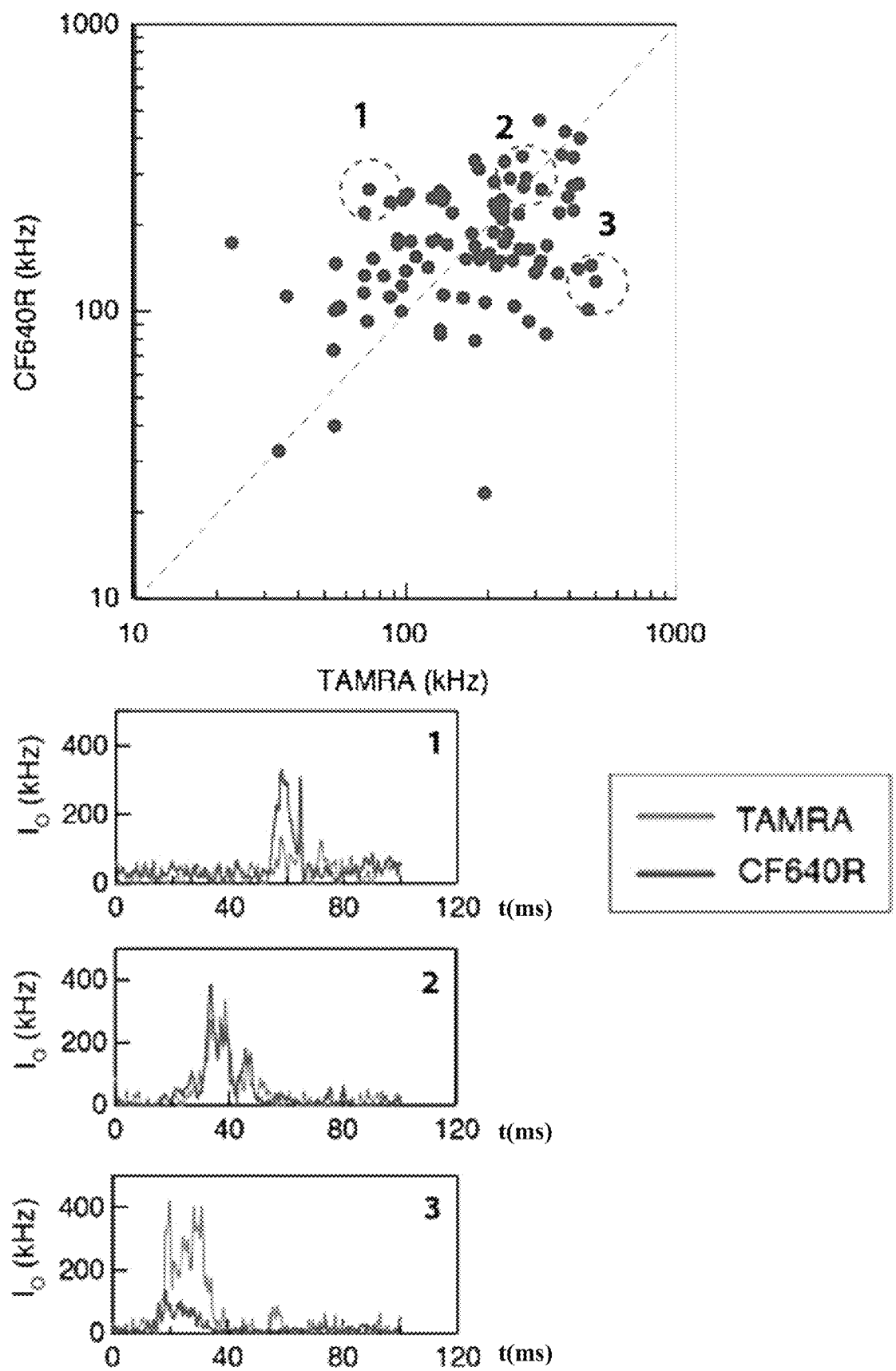
Figure 8D:
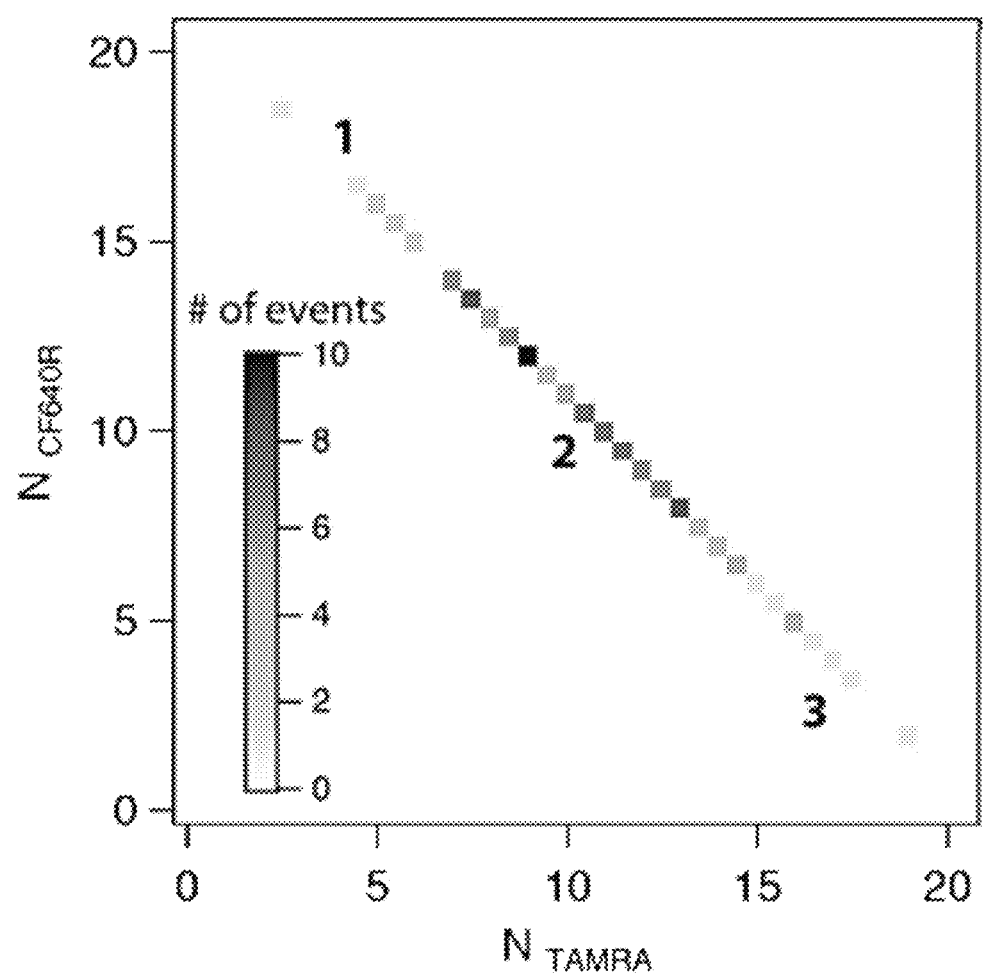

In FIG. 8D we display a scatter plot of the brightness/detection efficiency corrected distribution of the randomly labeled 10 kbp DNA. We first note that most of the events fall around the diagonal line showing that on average, the DNA molecules are equally labelled with AdoYnTAMRA and AdoYnCF640R. Three representative two-color optical events from different areas are shown illustrating either heavier CF640R labeling, almost equal labeling and heavier TAMRA labeling (indicated by "1", "2" and "3", respectively) are shown. Notably, with the corrected intensities of the two colors we can calculate the number of AdoYnTAMRA and AdoYnCF640R in each translocation event. This data is shown as two-dimensional histogram (FIG. 8D, bottom panel) where the color indicates the number of DNA molecules in our data with the specific numbers of the AdoYnTAMRA and AdoYnCF640R labels.

Example 5

Expending the Technique to Allow Epigenetic Modification Detection from More Sequences Using Optical and Electrical Detection Additional MTases can be used in order to target and detect methylation patterns in different sequences in parallel. A few examples are presented in Table 3:

TABLE 3

| Name | Organism | Recognition site |
| --- | --- | --- |
| M.BseCI | *Bacillus stearothermophilus* | 5'-ATCGAT-3' |
| M.EcoDam | *Escherichia coli* | 5'-GATC-3' |
| M.HhaI (tm) | *Haemophilus haemolyticus* | 5'-GCGC-3' |
| M.MpeI (dm) | *Mycoplasma penetrans* | 5'-CG-3' |
| M.SssI (dm) | *Spiroplasma* species | 5'-CG-3' |
| M.TaqI | *Thermus aquaticus* | 5'-TCGA-3' |

Figure 10A:
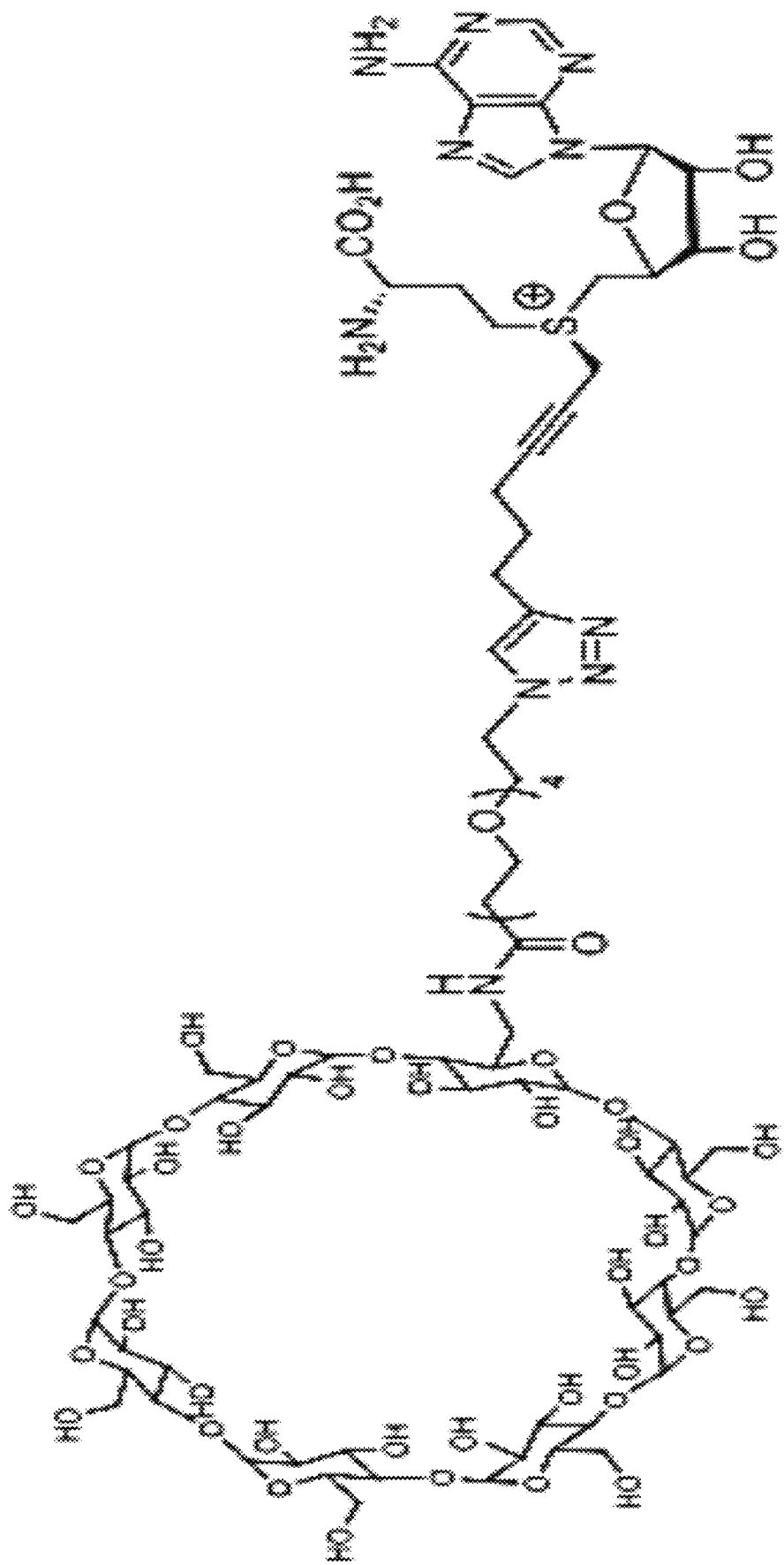
FIGS. 10A-B: (10A) Gamma cyclodextrin structure. (10B) Photograph of an agarose gel electrophoresis of 1994, 3532 bp DNA labeled with cyclodextrin in the presence of M.TaqI. Samples were treated with R.TaqI to confirm the labeling.

In addition to the of fluorescent AdoMet analogs that have been described, and were detected using the optical signals, different AdoMet analogues can be used which contain either a different fluorescent probe, or a bulky group that can be detected electrically. One such example of a Steric S-Adenosyl-L-methionine (AdoMet/SAM) analog is AdoYnCD (gamma cyclodextrin, see FIG. 10A)

This glucose ring has a molecular weight of 1700 Da and a diameter of 1.7 nm and therefore it creates a distinctive ion current blockade on top of the blockade of the bare DNA passage through the pore. Due to its small size, it yet permits detection in small-thinned pores, increasing the spatial and temporal resolution.

For the labeling procedure, we use the DNA MTases to catalyze the transfer of a gamma cyclodextrin from the synthetic cofactor AdoYngCD onto the adenine or cytosine residues within the MTase's recognition sequences.

Figure 10B:
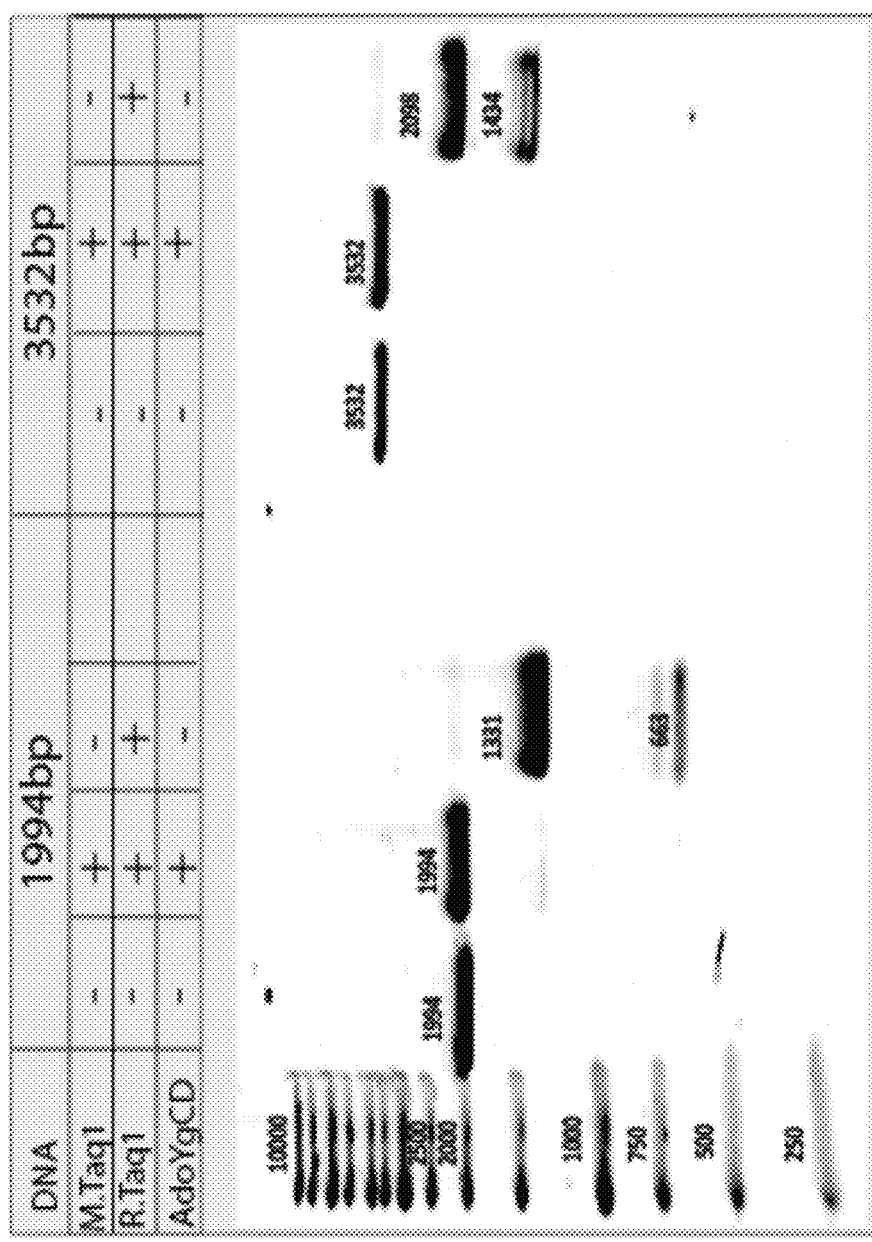

For the proof of concept of detecting gamma cyclodexterin-labeled DNA through nanopores we labeled 1994 bp and 3532 bp PCR amplified DNA having one M.TaqI unmethylated site with cyclodextrin. For validation of the labeling, we performed agarose gel electrophoresis analysis. We took advantage of the fact that the cognate restriction endonuclease (REase) R.TaqI cleaves unmethylated 5'-TCGA-3' sequences but does not restrict the DNA if the adenine within the 5'-TCGA-3' sequences is modified. Therefore, the cyclodextrin labeled sample is not digested by R.TaqI while the unlabeled sample is cleaved (FIG. 10B). The labeled and unlabeled DNA samples were treated with R.TaqI and then loaded onto a 0.8% agarose gel together with DNA samples that were not labeled or treated with R.TaqI. FIG. 10B, presents a SYBR gold staining image of the gel. This result confirm that the sample was completely labeled (R.TaqI didn't cleave), with cyclodextrin.

The advantages of using this glucose ring over other nanopore techniques which uses other bulk groups such as Streptavidin, MBD proteins and KZF are: 1) It has smaller size (1.7 nm instead of 5-6 nm) and therefore it provides better spatial resolution, allowing us to label denser unmethylated sites. Moreover, we can use smaller size pores which provide better temporal resolution. 2) Unlike proteins, it has no electrical charge and therefore is independent on the PH of the buffer and more importantly free cyclodextrins don't translocate through the pore.

Example 6

Methylation Quantification in Tumor Suppressor genes and Oncogenes

PCR-amplified DNA fragments of oncogenes and tumor suppressor genes, which contain multiple recognition sites for M.Taq1 MTase (5'-TCGA-3') and M.HhaI (5'-GCGC-3') MTases, were labeled with Atto532 and CF640R fluorophores. For the two-color labeling procedure, 5 ug of DNA is first treated with AdoYnAtto532 and suspended with M.HhaI buffer (containing 50 mM Tris-HCl, 5 mM β-ME, 10 mM EDTA, pH 7.5@25° C.). The reaction contains 0.01% by volume Triton 100-X, 100 µg/ml BSA, 40 µM of AdoYnAtto532 prepared in house and 2.59 µg of M.HhaI MTase. Reactions are performed at total volume of 50 µl for 3 hrs at 37 oC. Then, 50 ul DDW and 3 ul glycogen are added. To remove the unincorporated AdoMets, we perform ethanol precipitation using standard protocols. After washing the pellet 5 times with 70% ethanol it is vacuum dried and re-suspended in 40 µl of DDW. Then, the second labeling procedure is performed similarly. This time the 40 ul of the DNA labeled with Atto532, is suspended with NEBuffer 4 (New England Biolabs, containing 50 mM Potassium Acetate, 20 mM Tris-acetate, 10 mM Magnesium Acetate, 1 mM DTT). AdoYnCF640R prepared in house and 2.59 µg of M.Taq1 (3.7 µg/µl) are added as well. Reactions are performed at total volume of 50 µl for 3 hrs at 65 oC. Reactions are stopped by adding 40 µg of proteinase K (20 µg/µl) (Thermo Scientific) for 1 hr at 45 oC. We then repeat the ethanol precipitation and the pellet is re-suspended in 20 µl of DDW for UV-Vis absorption quantification.

Figure 11A:
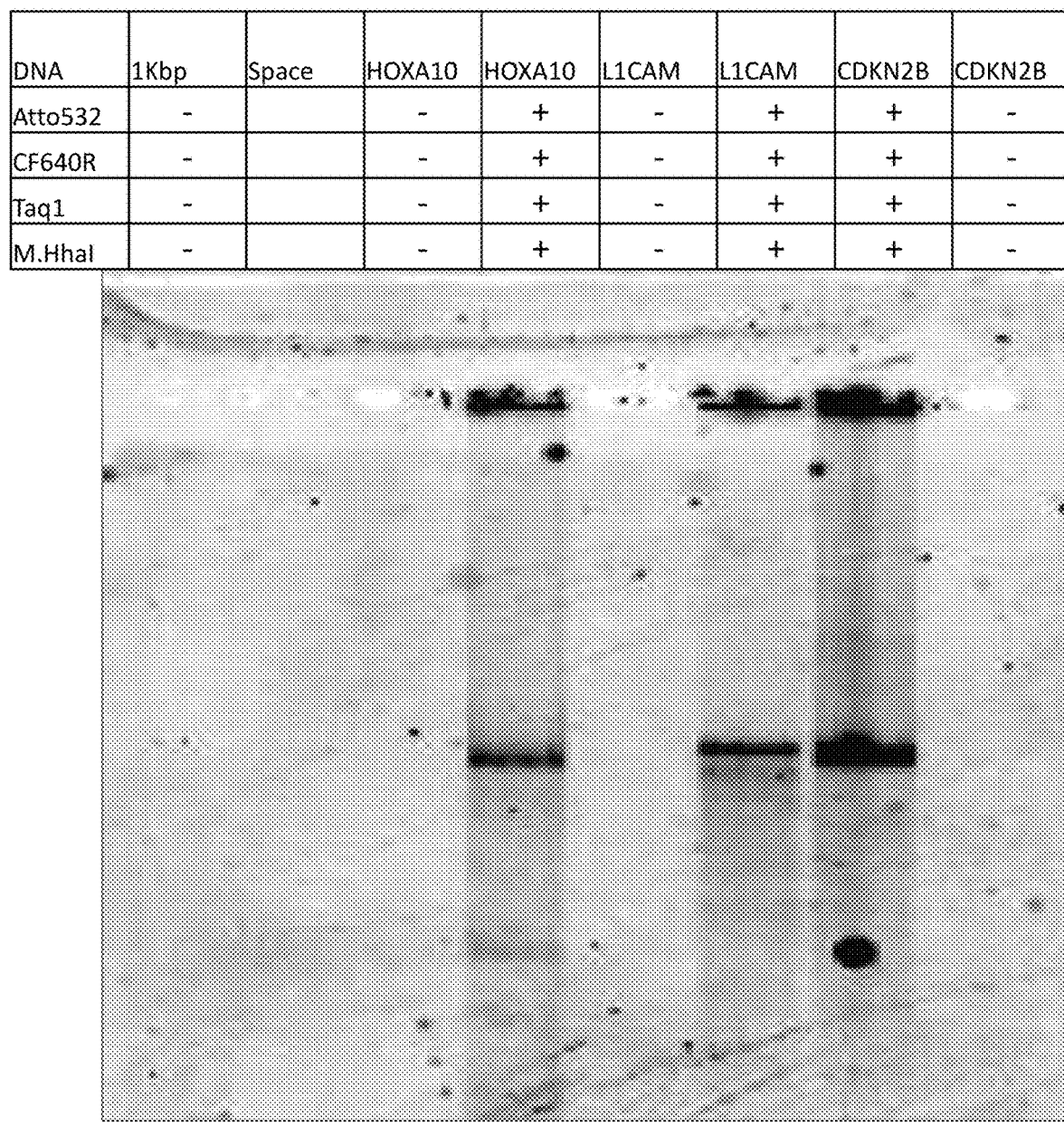
FIGS. 11A-C: Photograph of agarose gel electrophoresis of HOXA10 (4330 bp), L1CAM (5240 bp) and CDKN2B (4661 bp) labeled and unlabeled DNA (in the absence of M.Taq1 and M.HhaI MTases). (11A) Gel scan image of the DNA. Fluorophores were excited by a 532 nm laser and filtered at 580 nm. (11B) Gel scan image of the DNA. Fluorophores were excited by a 635 nm laser and filtered at 670 nm. (11C) SYBR Gold staining of labeled DNA and unlabeled DNA.
Figure 11B:
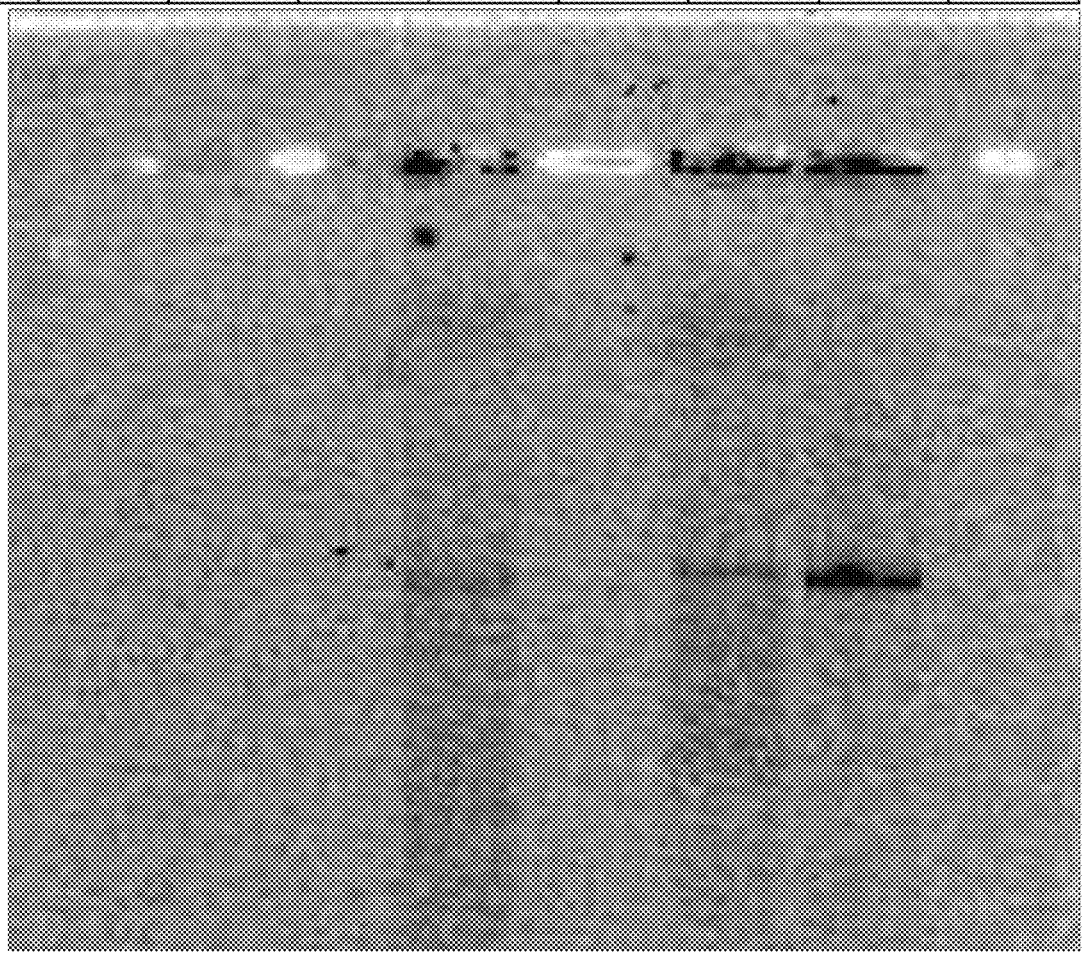
Figure 11C:
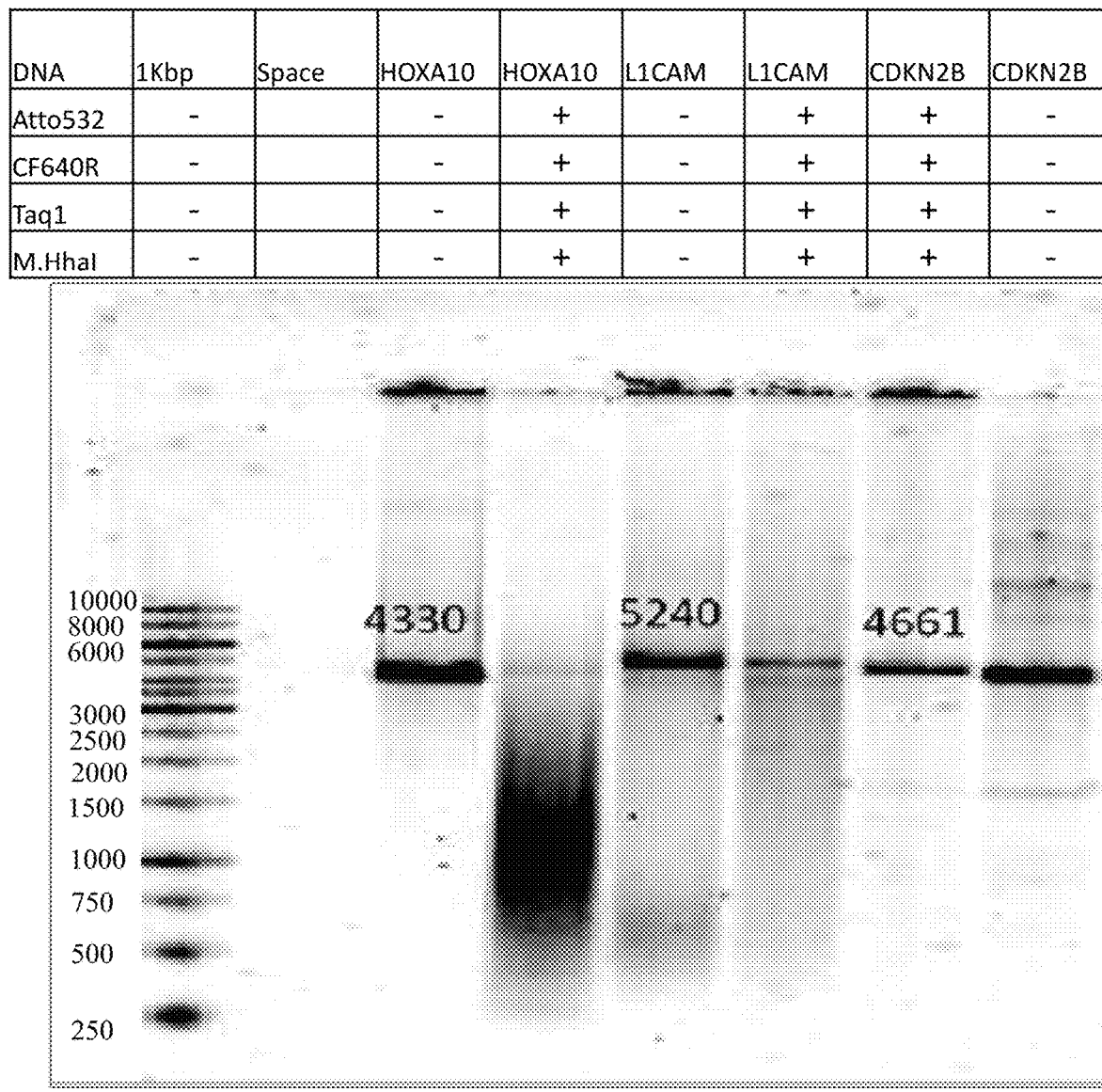

In FIGS. 11A-C we presents an Agarose gel of L1CAM and HOXA10 oncogenes, and the tumor suppressor CDKN2B, labeled with Atto532 by M.HhaI and CF640R by M.Taqq1. For the gel, about 250 ng of DNA were suspended with 2 µl of 6x electrophoresis loading buffer (50 mM Tris, 60 mM EDTA, 60% glycerol) in a total volume of 12 ul DDW. Samples were loaded on 0.8% agarose gel and allowed to run for 90 minutes at 100 Volts. The gel was imaged using a 532 nm (FIG. 11A) and 635 nm (FIG. 11B) laser gel scanner, followed by SYBR Gold staining (30 min.) (FIG. 11C). The sequences of the genes are presented in Table 4. The coding region is provided in capitals.

TABLE 4

| Gene | Sequence |
| --- | --- |
| L1CAM | gctccggaattcttaccccctccattttgcttcctcgcctgtgaggtcatggccttgagcctaggaggggggca |
| | ctggggaggagctccttccttctcgatcctgtgcagggctgcgggggagagtgggagagagtggagtcgg |
| | cgggaaaggtcgaatggggccaatcccgaggacaaagaaataagacaccagagagctggaggaaaatc |
| | tgggagttggggggtggcagttcgagggataccctctcccagaccctgtctccccctgggctcgcctcctaccc |
| | tgccgcccacctgggctctggggtgcgcaggagccggtgctccgcggcgcctccccaacacgctgagga |
| | cgaagccccgcaccccctcccaacaggaccctgactgggccctcaggatcgggggggcattcgggagag |
| | gtcccggagtcctgccctgtgtgtgtgtgttggggggggcgttgcgtgcaggtgccatcgctggccggcg |
| | ccgtcgagggccaggccgaggctaagggagcatccccttccttgccggactcctctctccaccgcccggc |
| | cccaggcctctgggagcactctcgccccgcgattcccgctccgagctttcacagcgggctcccttgcgctg |
| | gggctgaggacactctccggccggagactcccggtctgcggggaagggggtctggcgggacccgtcgg |

TABLE 4-continued

| Gene | Sequence |
|---|---|
| | ctggggtcccgctgagctcccggagtgggctgcccggggcccccagcccaagccgcgctcggctggc |
| | accaggggctagggtgcggcggggcggggcggggcggggcgggcggccggggaggtgatctcactc |
| | ctccctccctctcctcccggcgctccctcccccgccctgcgcgcacgcccgcccgccccgccacag |
| | ccgctgctgccgcagcatcggcatcgcagacgcgctcgggcggcgggtccgaggccggcgtgcgcgg |
| | aggctgggcgggcagcccgagcggtggccgagcgcaggtaaggcgggctggcctcccgtgcgacc |
| | cgggccgcggccgcgatccccggcgacaccacaccgctctgccggggtgcacggaccagggagtc |
| | ccggcccggtccggcccgcggtaaccggcgttgctgccggagcccacccatgccgggcgtcgggctc |
| | cgggcaccgcgggctgtaagcggggcggggagggatgcccgggtgcccgagcccgacaggtgaggg |
| | gtaacctgcggggcccccagatgctggcctgggcgggagaacagggcggggggcgtcaggcagggtct |
| | gtgtgggcaggcgggggctgaagttggcgggtcccgtgcgtgtgtgcgtgtctgagaaaggaagccag |
| | atcgggtcgagcgctcccccacaggccgccgtggggtgtggccctgggcgtggctgccctcatcccca |
| | gccgagagctcagtttggttgaaaatcccggctgacagcgtggtgagggggtagatcgggataagccgccc |
| | ctgcaatggggggagggagtgaacgggactgggcgctgcctgcccctccgccccaaggttgggggg |
| | ctttgttctcctccttcttctttccaaatcccagcctgggctcctcgggctcacccgaaaacctgccgcagag |
| | ccaggggctcctccccggaggcgtagggcgcctctggagcccgtttccacaggctctgtggccagtcagg |
| | gctggagtgggtgaggtcggttcgggcacccactgctgtgcctcccgtgcatgggtgtccatcaggtaggg |
| | tccatcaggtaggggtgagggaaggtgggcctcactggctcaggcggtccctgcgcactgcaggtctttg |
| | cccactgccacatcttcctatctctgtgcggttatgggagggtcagcgattcctattccctccattccaggtca |
| | gactttttggggcctcttggttggcagggattgcaaagaacacgcactacaatccattgcccccgacagggta |
| | tctggaccccccacctatcactgtccctctcaggaaggcaggcctagagccatctgcccccttctccagaag |
| | gagtgggggcctggcacccccaggtagatacccctgccccctgttaaccccaccctgagggcaggggcat |
| | cggggcagcccagtgccatctctgctgactcatgtgggcctgacgtaaatcagtgcagtccgcccttcttccc |
| | ctggggctgctgcccagcatcatctttctggggcgggggcctcccagggcctctcccctccccgtcagct |
| | ccttgctgcaggtggtgggacttggcccagcctggcctctccccctggcacagctcccatgcagtgcccacat |
| | gtgcacacctgagggctccagagcctttgaggactcggctgtcttggccacatgggaagtttggggcaggg |
| | ttgggcctgggaccttcccacctccttggctcctggtcatttctctctgctgcatctgagtctctctccatatttatt |
| | gatgtttgtgtgtgtatgatcccgaaagtaatacatcttattgtaggacacttgaaatatacagaaaagaacaaa |
| | agaaattaagaatcgctagtgatctgatcaccaagagggaaacacgttcagcacgccccagcctccctggtt |
| | tgctacaccgcgctcctaaaaggctcctcccaagttcccagctgccagctccctgctgagcatcaggagg |
| | acaatcagcgcttcaaggtggcggggtccctgccctgcagccagtgaagagcttccctacccaggcgct |
| | caggatcccagcgatgggcagtcgtgtactgggcagctgctcatggccagtgctccttgggccgggctct |
| | gggctgcccatggaagagccagtgacaaactggaccagcattgtccctgtcttcgtgggggtgtcacttgtttt |
| | ctttttttcttgatgattatctgaagggaaaagggaggcaaagagtgaggaagggcctggcctgagggctcct |
| | acagtgagcagggtgcccagattgtgccccaatcggcctctcccaggtccgagcccttccaccactgga |
| | actacagctggcgccttccttggcatgcacctggccaggactggcaggtgagggtcgaggagacaggcct |
| | gtgtgccctaccttgatcaccaagttccctttcaaagctcgaaatggctgcactgagtgcttttctgggtgtgag |
| | ggtgatgcggcctcgcagagtggcccaggctccaggagggcacgttcatgggagaacctggggtagtgg |
| | tggggtcctgtgaggaggtctgccaggatggggatcccagccaagaccctggtctgccaggcatgagtgg |
| | gggcatgagtgggggcctgcctccctccctcgtggttcagacagtgggggaggcgggggggtctggatg |
| | ccctctagggtccccagcagggtgctcattgcctgtcctctgccccgtgcaatgggctggggctgggtccc |
| | tgggtggggccatctggaatgggcctgcagcatccctgcccctgcagtcgctgtcttacttgctctgatctgg |
| | cccatctcggacacctccttctcctgcttccccgcccccctgctctctcctctgcagcctcccacgtctccct |
| | gtgccccaccccagggccatcaccttcctcctccttctaggcagaagcctgctgctgccggggatgggt |
| | gcaccactcccgctctcctccctctgcctgcctgccccttccctcttcccccttcccgtcaggg |
| | ctctgctccatctctctgcttacccttttgtctgtcttccaccgctctgctcctctcttgtcccccccagctgccc |
| | ctgcctcacccttgagggccctgaggttgtgccctgtccagcagccactcagcacccttctgctggactctac |
| | gccttggggttgggcccagaccccccatgggggccttgtctgagtggaaggctgtatgggggggtgcctggt |
| | gagcagcagccagacgagcactggggaggtagcccgcccagcttgcctcttccccagatatcaacagg |
| | gtctftgtggcttcctgaaggctgtggctggaaaaagagggagggagctggggagggtctggccgctgttctt |
| | tctagaagcttttctttgtccagtggccccagcccaggtccccgtgttcttcccaggttggaaagctgcagag |
| | ggagtgcccagccactgtcagtcagcagctcctgctcatctctggcccttacacccagcaggggcagctgc |
| | gagggcaggggttgggtggggcaggagggtggcagcgtcctgggctccatgcacttggccaaagagg |
| | acttctgaacccgtccatcccagtgcgggtctgagagtggaacttgagggaaagggactgagtccccggga |
| | gccctctgcccctgccctccagccaggcagacttcctatctgcatgtatgggggtttgtgtctctgcttgtgtg |
| | tgtgtatttgtgtgtgtaacctccagtattcctgtttgtctgggtggggtcatatatttggttgcatgtgtgtgtgt |
| | gttcgtgaaccagcatgcacacacatattgtcatgaggccacgtgggtctcctcagatgccccaacagggc |
| | ctgtgctgggaaggggtggggctgaggtgctgctgcagtggctgatgggacagagcctctggcca |
| | acccaggctgtgcttcagtggagggggttccctgtgccctgtctcccagccatctgcgtctgtgttcatga |
| | cttaggaatgcccaagccctgggatcacagaggcccattgtccgccccggggcttcctgtgtccccctct |
| | gcccttaaccctcgggagtggggccctggagggggcccgtggggcctggcagtgtctgagctgtttcc |
| | aggcaccccacccgcccccgcaaaccaacacaggctaggtatcccaggactgctgtgggccaggg |
| | cctctccctgccccaggctgggctccttccctgctctccttacaggcacagcccaggaactggatgcagt |
| | ctgttccttctggcctggccgctgaagcccctctagtgctagggtcatcctagctccctgaggaggcctgg |
| | ggcctgagaggagccctagttttgctgccacctcatttctctcgccttctaggggtctc (SEQ ID NO: 1) |
| HOXA10 | tcgtcttttttccacgcacagcagcaatacaatattaatttattctgatttaagattagaagtaaatagagctagaa |
| | ctaacatttataataacgatagaatgcatttgcttaaaacaagattggcaattcttcataataatagacatttatac |
| | agatttgtatttatagtattacttatctgcatctacaggtttgacccattacatcacagtataaagga |
| | aatccaaacaatgtctccctctctagtttattccgcttacccagtcctcctaggcttctgtgaatttcagaaagc |
| | aaaaacaaacaaaaaaaaaacttttttgttcaaggcgatttaaaaaaacaacttcacaagatagggagaattgt |
| | ggtgtgcttgtcacatgttaccagtggtaacaattttaatgacaaaaaaatccactaattccaaatgcataaaca |
| | aaactacattatttatctacagccagaaggatatggaaatttagaggtaaatgaacattttagtcaggcaatgt |
| | aagacctttacagaaactggaagagaagtcccccttctcttggtaattctattattctattaaagctgggatatctt |
| | acagaggaaggaaaaattaacctatttactttcttttctcactattaaatcagccaaagtcaagcccgtttgccaa |
| | cctgcatgtccatgcctgtaagcccttctcttggccaaggaagaaaggaagaaagaaaaaagaaacccag |
| | gggcctgtatcccctgattaaacacagcacagcactccaggcagacatgcccggtggcggctcctttgcac |
| | cattgacctcaggccagacacctcagcgccaacaatgggacctcggccttccggctaggttttgccccaggc |

TABLE 4-continued

| Gene | Sequence |
|---|---|
| | tgggcaggaaaccagctcggccgaagacaggggccatttcgagcagtgggaccccaagacagcaaacc<br>cagcccagtcaggacttgacacttaggacaatatctatctctatagaatatagcatgatatggctattcccca<br>gaaaacaacaaataaaccagcaccaagcaaacacaaagaaacaaaaagtcagaacaaaccagccctgca<br>cagatgtaacggcccaggagatggcgagtgtgggagggaggaacagggctccagcacaggtgcgagtt<br>cctgggcagagcctgaagacagagggaggggaccagcgctcgggaagtgaaaaaaccgcgtcgcctg<br>gagattcatcaggaaaaattaaagttggctgtgagctcccggatccggttttctcgattcattttcttcagtttcat<br>cctgcggttctgaaaccagattttcacttgtctgtccgtgaggtggacgctgcggctaatctctaggcgccgct<br>ctcgagtaaggtacatattgaacagaaactccttctccagctccagtgtctggtgcttcgtgtaggggcagcg<br>cttcttccgaccactctttgccgtgagccagttggctgcgttttcacctttggaattgcctggcatgtaagagaat<br>aaagaggggatgattaagtcgaggcacacgggctgcccgcggggtgaattgcctccgtttctcccataa<br>gagagatgtcccaagtcacagagaagagagtcgtgccccccgtttttggcttgctgagagcaagcagttcctc<br>caaaagtcatgacaaaaattgagtgggccttcaatctacatgaccctttccaatttacatttccccccactttttccaa<br>acacctgttttagcgctaagccgtagatgcttgcagaaggaaaggcctggagggcaggctgtacatcttga<br>acttaacgcttttctttgcctcttgccatatggcagacaagcatttcctgtagcccccaggctaggagcgcggg<br>gtgcttacttggaagatgggccaggcagcttggctgtctcaccccagggccctgattgcccaagactcgata<br>aggggagaaagaagggcatcattggtccaatggggaaggcaggaaaaaccgattcgggggtcaagggc<br>cctccctcaagtttctccaggagccagggatagatagctgggcgattccgaggtcagggggaagggaaat<br>ggccctttctctggctctcagctcagggcccccgcttccaggccggatttgccttttcttcttcccgcaacgaa<br>gattcccgcccctcagcaacttttgaaaaaagcatggggggatcgtaaactcgaacttcgccggttaatgggctt<br>atttattggcgctggcggctgcttattttggatgccttacaaacatccgcgctatctgcgggcgagctactttcc<br>ctccctcccctcccccgcgtgggccgcgccgcgcaggctgggcagggaccagggctctgggtcctcc<br>cggccacaggaaagagcgcacaggagggggcctgctcgctggtgtcctcgtccctagtcagggggagct<br>gaggccagcgccgaggacgtcttgctgtggggcgctaagccggacatgaattttactgcgtccccacgc<br>caaatattaaaaagcaagttcacaaggtcagcctgcctgcagcttgggccaaggccggccggctgctgcg<br>cgggctcctagttttctgatccttctcctccttgtgtctgcctgtctgcccgcctgactgcagccctctgcagcc<br>ctgcttacccaggaatccttctccggcgaggctttgctgctctcggaaggggccggggagagctcctccg<br>cggccgaggacgacgcgtgcgcctcctcgtcgccctgcgagccccgcgctgccgcaagccagcgtg<br>gggggcggcggcgaatcgagggctcgctccttccgggccgcatcggccgagccggaggctagcgcgg<br>gcgggagatcgaaaccgcgccccgggggctgcgcggggaacgggccagccccgagttgctgcgcgcc<br>gccgccgccgctgccatagcccttggcggtgccgtaggcctgagaaaggcggaagtagccaggcactgg<br>caccccgctgagtgcccagggcgcagccgtcgggcggcgggcccgcgggaagggagccagttcg<br>gcggcggtggccgagactttgggcatttgtccgccgagtcgtagaggcagtaggagctctcttctttgatgt<br>tctgcgcgaaagagcacgaggtggcctgcggcgctggctggggtggttgcggcggggggcggcggctgc<br>tgctggggcggcggcggcggcccgtcaggcggctccatccggcaagaccggggcgcgtctagccaca<br>ggtctatgggcgagggcccgtagccgtgcgcccgggacctagaccccgccaccgccaccgctgccc<br>ggcgacgctgcctcattgcgcttgccgcccagcgtggggaagactactgcctctgcagcccgtagggc<br>aggtcggcggcgggcggcaggtagaccccgccgtgggcgtagtaaccgccaccgccgccgcccccg<br>cgccaccaccaccgccgcctgcctgcctctgcccgagctgatgagcgagtcgaccaaaaaagagttcgc<br>ggcgggctctccgagcatgacattgttgtgggataatttggcgaaggagcagatagccctttctggctga<br>catttcttgtgcaaaacatgctgaatacgattagcaatcccccccgcaccgcggcgggcgcccgcagccaat<br>cccgagccagagtttccgcgcgaccactcccagtttggtttcgtaggcgggggccgctctccgagggcg<br>ccctcagagcccgcgattgatataaatatgtaatctgtattgatgggcaggagacgcacccgacaccttg<br>gcccgaaggccgggagctgtgggggctgccccaacgtggctggtgggggggcctggccattgggctcgc<br>ccgccccctacccggacgtgagcccccataccgggtcccttagaaagggccctttgggcccccgcgagttaa<br>caagtggggtgtttatggtgcgcgcccagtctgccttgggtgctcaccatccctgtcgcagaagctgccact<br>agtccccggtgtactctaaccactgaagcggccgtgtcggggactcacgcgcttcccattcagctctggatc<br>tggaactggccccttgtctgaattctgcctcctcaaaagtggcgaacctggccctatggccgtcaggatcctc<br>agagtgtcaggagcccagagtgaactagaagctgacttgcctctacttccagtatccacagatttttccccaa<br>aatgcagtggttgttccctagcccta (SEQ ID NO: 2) |
| CDKN2B | ggttgccactctcaatctcgaactagttatttctcttttaaggggttgtatccataatgcaaaaatggaaagaatta<br>aaaagcacacgcaaaacatgattctcgggattttttctctatttttatggttgactaattcaaacagaaagacacat<br>ccaagagaaaattgctaagtttgatacaagttatgaaacttgtgaagcccaagtactgcctggggatgaattta<br>acttgtatgacaggtgcagagctgtcgctttcagacatcttaagaaacacggagttattttgaatgactttctctc<br>ggtcacaaggggagccaccaacgtctccacagtgaaaccaactggctggctgaaggaacagaaatcctctg<br>ctccgcctactggggattaggagctgagggcagtggtgaacattcccaaaatattagccttggctttactgga<br>catccagcgagcagtgcagccagcattcctggcggctccctggccagtctctggcgcatgcgtcttagca<br>tctttgggcaggcttccccgccctcgtgacgcgtcggcccgggcctggcctcccggcgatcacagcggac<br>agggggcggagcctaaggggtggggagacgccggcccctggcccagctgaaaacgaattcttttgcc<br>ggctggctccccactctgccagagcgaggcggggcagtgaggactccgcgacgcgtccgcaccctgcg<br>gccagagcggctttgagctcggctgcgtccgcgctcaggcgctttttcccagaagcaatccaggcgcgcc<br>gctggttcttgagcgccaggaaaagcccggagctaacgaccggccgctcggccactgcacgggggcccca<br>agccgcagaaggacgacgggagggtaatgaagctgagcccaggctcctaggaaggagagagtgcgcc<br>ggagcagcgtgggaaagaagggaagagtgtcgttaagtttacggccaacggtggattatccgggccgctg<br>cgcgtctggggggctgcggaATGCGCGAGGAGAACAAGGGCATGCCCAGTG<br>GGGGCGGCAGCGATGAGGGTCTGGCCAGCGCCGCGGCGCGGGG<br>ACTAGTGGAGAAGGTGCGACAGCTCCTGGAAGCCGGCGCGGATC<br>CCAACGGAGTCAACCGTTTCGGGAGGCGCGCGATCCAGGTAGCT<br>GGGGCCCCAGGGCCTCGCCGGCAGGGGGCGCGAACGCGGGG<br>CGCGGCCTCGGCGGATCGGGGCTGGAACCTAGATCGCCGATGTA<br>GATTTGTACAGGAGTCTCCGTTGGCCGGAGGTGTGCATTCCACGC<br>GTAAAACAGGCTTTTACCCAGCAAAAATCCTAAAGAGAGACATT<br>GAAAAACCCACTGTTTAAGCTTTTTTTAGTGGTTTTTGTTCTGCCA<br>TCTCATGATCAGAGATGCAAGGAATAGACTGAATTGGGGAGAAA<br>AGGAGAAAAGGAAAGCTTATTTAGGGAAGAAGATTATCTTGTCT<br>GTCTGCTTTCAACGATAAAGATAAGTAAAGTATAAGTTACGCAT<br>TCTAGATTGGATTTAAGGAATTCTACAAAATCATAGTACATGGA<br>AAAAATCAATGTAAACTTCTAAGCTACTATATGAAATCTGTTGTA |

TABLE 4-continued

| Gene | Sequence |
|---|---|
| | TTGTTTTCTCATAGAGGTTAATTGAGAATGAGACGGGATTCCTCA<br>ACCACAGTACTTAGTTCCTTTTATGTTAGCAGTGTCTTATGAGTG<br>ATGCATAAGAGAAAAAATATATAGTTCTATAGGTTTCTCATTCTT<br>TAATTATCATACTCAGTGCCCAGATTACAAAAATATTCCTGCAGC<br>AACTGTTAGGTCCTTTTTGAATGGCAAAGGATCTTCATAAATAAT<br>GCATCTTTATCTTCATTGTTAAAATACACTTATTCAATGTTTAAGT<br>ACGAATCCTGCTTTAATTAGTACTGATATTTTTATTTCTTTTACA<br>ATCTCGGACAACTCTTTTGTACTTTACCGTTGGCTAGTGGTCATA<br>TTCAGTACTCACCTCACTATCACCCTCTAAAACTAAGCTAATATT<br>AAGGGATCTTGTTAATAGTATAGATTTTAAAGAAGTGTTCATTTC<br>TTTTGAATTCTTAGAATAATGGTATAACAAATGAGGGATTTTTAA<br>AGGAGCAAAAATATTGTAAAGTGCATCTTAAAAACTTAAAATTT<br>TATTAATAATTATAAAAACAAGTTATATATGTAATTCACCATTTT<br>CTGAAATACTAACAGCAGCTATTTTCCCCTTTTTTCTATGTAAA<br>ATATCCTTACATCACTAGTAGATATAACTTATCACGGTTTTTAAG<br>AGATGAAATGAACATTTCTAATATTAATGAAACAAGCCAACAAA<br>ACATGAGAAGTATACTGCCTTTCAATTAAATGGTATATTTTAAAG<br>TGCATAAACCCATAACAAATAACTCGATTTTAGACATTTAGTTAC<br>CAAAAATTGTCTTATAATTGACTTTAAATATGACAGCAAATGTTT<br>TCATAATGTTCATGTACACAAATGGCTGCTACAGGATTACTCCTG<br>CAAAACATCATTTTTTCTAAGTTATGCATCATCCTGATTGACTGC<br>TAACATCCAAGCTCTATTTATTTATTTATTTTATTTTTTTGA<br>GATGAGGCCTCACTCTGTCGGACAGGCTGGAGTGCAGTGGCACA<br>ATCTCAGCTCACTGCAACCTCTTCCAGGATGCAAGCGATTCTCCT<br>GCCTCAGCCTCCTGAGTTGCTGGGACTACAGGCACGCCCCACCA<br>TGCCCAGCTAATTTTTATTTTTGTAGTAGAGACGGGATTTCAC<br>CATGTTGGCCAGGCTGGTCTCGAACTCCTGACCTCAGGTGATCTG<br>CCTGCTATGGCCTCCCAAAGTGCTGGGATTACAGGCATAAGCCA<br>CTGGGCCTGGCCCAAGCTCTTTTTATATAGCAAAATATTTACTGT<br>TTAACATTTTTAAATCTTAGCTATTATAAAATCCTGTAGTATACA<br>AATATAGTTAGTTTTATATTACATTAAAAATATTATAGTCTAAAT<br>TTAAAATGATGAACTGTTAAGGAAAAATCATTTATTATAATTTTA<br>TAAGATTTTGCATGATTTAATTTACTTTTCCCTTCTAATCTCCAAC<br>TTTGGCTCAAATTATCACACTACAAGCCAGTTATGAGCTCAGACA<br>CATGACAAACAAAAGCCTTCCGCACGGGATTTGCTATGAGAACT<br>AAATAAATTAAAAAAAAAAGAAAGAAAAAAACTTAGTTGTTTAT<br>TTTCTCCCCTAAACCATTACTCCCAACTTCTAACAAACAGTAGTT<br>GACTACCTAATAAATATTTGTAGACCTGGATTATGGAGGAGGGG<br>TCAGCAAGGCAAATAATTTAAAACTTTAAAAGCCGAATAAATTT<br>AACTCTGCCCCTAAATCATTTAACAAAATAGATTCCCATGTTCCA<br>ATGGAAATCAAGATTTGTTTTTCCATAATGATGATCATCACTTTA<br>CCATCAACTTTCTTGTCTCTGCACGTTTAGAGAATAAAATGGCAT<br>TTAATTTGTACTGAGTATAACCTGAAGGTGGGGTGGGAAAGTGG<br>ATTGCATCAGCAAATGAAGAAACACCAGACATCAGAGACCTGAA<br>CACCTCTGCACTGGGTGAAAACTTTGCAATTAGGTGTTTCTTTAA<br>ATGGCTCCACCTGCCTTGCCCCGGCCGGCATCTCCCATACCTGCC<br>CCCACCCTGGCTCTGACCACTCTGCTCTCTCTGGCAGGTCATGAT<br>GATGGGCAGCGCCCGCGTGGCGGAGCTGCTGCTGCTCCACGGCG<br>CGGAGCCCAACTGCGCAGACCCTGCCACTCTCACCCGACCGGTG<br>CATGATGCTGCCCGGGAGGGCTTCCTGGACACGCTGGTGGTGCT<br>GCACCGGGCCGGGGCGCGGCTGGACGTGCGCGATGCCTGGGGTC<br>GTCTGCCCGTGGACTTGGCCGAGGAGCGGGGCCACCGCGACGTT<br>GCAGGGTACCTGCGCACAGCCACGGGGACTGAcgccaggttccccagcc<br>gcccacaacgactttaillicttacccaatttcccaccccaccacctaattcgatgaaggctgccaacggg<br>gagcggcggaaagcctgtaagcctgcaagcctgtctgagactcacaggaaggaggagccgaccgggaa<br>taaccttccatacallatactttgtcttatctggccctcgacactcaccatgaagcgaaacacagagaagcgg<br>atttccagggatatttaggagtgtgtgacattccaggggtcgtttgcttttcagggttttctgagggaaagtgcat<br>atgaaatccttgactggacctggtggctacgaatcttccgatggatgaatctcccactccagcgctgagtggg<br>agaaggcagtgattagcacttgggtgacggcagtcgatgcgttcactccaatgtctgctgaggagttatggt<br>gaacccacaacttaggccctagcggcagaaaggaaaacctgaagactgaggacaaagtggaggagggc<br>cgaggtgggcttcagtaagtccccggcggcgctttagtttgagcgcatggcaagtcacatgcgtaaacgac<br>actctctggaagccctggagaccctcgcccaactccaccagatagcagaggggtaagagaggatgtgcaa<br>gcgacgacaga (SEQ ID NO: 3) |

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

---

The invention claimed is:

1. A method of detecting the presence of at least one target modified or unmodified DNA sequence in a DNA molecule, the method comprising:
   a. contacting said DNA molecule with at least one DNA methyltransferase enzyme (MTase) in the presence of a synthetic cofactor of said MTase, wherein said enzyme differentially binds and deposits at least a detectable moiety from said synthetic cofactor on said target sequence depending on the presence of said modification,
   b. passing said contacted DNA molecule through a nanopore of membrane or film of an apparatus comprising said membrane or film comprising said nanopore, and an electrical sensor, wherein said electrical sensor is configured to detect ion flow through said nanopore, and wherein said detectable moiety is detectable as it passes through said nanopore; and
   c. detecting said DNA molecule as it passes through said nanopore and detecting if said detectable moiety is present as said DNA molecule passes through said nanopore, wherein said enzyme binds and deposits on modified DNA and said presence of said detectable moiety indicates the presence of said target modified DNA sequence or said enzyme binds and deposits on unmodified DNA and said presence of said detectable moiety indicates the presence of said target unmodified DNA sequence;
   thereby detecting the presence of at least one target DNA sequence with or without a modification.

2. The method of claim 1, wherein said synthetic cofactor is a steric S-adenosyl-L-methionine (AdoMet) analog.

3. The method of claim 1, wherein said synthetic cofactor comprises a bulky group sufficiently big to alter ion flow through the nanopore and wherein said detecting is said detectably moiety is present comprises detecting ion current blockade produced by said bulky group.

4. The method of claim 3, wherein said bulky group is gamma cyclodextrin.

5. The method of claim 1, wherein said synthetic cofactor comprises a fluorophore, and said apparatus comprises an optical sensor, wherein said optical sensor is configured to detect fluorescence at said nanopore.

6. The method of claim 5, wherein said fluorophore is selected from a red fluorophore, an orange fluorophore, a green fluorophore and a blue fluorophore.

7. The method of claim 5, wherein said detecting if said detectable moiety is present comprises determining the fluorescence per base pair of the molecule.

8. The method of claim 5, wherein said detecting if said detectable moiety is present comprises detecting fluorescence before said molecule translocates through said nanopore, after said molecule translocates through said nanopore or both, and removing background fluorescence from fluorescence measured as said molecule translocates through said nanopore.

9. The method of claim 1, wherein said DNA modification is DNA methylation.

10. The method of claim 9, wherein said DNA methylation is selected from 5-methylcytosine and 5-hydroxymethylcytosine.

11. The method of claim 1, wherein said enzyme binds to and transfers said detectable moiety to only modified or only unmodified target sequence.

12. The method of claim 1, wherein said enzyme binds to a target sequence comprising a cytosine-guanine dinucleotide (CpG).

13. The method of claim 1, wherein said enzyme is selected from M.TaqI, M.SssI, M.BscCI, M.EcoDam, M.HhaI, and MpeI.

14. The method of claim 13, wherein said MTase is M.TaqI and said method detects unmethylated target sequence.

15. The method of claim 1, for detecting a modified or unmodified target sequence, wherein said target sequence is within 5 base pairs of a differently modified target sequence.

16. The method of claim 1, wherein said depositing comprising covalent linkage of said detectable moiety to said DNA molecule.

17. The method of claim 1, wherein said apparatus comprises a first fluid reservoir and a second fluid reservoir and wherein said first and second fluid reservoirs are in electrical contact with each other via said nanopore.

18. The method of claim 17, wherein said passing comprises running electrical current from said first reservoir to said second reservoir via said nanopore and wherein said first and second reservoirs contain fluid suitable for transferring said DNA molecule through said nanopore via said electrical current, or wherein said DNA molecule is within a solution, and wherein said passing comprises placing said solution in said first reservoir.

19. The method of claim 18, further comprising removing from said solution synthetic cofactor that is not deposited on DNA before said placing.

20. The method of claim 1, wherein said membrane or film comprises a thickness of less than 50 nanometers.

* * * * *